(12) United States Patent
Osborne et al.

(10) Patent No.: US 10,961,233 B2
(45) Date of Patent: Mar. 30, 2021

(54) OXAZOLE DERIVATIVES FOR USE IN THE TREATMENT OF CANCER

(71) Applicant: LIFEARC, London (GB)

(72) Inventors: Simon Osborne, London (GB); Jonathan Large, London (GB)

(73) Assignee: LIFEARC, London (GB)

( * ) Notice: Subject to any disclaimer, the term of this patent is extended or adjusted under 35 U.S.C. 154(b) by 0 days.

(21) Appl. No.: 16/474,114

(22) PCT Filed: Dec. 19, 2017

(86) PCT No.: PCT/GB2017/053821
§ 371 (c)(1),
(2) Date: Jun. 27, 2019

(87) PCT Pub. No.: WO2018/122549
PCT Pub. Date: Jul. 5, 2018

(65) Prior Publication Data
US 2019/0352295 A1 Nov. 21, 2019

(30) Foreign Application Priority Data

Dec. 29, 2016 (GB) .................................. 1622362

(51) Int. Cl.
*C07D 413/12* (2006.01)
*C07D 413/14* (2006.01)
*C07D 263/48* (2006.01)

(52) U.S. Cl.
CPC ......... *C07D 413/14* (2013.01); *C07D 263/48* (2013.01); *C07D 413/12* (2013.01)

(58) Field of Classification Search
CPC ... C07D 413/12; C07D 413/14; C07D 263/48
See application file for complete search history.

(56) References Cited

FOREIGN PATENT DOCUMENTS

| EP | 2 009 005 A1 | 12/2008 |
| WO | 8403564 A1 | 9/1984 |
| WO | 2018122549 A1 | 7/2018 |

OTHER PUBLICATIONS

Golub et al., Science, vol. 286, Oct. 15, 1999, pp. 531-537 (Year: 1999).*
Barfeld S J et al., Myc-dependent purine biosynthesis affects nucleolar stress and therapy response in prostate cancer, Oncotarget, May 20, 2015;6(14):12587-602.
Berge S M et al, Pharmaceutical Salts, Journal of Pharmaceutical Sciences, 1977, vol. 66, pp. 1-19.
Eißmann M et al., A functional yeast survival screen of tumor-derived cDNA libraries designed to identify anti-apoptotic mammalian oncogenes, PLoS One, May 22, 2013;8(5):e64873.
Fingl E and Woodbury D M, In: The Pharmacological Basis of Therapeutics, 1975, 5th edition, chapter 1, p. 1-46.
Gennaro A R (editor) Remington's Pharmaceutical Sciences, 1985, 17th edition, Mack Publishing, Table of Content Pages Only.
Goswami M T et al., Role and regulation of coordinately expressed de novo purine biosynthetic enzymes PPAT and PAICS in lung cancer, Oncotarget, Sep. 15, 2015;6(27):23445-61.
March J (editor) Advanced Organic Chemistry, 1985, 3rd edition, John Wiley & Sons, New York.
Sander J D and Joung J K, CRISPR-Cas systems for editing, regulating and targeting genomes, Nature Biotechnology Apr. 2014, vol. 32(4) pp. 347-355.
Wade A and Weller P J (editors) Handbook of Pharmaceutical Excipients, 1994, 2nd edition, Cover Page and Copyright Page Only.
Chakravarthi et al. (2017) "Expression and Role of PAICS, a De Novo Purine Biosynthetic Gene in Prostate Cancer," The Prostate, 77:10-21.
Osborne, S. (2017) "Fragment optimisation without co-crystal X-ray structures: from hits to nanomolar inhibitors of human PAICS," Fragments 2017, 6th RSC-BMCS Fragment based Drug Discovery Meeting, 42 pages.
"Sunday-Tuesday, Mar. 5-7, 2017, Second announcement and call for posters 6th RSC-BMCS Fragment-based Drug Discovery meeting Fragment 2017," 2 pages.
International Search Report for International Application No. PCT/GB2017/053821, dated Mar. 15, 2018.

* cited by examiner

*Primary Examiner* — Laura L Stockton
(74) *Attorney, Agent, or Firm* — Lathrop GPM LLP; Brian C. Trinque, Esq.

(57) ABSTRACT

A first aspect of the invention relates to a compound of formula (I), or a pharmaceutically acceptable salt or ester thereof, • B is a saturated or partially unsaturated monocyclic or bicyclic, heterocyclic group optionally substituted by one or more R 10 groups; *X is selected from $SO_2$, $CO_2$, CO, $CONR^{11}$ and $(CR^{12}R^{13})$ p. Said compounds are capable of inhibiting PAICS and are useful in the treatment of proliferative disorders. Further aspects relate to pharmaceutical compositions, therapeutic uses and process for preparing compounds of formula (I).

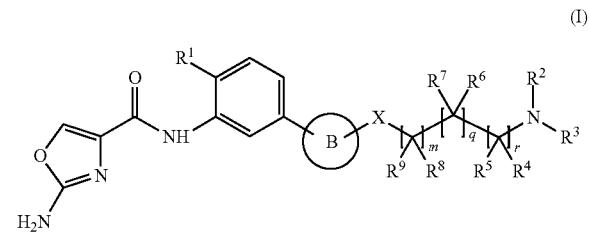

19 Claims, 5 Drawing Sheets

OXAZOLE DERIVATIVES FOR USE IN THE TREATMENT OF CANCER

CROSS-REFERENCE TO RELATED APPLICATIONS

This application is a 35 U.S.C. § 371 filing of International Application No. PCT/GB2017/053821, filed on Dec. 19, 2017, which claims priority to Great Britain patent application number 1622362.0, filed Dec. 29, 2016.

FIELD OF THE INVENTION

The present invention relates to substituted oxazole derivatives that are capable of inhibiting PAICS. The compounds find applications in the treatment of a variety of disorders, including proliferative disorders such as cancer.

BACKGROUND TO THE INVENTION

PAICS (phosphorlbosylaminoimidazole carboxylase, phosphoribosylaminoimidazole succinocarboxamide synthetase) is a bifunctional 46 kD enzyme catalysing the 6th and 7th steps of the de novo purine pathway (see FIG. 1).

PAICS converts 5-aminoimidazole ribonucleotide (AIR) to 4-carboxy-5-aminoimidazole ribonucleotide (CAIR) in an ATP dependent reaction, before finally generating 4-(N-succinylcarboxamide)-5-aminoimidazole ribonucleotide (SAICAR) in a carboxylation reaction (see FIG. 2). This reaction series feeds into the overall generation of inositiol monophosphate (IMP), a nucleotide that forms the substrate for AMP and GMP production, from phosphoribosyl pyrophosphate (PRPP). The inhibition of folic acid, pyrimidine and purine biosynthetic pathways has proved an attractive drug target for cancer chemotherapy as rapidly dividing cancer cells have a high biosynthetic requirement in comparison to non-transformed cells.

Recent literature has highlighted PAICS as an emerging novel target for cancer therapeutics. PAICS was identified as an anti-apoptotic oncogene, with PAICS shRNA protein knock-down reducing the proliferation of a melanoma cell line in vitro. Furthermore, subcutaneous injection of PAICS knock-down cells in a xenograft model significantly reduced the rate of tumour growth (Eilmann et al., PLoS One, 2013 May 22; 8(5):e64873).

PAICS expression is significantly upregulated in lung cancer, and moreover expression levels were related to the prognosis of the patient population; increased expression of PAICS was coupled with tumours of a more aggressive nature. Xenograft models performed using lung cancer PAICS knock-down cells led to a significant reduction in tumour volume and weight after several weeks (Goswami et al., Oncotarget, 2015 Sep. 15; 6(27):23445-61). PAICS over-expression has been also associated with a wide range of other tumour types.

Further studies indicated that PAICS may be a useful biomarker too for poor prognosis prostate cancer, with heightened expression found in prostate cancer and the severe castration-resistant form, relative to benign prostate hyperplasia samples (Barfeld et al., Oncotarget, 2015 May 20; 6(14):12587-602).

During the recent emergence of PAICS as a potential target for cancer therapeutics, studies have demonstrated that the PAICS gene is overexpressed as part of a nine gene-expression signature that is strongly associated with poor-prognosis in triple negative breast cancer (TNBC) patients. Experimental knock-down of any one of these genes had a marked inhibitory effect on cancer cell growth and metastasis in vitro and in vivo. Specifically, shRNA inhibition of PAICS expression strongly impaired primary tumour growth when breast cancer cells were injected orthotopically in the mammary fat pad of mice. Down regulation of PAICS expression in highly metastatic human breast cancer cells abolished the ability of these cells to form metastases to the lungs when injected intravenously into immunocompromised mice. Of note, this highly predictive gene-expression signature has a similar prognostic power in breast cancer patients as the gene-expression signatures, MammaPrint® or OncotypeDX®, currently used in the clinic.

The present invention seeks to provide small molecule inhibitors of PAICS. In a preferred aspect, the invention seeks to provide small molecule inhibitors of PAICS that target the SAICAR synthetase domain. Such small molecule inhibitors have potential therapeutic applications in the treatment of proliferative disorders such as cancer.

STATEMENT OF INVENTION

A first aspect of the invention relates to a compound of formula (I), or a pharmaceutically acceptable salt or ester thereof,

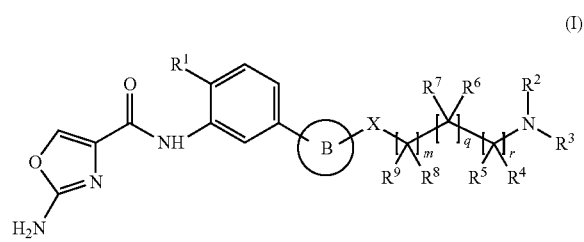

wherein:

B is a saturated or partially unsaturated monocyclic or bicyclic, heterocyclic group optionally substituted by one or more $R^{10}$ groups and optionally containing one or more CO groups;

X is selected from $SO_2$, $CO_2$, CO, $CONR^{11}$, $NR^{11}CO$ and $(CR^{12}R^{13})_p$;

each $R^1$ is independently selected from halogen, $OR^{14}$, $SR^{14}$ and $R^{14}$;

$R^2$ is selected from H and alkyl;

$R^3$ is selected from alkyl, cycloalkyl and heterocycloalkyl, each of which is optionally substituted by one or more substituents selected from $NR^{24}R^{25}$ and $R^{26}$; or $R^2$ and $R^3$ are linked together with the nitrogen to which they are attached to form a saturated heterocyclic group optionally containing one or more additional heteroatoms selected from O, N and S, and optionally substituted by one or more $R^{27}$ groups;

each $R^4$ and $R^5$ is independently selected from H, alkyl, $(CH_2)_sOR^{15}$ and $(CH_2)_tNR^{16}R^{17}$; or one of $R^4$ and $R^5$ is H or alkyl and the other is linked to $R^3$ to form a saturated heterocyclic group;

each $R^6$ and $R^7$ is independently selected from H, alkyl, $(CH_2)_wOR^{18}$ and $(CH_2)_vNR^{19}R^{20}$; or one of $R^6$ and $R^7$ is H or alkyl and the other is linked to $R^3$ to form a saturated heterocyclic group;

each $R^8$ and $R^9$ is independently selected from H, alkyl, $(CH_2)_wOR^{21}$ and $(CH_2)_xNR^{22}R^{23}$; or one of $R^8$ and $R^9$ is H or alkyl and the other is linked to $R^3$ to form a saturated heterocyclic group; or one of $R^8$ and $R^9$ is linked to one of $R^4$ and $R^6$ to form a cyclic group;

$R^{10}$ is selected from alkyl, OH, halogen, alkoxy, $CO_2$-alkyl, COOH, CO-alkyl and CN;

$R^{11}$, $R^{12}$, $R^{13}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ are each independently H or alkyl;

$R^{14}$, $R^{26}$ and $R^2$ are each independently alkyl;

m, q and r are each independently 0, 1 or 2, such that the sum of m+q+r is 2, 3 or 4;

n is an integer selected from 1, 2, 3 and 4;

p is an integer selected from 0, 1 and 2; and s, t, u, v, w and x are each independently 0, 1, 2, 3 or 4.

A second aspect of the invention relates to a pharmaceutical composition comprising at least one compound as described above and a pharmaceutically acceptable carrier, diluent or excipient.

A third aspect of the invention relates to a compound as described above for use in medicine.

A fourth aspect of the invention relates to a compound as described above for use in treating a proliferative disorder.

A fifth aspect of the invention relates to the use of a compound as described above in the preparation of a medicament for treating or preventing a proliferative disorder.

A sixth aspect of the invention relates to a method of treating a proliferative disorder in a subject in need thereof, said method comprising administering to the subject a therapeutically effective amount of a compound as described above.

A seventh aspect of the invention relates to a method of treating a subject having a disease state alleviated by inhibition of PAICS, wherein the method comprises administering to the subject a therapeutically effective amount of a compound as described above.

An eighth aspect of the invention relates to the use of a compound as described above in an assay for identifying further candidate compounds capable of inhibiting PAICS.

A ninth aspect of the invention relates to a combination comprising a compound as described above and a second therapeutic agent.

A tenth aspect of the invention relates to a process for preparing compounds as described herein.

DETAILED DESCRIPTION

The present invention relates to substituted oxazole derivatives that are capable of inhibiting PAICS.

"Alkyl" is defined herein as a straight-chain or branched alkyl radical, for example, methyl, ethyl, propyl, isopropyl, butyl, isobutyl, tert-butyl, pentyl, hexyl. Preferably, the alkyl group is a $C_{1-12}$-alkyl group, more preferably, a $C_{1-6}$-alkyl group, even more preferably a $C_{1-4}$-alkyl group.

"Cycloalkyl" is defined herein as a monocyclic alkyl ring, such as, cyclopropyl, cyclobutyl, cyclopentyl, cyclohexyl or cycloheptyl, or a fused bicyclic ring system such as norbornane. Preferably, the cycloalkyl group is a $C_{3-8}$-cycloalkyl group, more preferably a $C_{3-6}$-cycloalkyl group.

"Halogen" is defined herein as chloro, fluoro, bromo or iodo.

The compounds of the invention comprise group B, which is a saturated or partially unsaturated monocyclic or bicyclic heterocyclic group.

As used herein, the term "heterocyclic group" is defined herein as a cyclic aliphatic group comprising one or more heteroatoms (that may be the same or different), such as oxygen, nitrogen or sulfur, which is optionally interrupted by one or more —(CO)— groups in the ring. Preferably, the heterocyclic group is a $C_3$-$C_7$-heterocycloalkyl group, more preferably a $C_3$-$C_6$-heterocycloalkyl group. Alternatively, the heterocycloalkyl group is a $C_4$-$C_7$-heterocycloalkyl, more preferably a $C_4$-$C_6$-heterocycloalkyl.

Preferably, the heterocyclic group B is saturated. However, in certain embodiments, the heterocyclic group may contain one or more double bonds such that it is partially unsaturated.

Preferably, the heterocyclic group B is a monocylic saturated heterocyclic group. Particularly preferred monocylic saturated heterocyclic groups include, but are not limited to, piperazinyl, piperidinyl, morpholinyl, thiomorpholinyl, pyrrolidinyl, tetrahydrofuranyl and tetrahydropyranyl.

More preferably, heterocyclic group B is selected from piperazinyl, piperidinyl, morpholinyl, thiomorpholinyl and pyrrolidinyl. More preferably still, heterocyclic group B is selected from piperazinyl, piperidinyl and pyrrolidinyl.

In one preferred embodiment, heterocyclic group B is substituted by one or more $R^{10}$ groups, preferably by one $R^{10}$ group. In another preferred embodiment, heterocyclic group B is unsubstituted.

In one preferred embodiment, heterocyclic group B contains one or more CO groups, preferably one CO group.

Preferably, where:

one of $R^6$ and $R^7$ is H or alkyl (more preferably methyl) and the other is linked to $R^3$ to form a saturated heterocyclic group, or one of $R^8$ and $R^9$ is H or alkyl (more preferably methyl) and the other is linked to $R^3$ to form a saturated heterocyclic group, or one of $R^4$ and $R^5$ is H or alkyl (more preferably methyl) and the other is linked to $R^3$ to form a saturated heterocylic group;

the saturated heterocyclic group is a 4-, 5- or 6-membered heterocyclic group, more preferably, 5- or 6-membered heterocyclic group, even more preferably, a pyrrolidinyl or piperidinyl group.

In one preferred embodiment of the invention, B is a monocylic 5- or 6-membered saturated or partially unsaturated heterocyclic group optionally containing one or more CO groups and optionally substituted by one or more $R^{10}$ groups.

In one preferred embodiment of the invention, B is a monocylic 5- or 6-membered saturated or partially unsaturated heterocyclic group optionally substituted by one or more $R^{10}$ groups.

In one particularly preferred embodiment, B is a piperazinyl group or a piperidinyl group, each of which is optionally substituted with one or more $R^{10}$ groups.

In another particularly preferred embodiment, B is a piperazinyl group or a piperidinyl group, wherein for each group, one of the methylene groups is replaced with a CO group.

In one preferred embodiment of the invention:

each $R^4$ and $R^5$ is independently selected from H and alkyl; or one of $R^4$ and $R^5$ is H or alkyl and the other is linked to $R^3$ to form a saturated heterocyclic group.

In one preferred embodiment of the invention:

each $R^8$ and $R^7$ is independently selected from H, alkyl, $(CH_2)_uOR^{18}$ and $(CH_2)NR^{19}R^{20}$; or one of $R^6$ and $R^7$ is H or alkyl and the other is linked to $R^3$ to form a saturated heterocyclic group.

In one preferred embodiment of the invention:
each $R^8$ and $R^9$ is independently selected from H, alkyl, $(CH_2)_wOR^{21}$ and $(CH_2)_xNR^{22}R^{23}$; or one of $R^8$ and $R^9$ is H or alkyl and the other is linked to $R^3$ to form a saturated heterocyclic group.

In one preferred embodiment of the invention:
each $R^4$ and $R^5$ is independently selected from H and alkyl; or
one of $R^4$ and $R^5$ is H or alkyl and the other is linked to $R^3$ to form a saturated heterocyclic group;
each $R^6$ and $R^7$ is independently selected from H, alkyl, $(CH_2)_uOR^{18}$ and $(CH_2)_vNR^{19}R^{20}$; or one of $R^5$ and $R^7$ is H or alkyl and the other is linked to $R^3$ to form a saturated heterocyclic group; and
each $R^8$ and $R^9$ is independently selected from H, alkyl, $(CH_2)_wOR^{21}$ and $(CH_2)_xNR^{22}R^{23}$; or one of $R^8$ and $R^9$ is H or alkyl and the other is linked to $R^3$ to form a saturated heterocyclic group.

In one preferred embodiment of the invention, the compound is of formula (Ib), or a pharmaceutically acceptable salt or ester thereof,

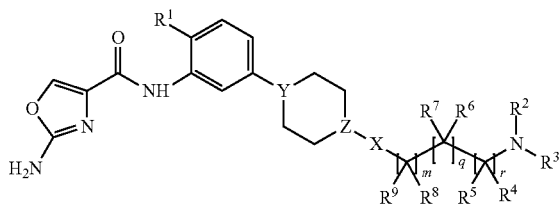

(Ib)

wherein Y and Z are both N, or one of Y and Z is N, and the other is CH; and
$R^{1-9}$, X, m, q and r are as defined above.

In one preferred embodiment, Y and Z are both N.
In one preferred embodiment, $R^1$ is selected from Br, I, Cl, OMe, SMe and Me. More preferably, $R^1$ is selected from Br, Cl and SMe.

In one preferred embodiment, X is $CO_2$ or $SO_2$, more preferably $SO_2$.

In one preferred embodiment, $R^2$ is selected from H, methyl, ethyl and isopropyl; and
$R^3$ is selected from methyl, ethyl, isopropyl and cyclopropyl.

In one preferred embodiment, $R^2$ and $R^3$ are linked together with the nitrogen to which they are attached to form a 5- or 6-membered saturated heterocyclic group, preferably a pyrrolidinyl group.

In one preferred embodiment:
m is 1 or 2;
q is 1 or 2, more preferably 1;
r is 0;
$R^8$ and $R^9$ are each independently H or alkyl, more preferably H; and
$R^6$ and $R^7$ are each independently H or alkyl, more preferably H.

In another preferred embodiment:
m is 1;
q is 1 or 2;
r is 0;
one of $R^8$ and $R^9$ is H or alkyl and the other is linked to $R^3$ to form a saturated heterocyclic group; and
each $R^6$ and $R^7$ is independently H or alkyl.

In another preferred embodiment:
m is 1;
q is 1;
r is 1 or 2, preferably 1;
$R^8$ and $R^9$ are each independently H or alkyl, more preferably H;
one of $R^6$ and $R^7$ is H or alkyl and the other is linked to $R^3$ to form a saturated heterocyclic group; and
$R^4$ and $R^5$ are each independently H or alkyl, more preferably H.

In one highly preferred embodiment, the compound of the invention is selected from compounds shown in the table below:

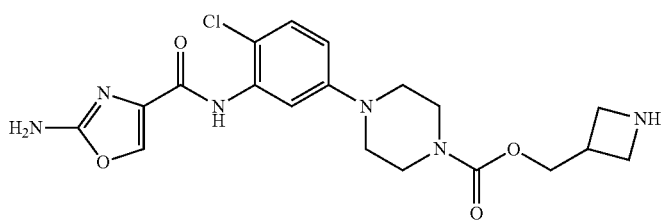 [SMILES: Nc1nc(C(=O)Nc2cc(N3CCN(C(=O)OCC4CNC4)CC3)ccc2Cl)co1]

19

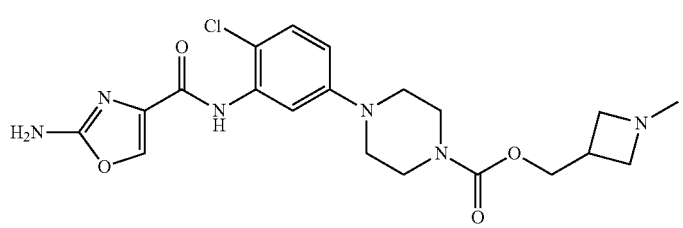 [SMILES: CN1CC(COC(=O)N2CCN(c3ccc(Cl)c(NC(=O)c4coc(N)n4)c3)CC2)C1]

20

-continued
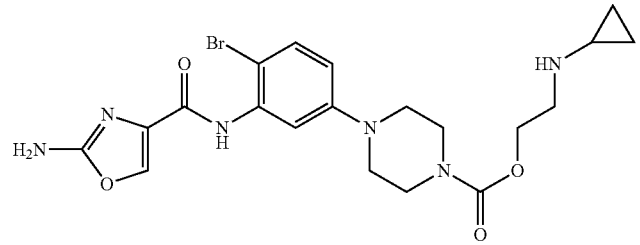 [SMILES: Nc1nc(C(=O)Nc2cc(N3CCN(C(=O)OCCNC4CC4)CC3)ccc2Br)co1]
21
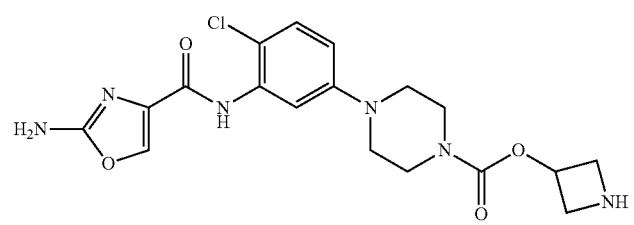 [SMILES: Nc1nc(C(=O)Nc2cc(N3CCN(C(=O)OC4CNC4)CC3)ccc2Cl)co1]
22
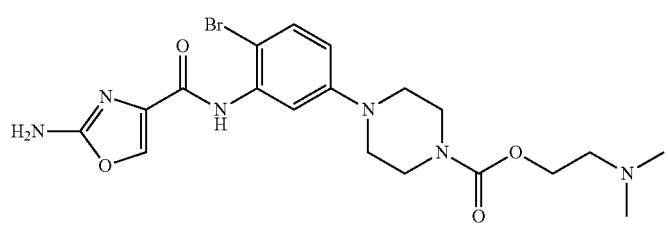 [SMILES: CN(C)CCOC(=O)N1CCN(c2ccc(Br)c(NC(=O)c3coc(N)n3)c2)CC1]
23
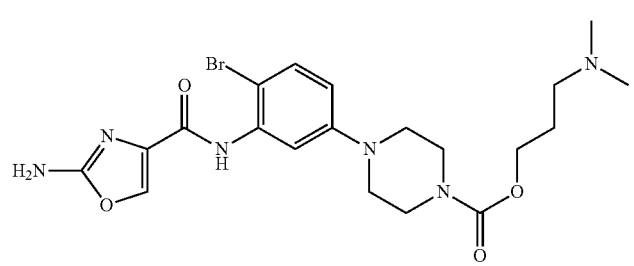 [SMILES: CN(C)CCCOC(=O)N1CCN(c2ccc(Br)c(NC(=O)c3coc(N)n3)c2)CC1]
24
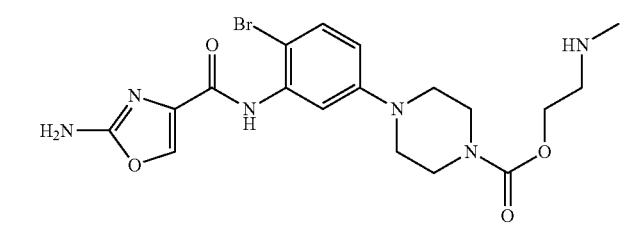 [SMILES: CNCCOC(=O)N1CCN(c2ccc(Br)c(NC(=O)c3coc(N)n3)c2)CC1]
25
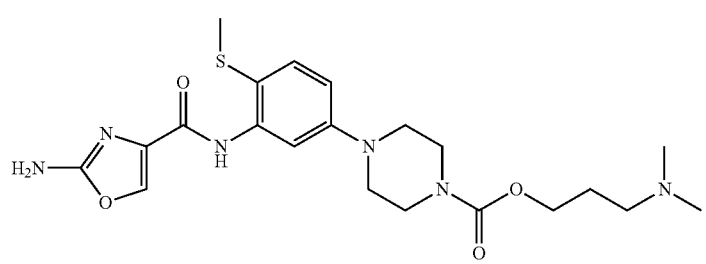 [SMILES: CSc1ccc(N2CCN(C(=O)OCCCN(C)C)CC2)cc1NC(=O)c1coc(N)n1]
26

-continued
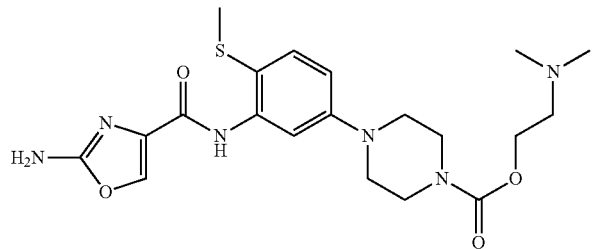 [SMILES: CSc1ccc(N2CCN(C(=O)OCCN(C)C)CC2)cc1NC(=O)c1coc(N)n1]
27
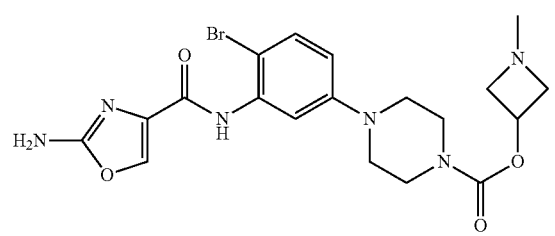 [SMILES: CN1CC(OC(=O)N2CCN(c3ccc(Br)c(NC(=O)c4coc(N)n4)c3)CC2)C1]
28
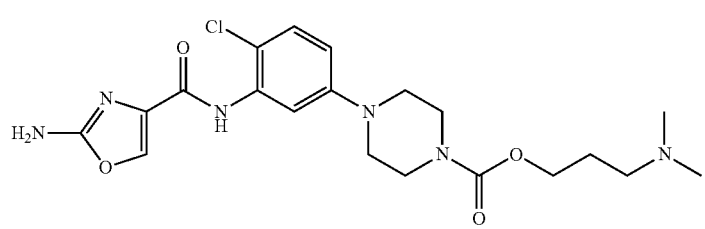 [SMILES: CN(C)CCCOC(=O)N1CCN(c2ccc(Cl)c(NC(=O)c3coc(N)n3)c2)CC1]
29
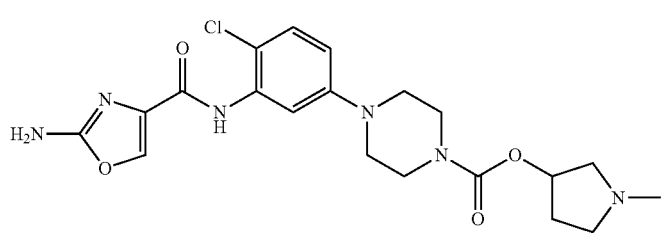 [SMILES: CN1CCC(OC(=O)N2CCN(c3ccc(Cl)c(NC(=O)c4coc(N)n4)c3)CC2)C1]
30
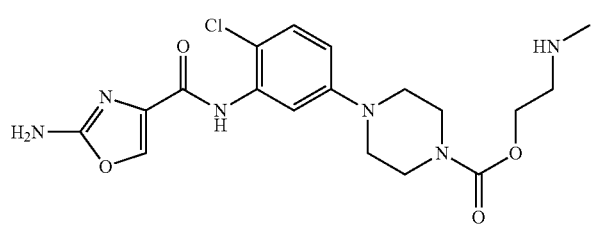 [SMILES: CNCCOC(=O)N1CCN(c2ccc(Cl)c(NC(=O)c3coc(N)n3)c2)CC1]
31
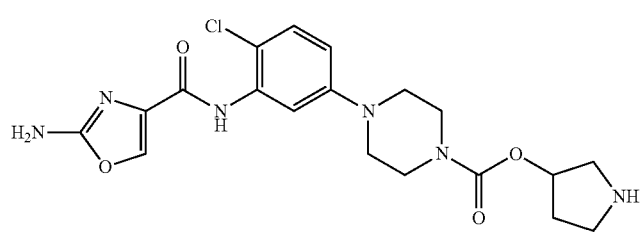 [SMILES: Nc1nc(C(=O)Nc2cc(N3CCN(C(=O)OC4CCNC4)CC3)ccc2Cl)co1]
32

33
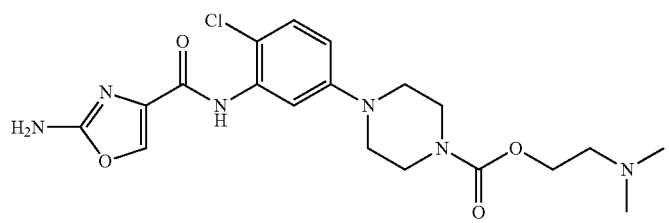 [SMILES: CN(C)CCOC(=O)N1CCN(c2ccc(Cl)c(NC(=O)c3coc(N)n3)c2)CC1]
34
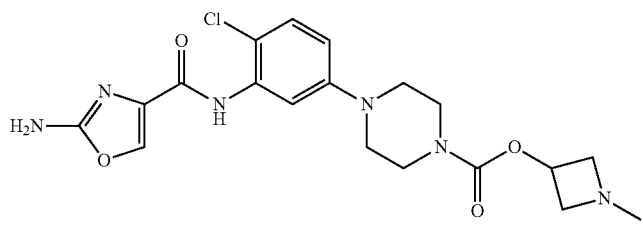 [SMILES: CN1CC(OC(=O)N2CCN(c3ccc(Cl)c(NC(=O)c4coc(N)n4)c3)CC2)C1]
35
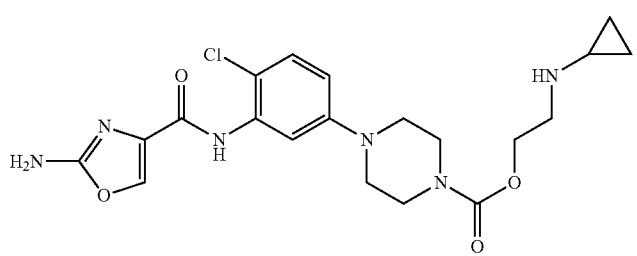 [SMILES: Nc1nc(C(=O)Nc2cc(N3CCN(C(=O)OCCNC4CC4)CC3)ccc2Cl)co1]
44
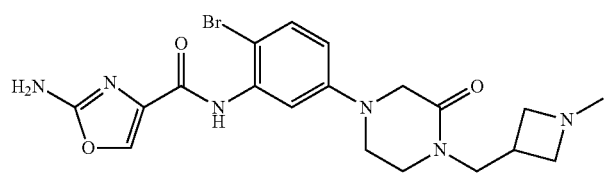 [SMILES: CN1CC(CN2CCN(c3ccc(Br)c(NC(=O)c4coc(N)n4)c3)CC2=O)C1]
45
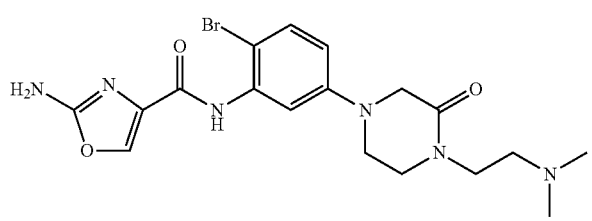 [SMILES: CN(C)CCN1CCN(c2ccc(Br)c(NC(=O)c3coc(N)n3)c2)CC1=O]
46
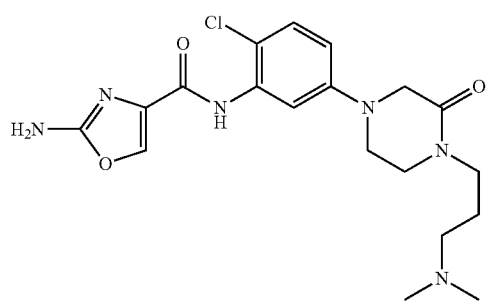 [SMILES: CN(C)CCCN1CCN(c2ccc(Cl)c(NC(=O)c3coc(N)n3)c2)CC1=O]

-continued
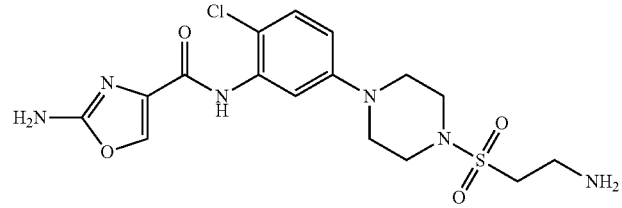 [SMILES: NCCS(=O)(=O)N1CCN(c2ccc(Cl)c(NC(=O)c3coc(N)n3)c2)CC1]
53
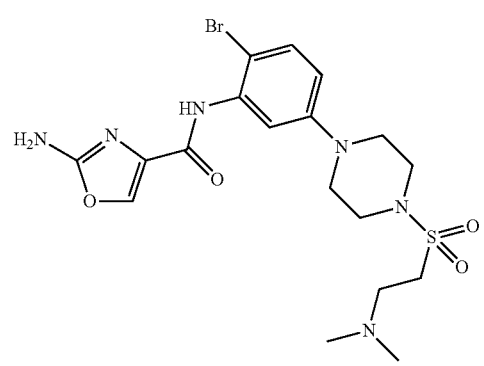
54
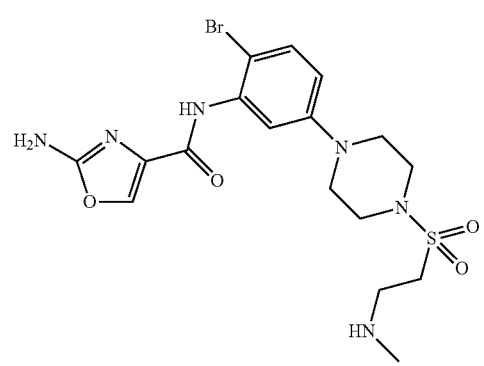 [SMILES: CNCCS(=O)(=O)N1CCN(c2ccc(Br)c(NC(=O)c3coc(N)n3)c2)CC1]
55
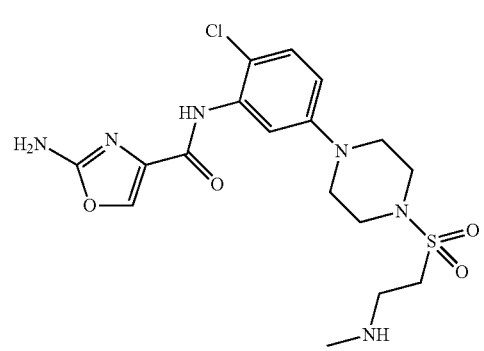 [SMILES: CNCCS(=O)(=O)N1CCN(c2ccc(Cl)c(NC(=O)c3coc(N)n3)c2)CC1]
56

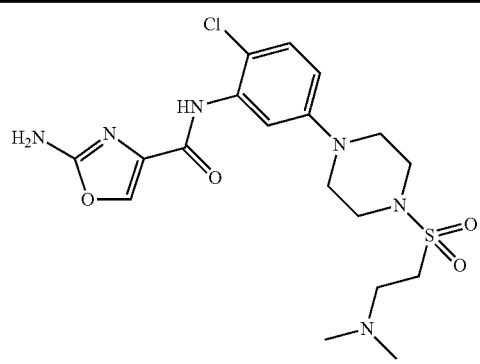
57
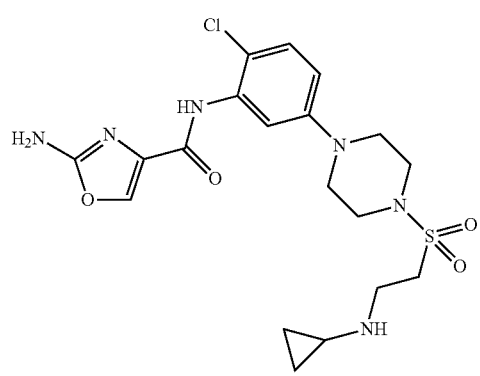 [SMILES: Nc1nc(C(=O)Nc2cc(N3CCN(S(=O)(=O)CCNC4CC4)CC3)ccc2Cl)co1]
58
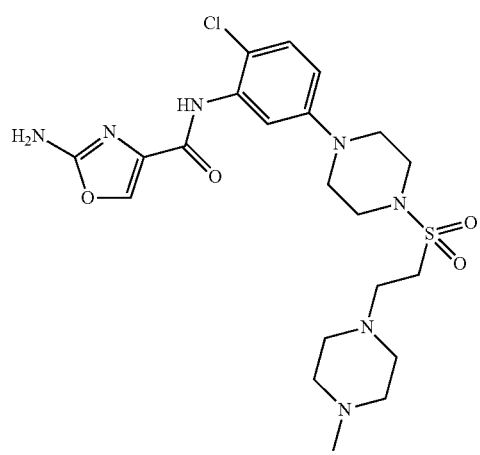 [SMILES: CN1CCN(CCS(=O)(=O)N2CCN(c3ccc(Cl)c(NC(=O)c4coc(N)n4)c3)CC2)CC1]
59
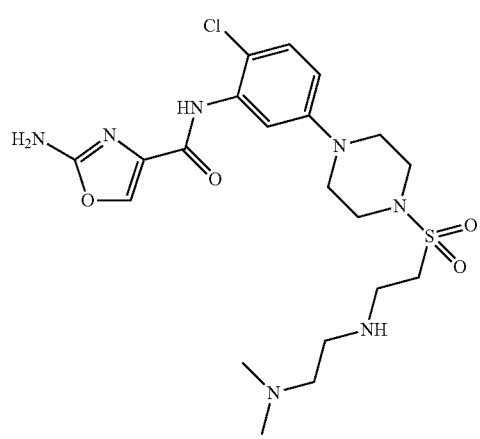 [SMILES: CN(C)CCNCCS(=O)(=O)N1CCN(c2ccc(Cl)c(NC(=O)c3coc(N)n3)c2)CC1]
60

-continued
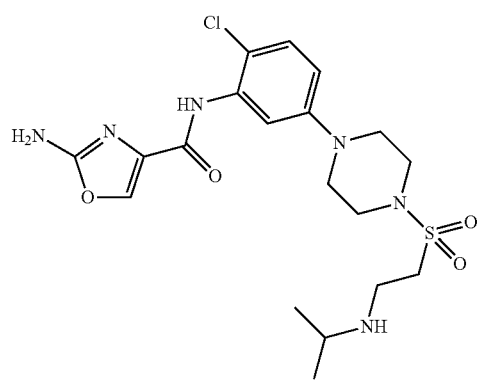 [SMILES: CC(C)NCCS(=O)(=O)N1CCN(c2ccc(Cl)c(NC(=O)c3coc(N)n3)c2)CC1]
61
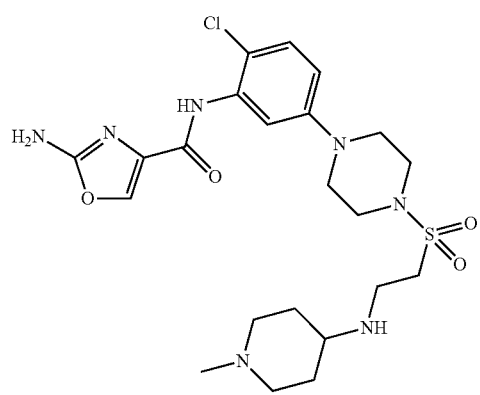 [SMILES: CN1CCC(NCCS(=O)(=O)N2CCN(c3ccc(Cl)c(NC(=O)c4coc(N)n4)c3)CC2)CC1]
62
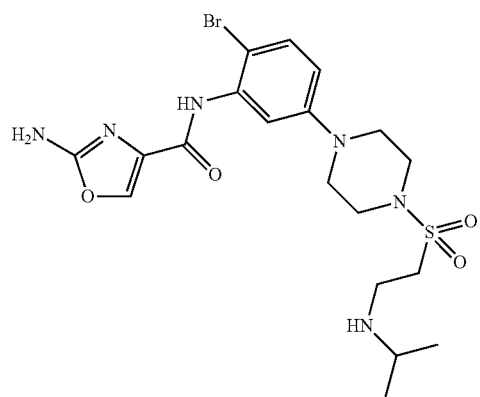 [SMILES: CC(C)NCCS(=O)(=O)N1CCN(c2ccc(Br)c(NC(=O)c3coc(N)n3)c2)CC1]
63

-continued
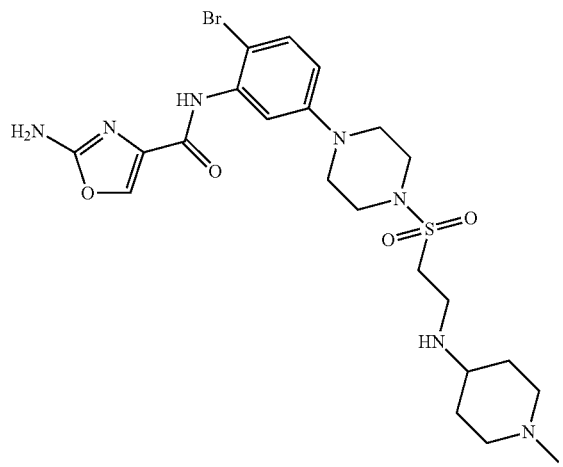 [SMILES: CN1CCC(NCCS(=O)(=O)N2CCN(c3ccc(Br)c(NC(=O)c4coc(N)n4)c3)CC2)CC1]
64
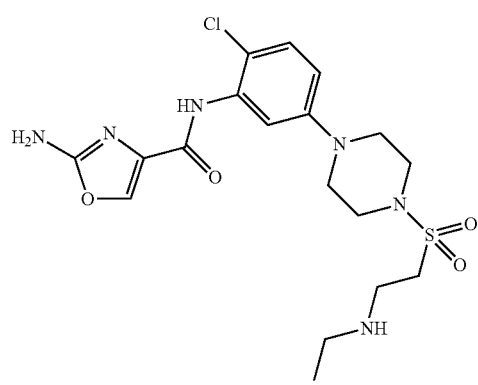 [SMILES: CCNCCS(=O)(=O)N1CCN(c2ccc(Cl)c(NC(=O)c3coc(N)n3)c2)CC1]
65
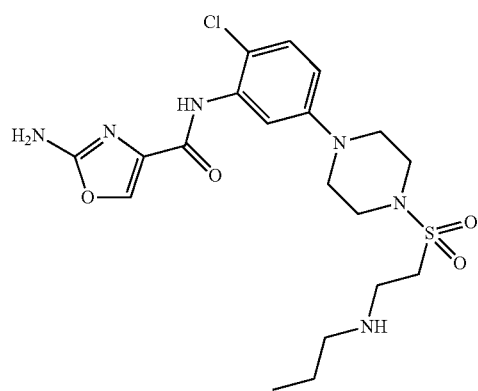 [SMILES: CCCNCCS(=O)(=O)N1CCN(c2ccc(Cl)c(NC(=O)c3coc(N)n3)c2)CC1]
66
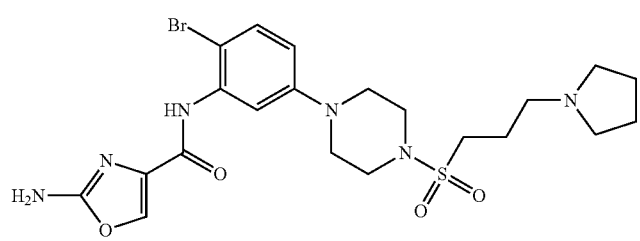 [SMILES: Nc1nc(C(=O)Nc2cc(N3CCN(S(=O)(=O)CCCN4CCCC4)CC3)ccc2Br)co1]
67

-continued
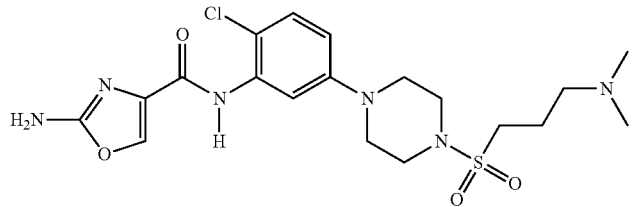 [SMILES: CN(C)CCCS(=O)(=O)N1CCN(c2ccc(Cl)c(NC(=O)c3coc(N)n3)c2)CC1]
68
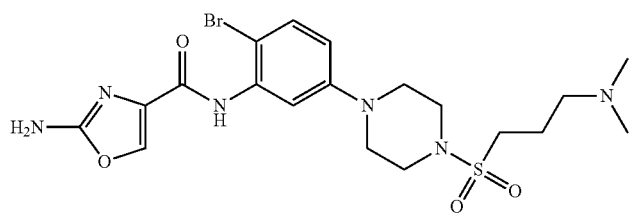 [SMILES: CN(C)CCCS(=O)(=O)N1CCN(c2ccc(Br)c(NC(=O)c3coc(N)n3)c2)CC1]
69
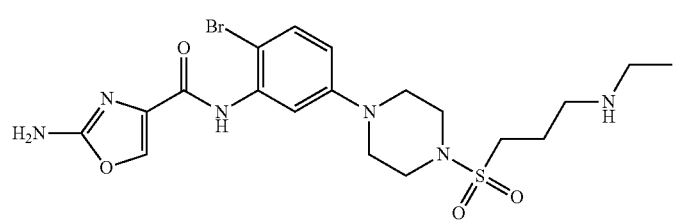
70
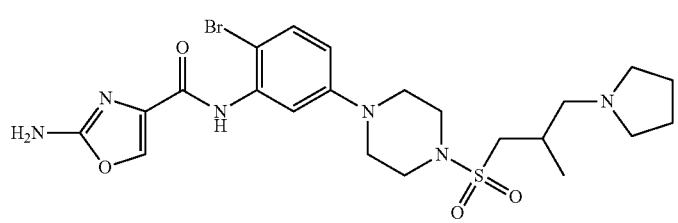 [SMILES: CC(CN1CCCC1)CS(=O)(=O)N1CCN(c2ccc(Br)c(NC(=O)c3coc(N)n3)c2)CC1]
71
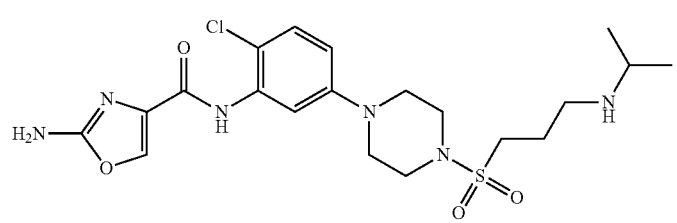 [SMILES: CC(C)NCCCS(=O)(=O)N1CCN(c2ccc(Cl)c(NC(=O)c3coc(N)n3)c2)CC1]
72
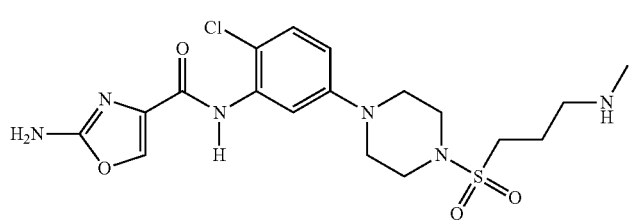 [SMILES: CNCCCS(=O)(=O)N1CCN(c2ccc(Cl)c(NC(=O)c3coc(N)n3)c2)CC1]
73
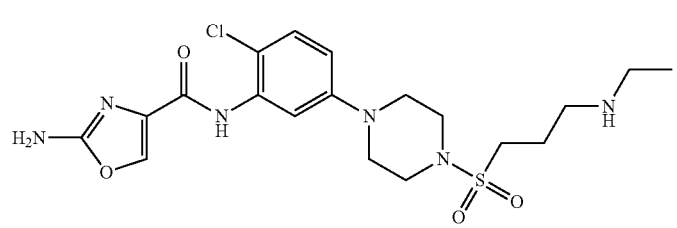 [SMILES: CCNCCCS(=O)(=O)N1CCN(c2ccc(Cl)c(NC(=O)c3coc(N)n3)c2)CC1]
74

-continued
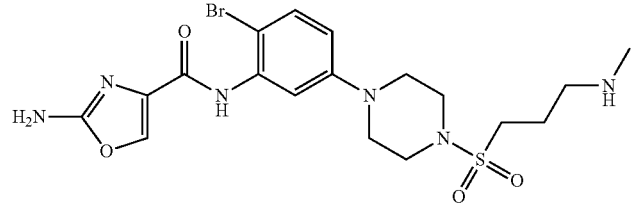
75
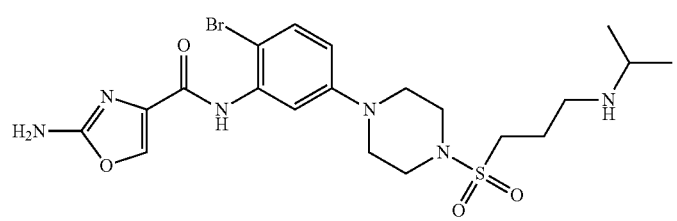 [SMILES: CC(C)NCCCS(=O)(=O)N1CCN(c2ccc(Br)c(NC(=O)c3coc(N)n3)c2)CC1]
76
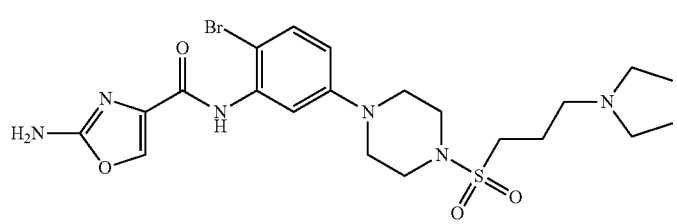 [SMILES: CCN(CC)CCCS(=O)(=O)N1CCN(c2ccc(Br)c(NC(=O)c3coc(N)n3)c2)CC1]
77
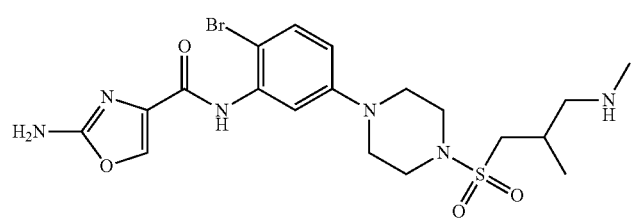
78
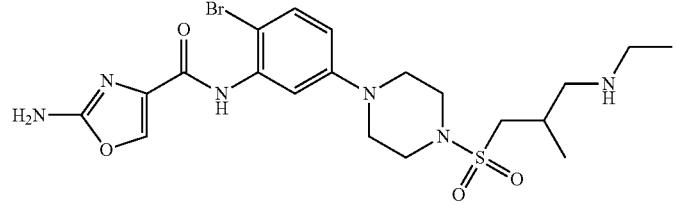 [SMILES: CCNCC(C)CS(=O)(=O)N1CCN(c2ccc(Br)c(NC(=O)c3coc(N)n3)c2)CC1]
79
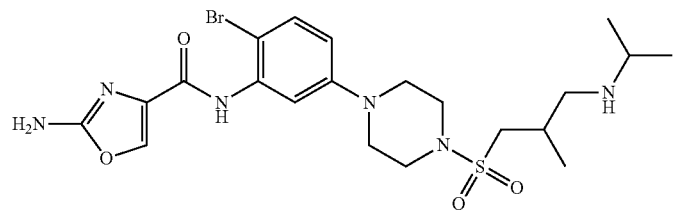 [SMILES: CC(CNC(C)C)CS(=O)(=O)N1CCN(c2ccc(Br)c(NC(=O)c3coc(N)n3)c2)CC1]
80
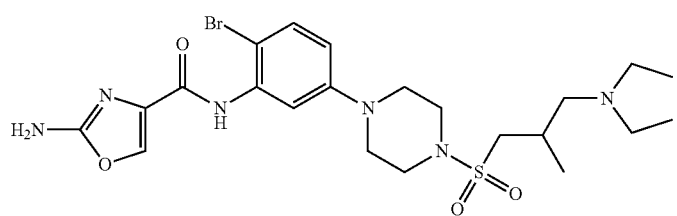 [SMILES: CCN(CC)CC(C)CS(=O)(=O)N1CCN(c2ccc(Br)c(NC(=O)c3coc(N)n3)c2)CC1]
81

-continued
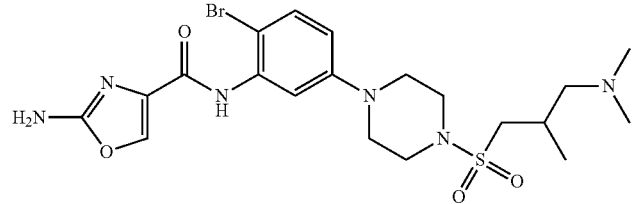 [SMILES: CC(CN(C)C)CS(=O)(=O)N1CCN(c2ccc(Br)c(NC(=O)c3coc(N)n3)c2)CC1]
82
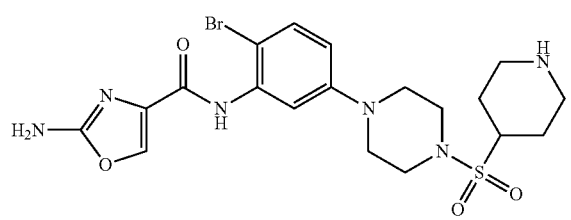 [SMILES: Nc1nc(C(=O)Nc2cc(N3CCN(S(=O)(=O)C4CCNCC4)CC3)ccc2Br)co1]
84
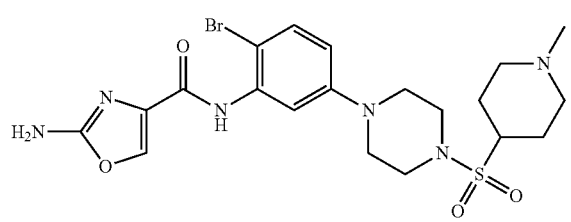 [SMILES: CN1CCC(S(=O)(=O)N2CCN(c3ccc(Br)c(NC(=O)c4coc(N)n4)c3)CC2)CC1]
85
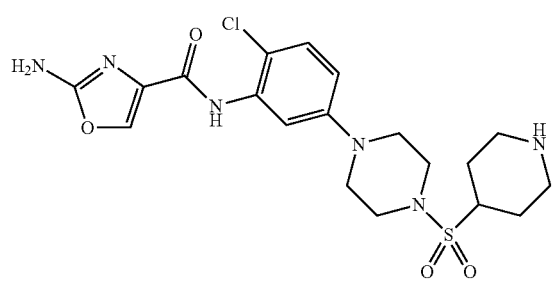 [SMILES: Nc1nc(C(=O)Nc2cc(N3CCN(S(=O)(=O)C4CCNCC4)CC3)ccc2Cl)co1]
86
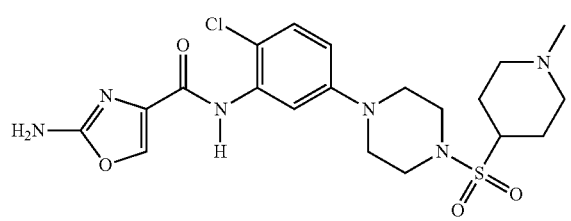 [SMILES: CN1CCC(S(=O)(=O)N2CCN(c3ccc(Cl)c(NC(=O)c4coc(N)n4)c3)CC2)CC1]
87
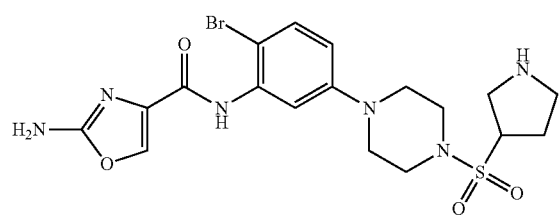 [SMILES: Nc1nc(C(=O)Nc2cc(N3CCN(S(=O)(=O)C4CCNC4)CC3)ccc2Br)co1]
88

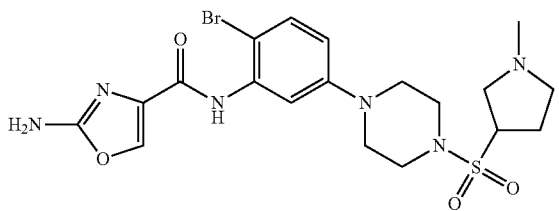 [SMILES: CN1CCC(S(=O)(=O)N2CCN(c3ccc(Br)c(NC(=O)c4coc(N)n4)c3)CC2)C1]

and pharmaceutically acceptable salts and esters thereof.

In one even more highly preferred embodiment, the compound is selected from 21, 23, 24, 25, 54, 55, 67, 69 and 70.

Therapeutic Applications

A further aspect of the invention relates to a compound as described above for use in medicine.

Another aspect of the invention relates to a compound as described above for use in treating a proliferative disorder.

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, antiparasitic disorders such as malaria, emphysema and alopecia. In these disorders, the compounds of the present invention may induce apoptosis or maintain stasis within the desired cells as required.

In one preferred embodiment, the invention relates to a compound as described above for use in preventing or reducing metastasis. Thus, in one preferred embodiment, the compound is for use in preventing or alleviating or treating metastatic cancer, for example, secondary malignant growths at a distance from a primary site of cancer.

In another preferred embodiment, the invention relates to a compound as described above for use in blocking cell growth.

In one preferred embodiment, the proliferative disorder is cancer or leukemia. Preferably, the cancer is selected from solid cancers at any stage. In another preferred embodiment, the cancer is in a late-stage, with metastatic lesions.

Preferably, the cancer is selected from breast cancer, colon cancer, prostate melanoma, bladder, pancreatic, head and neck and ovarian cancer, with or without metastasis, and haematological cancers such as acute myeloid leukemia (AML), chronic lymphocytic leukemia (CLL), acute lymphocytic leukemia (ALL), multiple myeloma (MM) and non-Hodgkins lymphoma.

In one preferred embodiment, the proliferative disorder is selected from breast cancer, colon cancer, lung cancer, melanoma and prostate cancer. Studies by the applicant have demonstrated that PAICS mRNA is upregulated in these tumour types.

In one particularly preferred embodiment, the proliferative disorder is breast cancer. More preferably, the proliferative disorder is metastatic breast cancer or triple negative breast cancer (TNBC). Triple-negative breast cancer refers to any breast cancer that does not express the genes for estrogen receptor (ER), progesterone receptor (PR) or Her2/neu. This makes it more difficult to treat since most chemotherapies target one of the three receptors, so triple-negative cancers often require combination therapies.

Another aspect relates to the use of a compound as described above in the preparation of a medicament for treating or preventing a proliferative disorder, for example, cancer or leukemia.

Another aspect relates to method of treating a proliferative disorder in a subject in need thereof, said method comprising administering to the subject a therapeutically effective amount of a compound as described above.

Preferably, the compound is administered in an amount sufficient to inhibit PAICS.

Another aspect relates to a compound of the invention for use in the prevention or treatment of a disorder caused by, associated with or accompanied by any abnormal activity against a biological target, wherein the target is PAICS.

Yet another aspect relates to the use of a compound of the invention in the preparation of a medicament for the prevention or treatment of a disorder caused by, associated with or accompanied by any abnormal activity against a biological target, wherein the target is PAICS.

Another aspect of the invention relates to a method of treating a PAICS related disease or disorder. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a mammal having a disease state alleviated by inhibition of PAICS, wherein the method comprises administering to a mammal a therapeutically effective amount of a compound according to the invention.

Preferably, the subject is a mammal, more preferably a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and PAICS together in such a manner that the compound can affect the enzyme activity of the PAICS either directly; i.e., by interacting with the PAICS itself or indirectly; i.e., by interacting with another molecule on which the catalytic activity of the PAICS is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl et al, 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "PAICS related disease or disorder" refers to a disease or disorder characterized by inappropriate or abnormal PAICS activity or over-activity. Inappropriate or abnormal activity refers to either; (i) expression in cells which normally do not express the protein; (ii) increased expression leading to unwanted cell proliferation, differentiation and/or growth; or, (iii) decreased expression leading to unwanted reductions in cell proliferation, differentiation and/or growth. Over-activity of PAICS refers to either amplification of the gene encoding PAICS or production of a level of PAICS activity, which can correlate with a cell proliferation, differentiation and/or growth disorder (that is, as the level of the PAICS increases, the severity of one or more of the symptoms of the cellular disorder increases). Over-activity can also be the result of ligand-independent or constitutive activation as a result of mutations such as deletions of a fragment of the protein responsible for ligand binding.

Thus, the present invention further provides use of compounds as defined herein for the manufacture of medicaments for the treatment of diseases where it is desirable to inhibit PAICS. Such diseases include proliferative disorders such as cancer or leukemia.

Pharmaceutical Compositions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy.

All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkled with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulfuric acid, phosphoric acid sulfate, bisulfate, hemisulfate, thiocyanate, persulfate and sulfonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate; organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkane alcohols of 1-12 carbon atoms which may be unsubstituted or substituted, (e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

Isotopic Variations

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^{2}H$, $^{3}H$, $^{13}C$, $^{14}C$, $^{15}N$, $^{17}O$, $^{18}O$, $^{31}P$, $^{32}P$, $^{36}S$, $^{35}S$, $^{18}F$ and $^{30}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include esters (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent Moulded tablets may be made by moulding in a suitable machine a mixture of the powdered compound moistened with an inert liquid diluent. The tablets may be optionally coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formula (I) may be administered to inhibit PAICS. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease or delay the emergence of resistance.

Beneficial combinations may be suggested by studying the inhibitory activity of the test compounds with agents known or suspected of being valuable in the treatment of a particular disorder. For example, the invention relates to the use of a compound as described above in an assay for identifying compounds that promote additive and synergistic activity upon anti-cancer activities when combined with the compound. Preferably the assay is a high-throughput cell based phenotypic screen. This procedure can also be used to determine the order of administration of the agents, i.e. before, simultaneously, or after delivery. Such scheduling may be a feature of all the active agents identified herein.

Assay

A further aspect of the invention relates to the use of a compound as described above in an assay for identifying further candidate compounds capable of inhibiting PAICS. Preferably, the candidate compound is capable of selectively inhibiting PAICS.

Preferably, the assay is a competitive binding assay.

More preferably, the competitive binding assay comprises contacting a compound of the invention with PAICS, and a candidate compound and detecting any change in the interaction between the compound according to the invention and the PAICS. Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high throughput screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a kinase in the presence of a known substrate of said kinase and detecting any change in the interaction between said kinase and said known substrate.

A further aspect of the invention provides a method of detecting the binding of a ligand to PAICS, said method comprising the steps of:
(i) contacting a ligand with PAICS in the presence of a known substrate of said kinase;
(ii) detecting any change in the interaction between said PAICS and said known substrate;
and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of one or more disorders as described hereinabove.

The above methods may be used to screen for a ligand useful as an inhibitor of one or more kinases.

Compounds of general formula (I) are useful both as laboratory tools and as therapeutic agents. In the laboratory certain compounds of the invention are useful in establishing whether a known or newly discovered protein contributes a critical or at least significant biochemical function during the establishment or progression of a disease state, a process commonly referred to as 'target validation'.

Synthesis

Another aspect of the invention relates to a process for preparing a compound of formula (Ib) as defined herein, wherein Y and Z are both N, said process comprising the steps of:

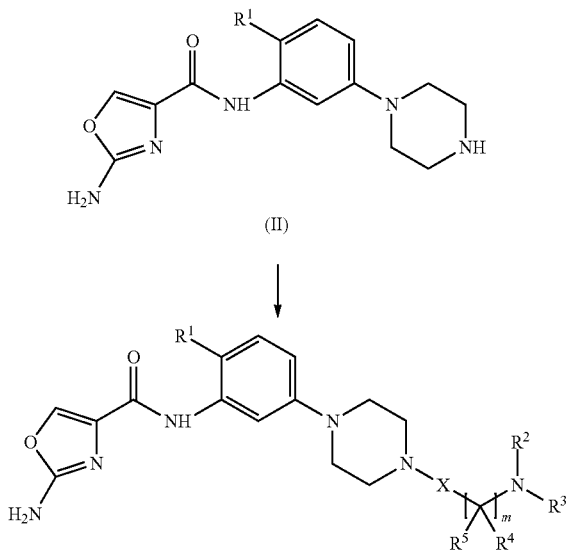

(i) preparing an intermediate of formula (II), where $R^1$ is as defined hereinabove;

(ii) converting said intermediate of formula (II) into a compound of formula (Ib).

The invention is further described by way of the following non-limiting examples, and with reference to the following figures, wherein.

EXAMPLES

Materials and Methods

Chromatography

Figure 1:
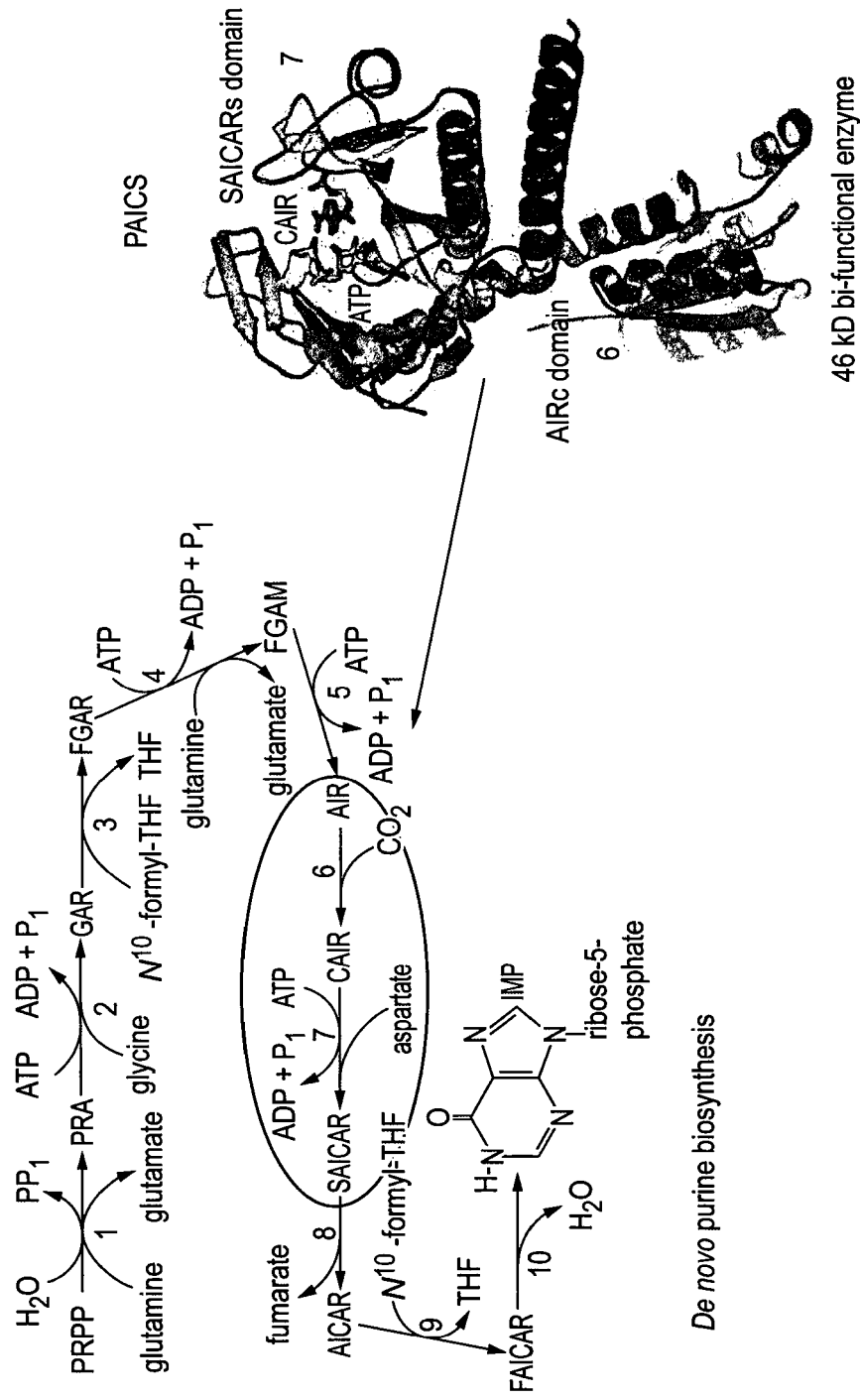
FIG. 1 shows the domains of phosphoribosylaminoimidazole carboxylase, phosphoribosylaminoimidazole succinocarboxamide synthetase, and its role in de novo purine biosynthesis.
Figure 2:
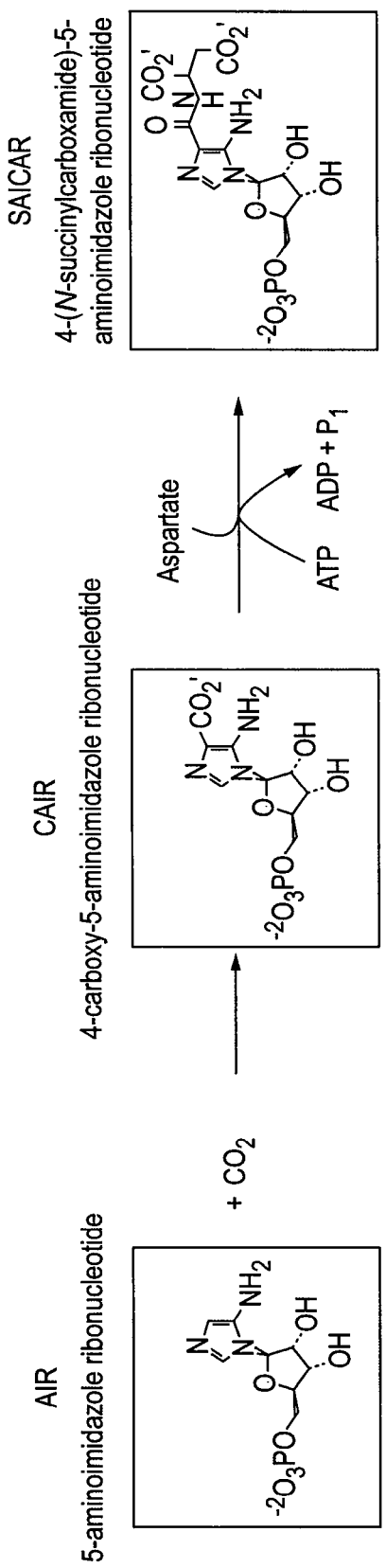
FIG. 2 shows the reaction catalysed by human PAICS.

Preparative high pressure liquid chromatography was carried out using apparatus made by Agilent. The apparatus is constructed such that the chromatography is monitored by a multi-wavelength UV detector (G1365B manufactured by Agilent) and an MM-ES+APCI mass spectrometer (G-1956A, manufactured by Agilent) connected in series, and if the appropriate criteria are met the sample is collected by an automated fraction collector (G1364B manufactured by Agilent). Collection can be triggered by any combination of UV or mass spectrometry or can be based on time. Typical conditions for the separation process are as follows: Chromatography column was an Xbridge C-18 (19×100 mm); the gradient was run over a 7 minute period at a flow rate of 40 ml/min (gradient at start: 10% MeOH and 90% water, gradient at finish: 100% MeOH and 0% water; as buffer either 0.1% formic acid, 0.1% ammonium hydroxide or 0.1% TFA was added to the water). It will be appreciated by those skilled in the art that it may be necessary or desirable to modify the conditions for each specific compound, for example by changing the solvent composition at the start or at the end, modifying the solvents or buffers, changing the run time, changing the flow rate and/or the chromatography column. Flash chromatography refers to silica gel chromatography and was carried out using an SP4 or an Isolera 4 MPLC system (manufactured by Biotage) and pre-packed silica gel cartridges (supplied by Biotage); or alternatively using conventional glass column chromatography.

Analytical Methods $^1$H Nuclear Magnetic Resonance (NMR) spectra were typically recorded using an ECX400 spectrometer (manufactured by JEOL) in the stated solvent at around rt unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; br, broad.

Analytical LCMS was typically carried out using an Agilent HPLC instrument with C-18 Xbridge column (3.5 μm, 4.6×30 mm, gradient at start: 10% organic phase and 90% water, gradient at finish: organic and 0% water; as buffer either 0.1% ammonium hydroxide or 0.1% TFA was added to the water). The organic solvent was either acetonitrile or MeOH. A flow rate of 3 mL/min was used with UV detection at 254 and 210 nm. Mass spectra were recorded using a MM-ES+APCI mass spectrometer (G-1956A, manufactured by Agilent).

Compound Preparation

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

Where reactions are carried out using microwave irradiation, the microwave used is an Initiator 60 supplied by Biotage. The actual power supplied varies during the course of the reaction in order to maintain a constant temperature.

Some hydrogenations were carried out using an H-Cube® Continuous-flow Hydrogenation Reactor manufactured by ThalesNano. The catalysts are supplied by ThalesNano as "CatCarts" cartridges. The pressure, flow rate, temperature and cartridge are indicated in the experimental section. The equipment was used in accordance with the manufacturer operating procedure. The person skilled in the art will appreciate that it may be necessary or desirable to run repeat cycles of the reaction mixture and in some instances, replace the cartridge between cycles to improve the yield of the reaction.

Abbreviations

A list of some common abbreviations is shown below—where other abbreviations are used which are not listed, these will be understood by the person skilled in the art.
AcOH=Acetic acid
BOC=tert-Butyloxycarbonyl
CDI=1,1'-Carbonyldiimidazole
$Cs_2CO_3$=Cesium carbonate
DCM=Dichloromethane
DIPEA=N,N-diisopropylethylamine
DMF=N,N-Dimethytformamide
DMSO=Dimethylsulfoxide
EtOAc=Ethyl acetate
EtOH=Ethanol
HATU=N,N,N',N'-Tetramethyl-O-(7-azabenzotriazol-1-yl) uranium hexafluorophospate
LCMS=Liquid Chromatography Mass Spectrometry
LiCl=Lithium chloride
MeOH=Methanol
$NaHCO_3$=Sodium bicarbonate
$Na_2SO_4$=Sodium sulfate
NMP=N-Methylpyrrolidinone
Pet ether=40l60 petroleum ether
$Pd_2(dba)_3$=tris(dibenzylideneacetone)dipalladium(0)
rt=Room temperature
SCX=Strong cation exchange
TEA=Triethylamine
TFA=Trifluoroacetic acid
THF=Tetrahydrofuran
Xantphos=4,5-Bis(diphenylphosphino)-9,9-dimethylxanthene The synthesis of selected compounds of the invention is described below.

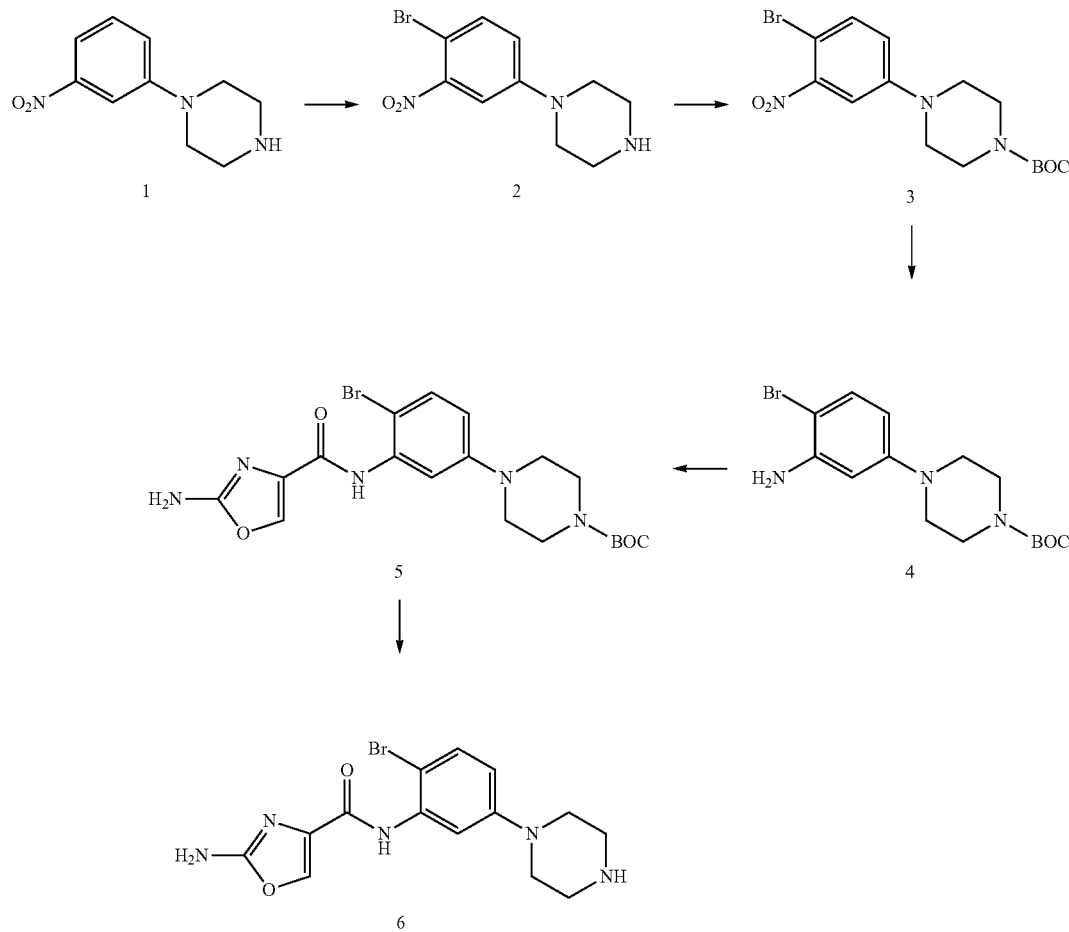

Scheme 1- Preparation of intermediate 6

1-(4-Bromo-3-nitrophenyl)piperazine (2)

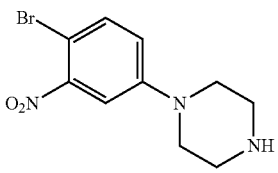 [SMILES: O=[N+]([O-])c1cc(N2CCNCC2)ccc1Br]

To a solution of 1-(3-nitrophenyl)piperazine 1 (4.5 g, 21.7 mmol) in AcOH (100 mL) was added bromine (3.47 g, 21.7 mmol) at rt and stirred for 16 h at 60° C. The reaction mixture was cooled to rt, the precipitated solid was filtered, washed with water (2×50 mL) and dried to obtain compound 2 (4.5 g) as an orange crude solid; LCMS: (m/z)=286/288 [M+H]$^+$. The crude solid was taken as such for next step.

tert-Butyl 4-(4-bromo-3-nitrophenyl)piperazine-1-carboxylate (3)

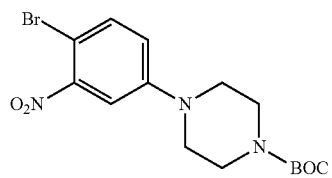 [SMILES: CC(C)(C)OC(=O)N1CCN(c2ccc(Br)c([N+](=O)[O-])c2)CC1]

To a solution of 1-(4-bromo-3-nitrophenyl)piperazine 2 (4.5 g, 15.7 mmol) in DCM (40 mL) was added TEA (4.7 g, 47.2 mmol) followed by di-tert-butyl dicarbonate (5.1 g, 23.6 mmol) at rt and stirred for 16 h. The reaction mixture was concentrated in vacuo. The crude compound was purified by column chromatography (silica gel, 100-200 mesh, eluted with 10% EtOAc/pet ether) to obtain compound 3 (4.5 g, 75%) as a yellow solid; $^1$H NMR (300 MHz, CDCl$_3$) δ ppm 7.54 (d, J=9.3 Hz, 3H), 7.30 (d, J=3.0 Hz, 1H), 6.93 (dd, J=9.3, 3.0 Hz, 1H), 3.61-3.57 (m, 4H), 3.22-3.19 (m, 4H), 1.48 (s, 9H); LCMS: (m/z)=286/288 [(M-BOC)+H]$^+$.

tert-Butyl 4-(3-amino-4-bromophenyl)piperazine-1-carboxylate (4)

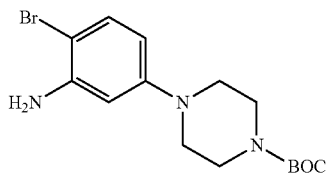

To a solution of tert-butyl 4-(4-bromo-3-nitrophenyl)piperazine-1-carboxylate 3 (4.5 g, 11.6 mmol) in EtOH (40 mL) and water (8 mL) was added iron powder (1.95 g, 35.0 mmol) at rt and heated to 50° C. Then ammonium chloride (3.7 g, 70.0 mmol) was added at 50° C. and continued stirring for 2 h at 70° C. The reaction mixture was cooled to rt and water (20 mL) was added. The mixture was filtered through a pad of celite and the filtrate was extracted with EtOAc (2×40 mL). The combined organic layers were dried (Na$_2$SO$_4$) and concentrated in vacuo. The crude compound was purified by triturating with n-pentane to obtain compound 4 (3.5 g, 85%) as an off white solid; $^1$H NMR (300 MHz, CDCl$_3$) δ ppm 7.25 (d, J=8.7 Hz, 1H), 6.31 (d, J=3.0 Hz, 1H), 6.24 (dd, J=8.7, 3.0 Hz, 1H), 4.10 (br s, 2H), 3.56-3.53 (m, 4H), 3.08-3.05 (m, 4H), 1.48 (s, 9H); LCMS: (m/z)=356/358 [M+H]$^+$.

tert-Butyl 4-(3-(2-aminooxazole-4-carboxamido)-4-bromophenyl)piperazine-1-carboxylate (5)

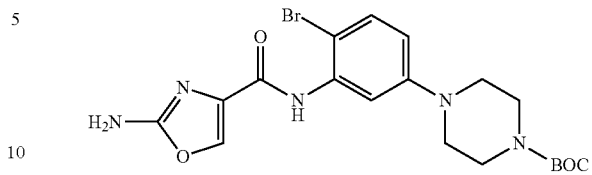

To a solution of tert-butyl 4-(3-amino-4-bromophenyl)piperazine-1-carboxylate 4 (3.5 g, 9.83 mmol) in DMF (20 mL) was added 2-aminooxazole-4-carboxylic acid (5.0 g, 39.3 mmol), HATU (14.9 g, 39.3 mmol) followed by DIPEA (3.8 g, 29.5 mmol) at rt and stirred for 16 h. Ice cold water (50 mL) was added and stirring continued for 10 min. The precipitate was filtered, dried and purified by column chromatography (silica gel, 100-200 mesh, eluted with 50% EtOAc/pet ether) to obtain compound 6 (2.5 g, 55%) as light yellow solid; LCMS: (m/z)=466/468 [M+H]$^+$.

2-Amino-N-(2-bromo-5-(piperazin-1-yl)phenyl)oxazole-4-carboxamide (6)

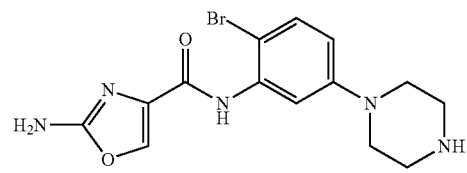 [SMILES: Nc1nc(C(=O)Nc2cc(N3CCNCC3)ccc2Br)co1]

To a solution of tert-butyl 4-(3-(2-aminooxazole-4-carboxamido)-4-bromophenyl)piperazine-1-carboxylate 5 (0.5 g, 1.07 mmol) in DCM (5 mL) was added TFA (5 mL) at rt and the reaction stirred for 2 h. The reaction mixture was concentrated in vacuo, the obtained residue was dissolved in water (10 mL) and basified with saturated NaHCO$_3$ solution. The precipitate was filtered, dried and purified by triturating with saturated NaHCO$_3$ solution to obtain compound 6 (0.32 g, 82%) as an off white solid; $^1$H NMR (300 MHz, DMSO-d$_6$) δ ppm 9.13 (s, 1H), 8.76 (br, s, 1H), 8.06 (s, 1H), 8.01 (d, J=3.0 Hz, 1H), 7.52 (d, J=8.7 Hz, 1H), 7.14 (s, 2H), 6.78 (dd, J=8.7, 3.0 Hz, 1H), 3.34 (br s, 4H), 3.23 (br s, 4H); LCMS: (m/z)=366/368 [M+H]$^+$.

The following intermediate was prepared using analogous procedures:

2-Amino-N-[2-chloro-6-(piperazin-1-yl)phenyl]-1,3-oxazole-4-carboxamide (7)

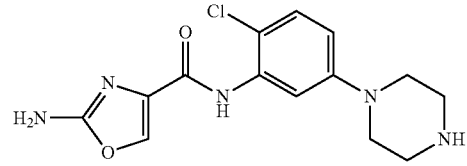 [SMILES: Nc1nc(C(=O)Nc2cc(N3CCNCC3)ccc2Cl)co1]

$^1$H NMR (400 MHz, DMSO-d$_6$) δ ppm 9.13 (s, 1H), 8.06 (s, 1H), 7.98 (d, J=2.9 Hz, 1H), 7.31 (d, J=8.8 Hz, 1H), 7.15 (s, 2H), 6.73 (br dd, J=8.8, 2.4 Hz, 1H), 3.09-3.00 (m, 4H), 2.82 (br s, 4H); LCMS (m/z): 322/324 [M+H]$^+$.

Scheme 2- Preparation of intermediate 12

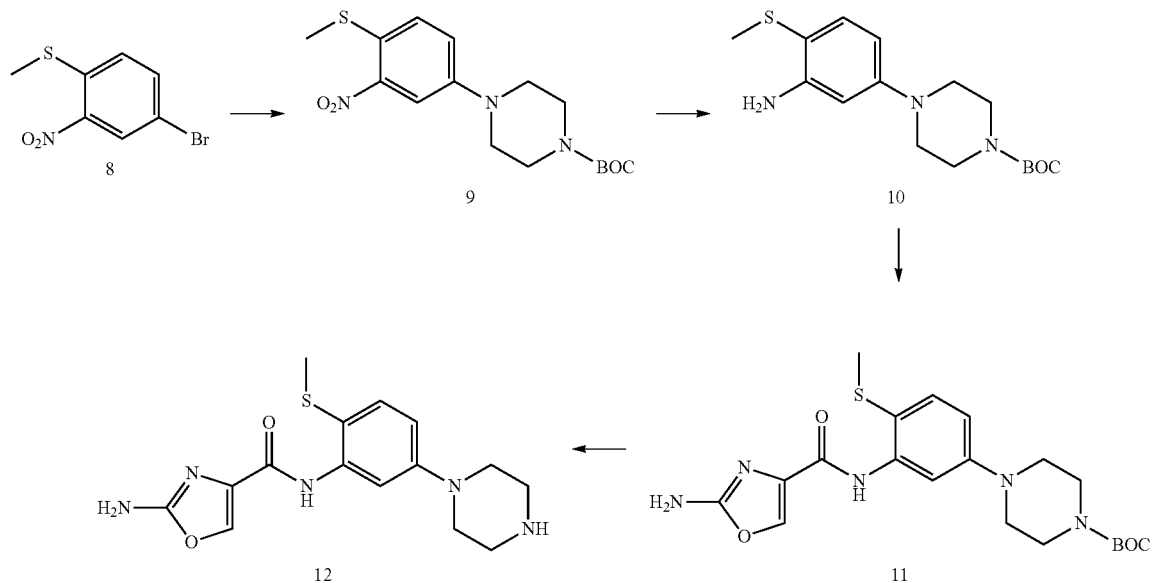

tert-Butyl 4-[4-(methylsulfanyl)-3-nitrophenyl]piperazine-1-carboxylate (9)

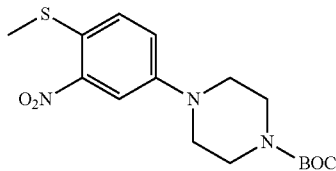 [SMILES: CSc1ccc(N2CCN(C(=O)OC(C)(C)C)CC2)cc1[N+](=O)[O-]]

tert-Butyl piperazine-1-carboxylate (0.56 g, 3.00 mmol), 4-bromo-1-(methylsulfanyl)-2-nitrobenzene 8 (750 mg, 3.00 mmol), palladium (II) acetate (54 mg, 0.24 mmol), Xantphos (210 mg, 0.36 mmol) and $Cs_2CO_3$ (2 g, 6.10 mmol) were combined in DMF (10 mL) and stirred at 110° C. for 3 h. The reaction mixture was filtered through a silica plug, diluted with EtOAc (100 mL), washed with water (3×100 mL) and then saturated LiCl (aq) solution (3×15 mL). The organics were dried, concentrated in vacuo and purified by Biotage Isolera, eluting with 0-14% EtOAc/pet ether to obtain compound 9 (0.78 g, 73%) as an orange solid; $^1$H NMR (400 MHz, DMSO-$d_6$) δ ppm 7.63 (d, J=2.3 Hz, 1H), 7.45-7.39 (m, 2H), 3.50-3.42 (m, 4H), 3.22-3.16 (m, 4H), 2.47 (s, 3H), 1.41 (s, 9H); LCMS (m/z): 354 [M+H]$^+$.

tert-Butyl 4-[3-amino-4-(methylsulfanyl)phenyl]piperazine-1-carboxylate (10)

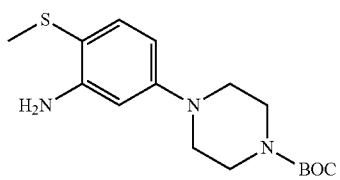 [SMILES: CSc1ccc(N2CCN(C(=O)OC(C)(C)C)CC2)cc1N]

tert-Butyl 4-[4-(methylsulfanyl)-3-nitrophenyl]piperazine-1-carboxylate 9 (550 mg, 1.56 mmol) was dissolved in EtOAc (70 mL) and EtOH (40 mL) and hydrogenated using an H-cube with 10% Pd/C at 30° C. This process was repeated, the eluent concentrated in vacuo, and the residue purified by Isolute-SCX cartridge to obtain compound 10 (510 mg, 100%) as a brown solid; $^1$H NMR (400 MHz, DMSO-$d_6$) δ ppm 7.09 (d, J=8.7 Hz, 1H), 6.28 (d, J=2.5 Hz, 1H), 6.18 (dd, J=8.7, 2.5 Hz, 1H), 5.15 (br s, 2H), 3.46-3.38 (m, 4H), 3.13-2.99 (m, 4H), 2.17 (s, 3H), 1.41 (s, 9H); LCMS (m/z): 324 [M+H]$^+$.

tert-Butyl 4-[3-{[(2-amino-1,3-oxazol-4-yl)carbonyl]amino}-4-(methylsulfanyl)phenyl]piperazine-1-carboxylate (11)

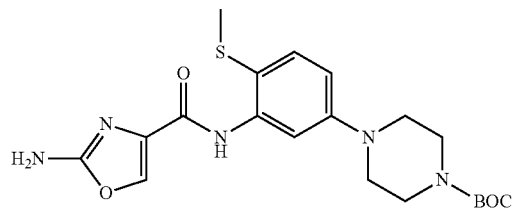 [SMILES: CSc1ccc(N2CCN(C(=O)OC(C)(C)C)CC2)cc1NC(=O)c1coc(N)n1]

2-Amino-1,3-oxazole-4-carboxylic acid (0.27 g, 2.11 mmol), HATU (0.82 g, 2.11 mmol) and DIPEA (2.20 mL, 12.6 mmol) were added to tert-butyl 4-[3-amino-4-(methylsulfanyl)phenyl]piperazine-1-carboxylate 10 (680 mg, 2.11 mmol) in DMF (20 mL) and the reaction mixture was stirred at rt for 18 h. The mixture was partitioned between EtOAc (15 mL) and water (50 mL). The organic layer was washed with water (2×50 mL), saturated LiCl (aq) (3×15 mL), dried, concentrated in vacuo and purified by column chromatography (eluting with 10-100% EtOAc/pet ether) to obtain compound 11 (0.40 g, 44%) as a brown solid; $^1$H NMR (400 MHz, DMSO-$d_6$) δ ppm 9.66 (s, 1H) 8.09 (d, J=2.7 Hz, 1H) 8.04 (s, 1H) 7.42 (d, J=8.7 Hz, 1H) 7.15 (s, 2H) 6.73 (dd, J=8.7, 2.7 Hz, 1H) 3.41-3.50 (m, 4H) 3.09-3.18 (m, 4H) 2.30 (s, 3H) 1.41 (s, 9H); LCMS (m/z): 434 [M+H]$^+$.

2-Amino-N-[2-(methylsulfanyl)-5-(piperazin-1-yl)phenyl]-1,3-oxazole-4-carboxamide (12)

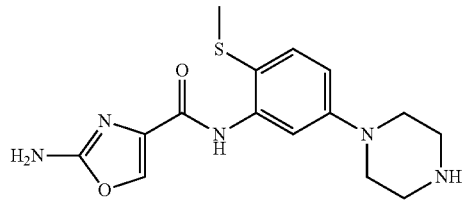 [SMILES: CSc1ccc(N2CCNCC2)cc1NC(=O)c1coc(N)n1]

To a solution of tert-butyl4-[3-{[(2-amino-1,3-oxazol-4-yl)carbonyl]amino}-4-(methylsulfanyl)phenyl]piperazine-1-carboxylate 11 (0.40 g, 0.92 mmol) in DCM (4 mL) was added TFA (4 mL) at rt and the reaction stirred for 2 h. The reaction mixture was concentrated in vacuo, and then purified using an Isolute-SCX cartridge to obtain compound 12 (270 mg, 88%) as an orange solid; $^1$H NMR (400 MHz, DMSO-$d_6$) δ ppm 9.67 (s, 1H), 8.08 (d, J=2.7 Hz, 1H), 8.03 (s, 1H), 7.39 (d, J=8.7 Hz, 1H), 7.15 (s, 2H), 6.69 (dd, J=8.7, 2.7 Hz, 1H), 3.34 (s, 1H), 3.10-3.02 (m, 4H), 2.87-2.76 (m, 4H), 2.29 (s, 3H); LCMS (m/z): 334 [M+H]$^+$.

Scheme 3- Preparation of intermediate 13

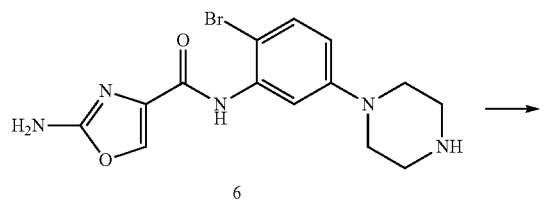

6

↓

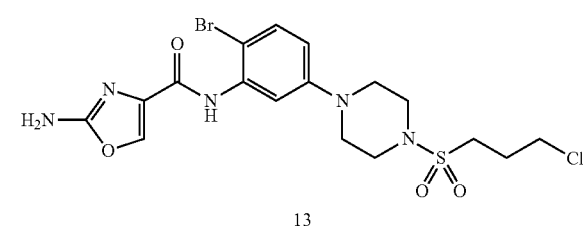

13

2-Amino-N-(2-bromo-5-{4-[(3-chloropropyl)sulfonyl]piperazin-1-yl}phenyl)-1,3-oxazole-4-carboxamide (13)

To a stirred solution of 2-amino-N-(2-bromo-5-(piperazin-1-yl)phenyl)oxazole-4-carboxamide 6 (12 g, 32.9 mmol) in DMF (120 mL) was added 3-chloropropane-1-sulfonyl chloride (7.97 mL, 65.8 mmol), TEA (13.7 mL, 98.0 mmol) at 0° C. and stirred at rt for 6 h. The reaction mixture was poured into cold water (200 mL), filtered the solid and dried to obtain compound 13 (12 g, 72%) as a pale yellow solid; $^1$H NMR (400 MHz, DMSO-$d_6$) δ ppm 9.11 (s, 1H), 8.07 (s, 1H), 7.99 (d, J=2.8 Hz, 1H), 7.91 (s, 1H), 7.49 (d, J=9.2 Hz, 1H), 7.15 (s, 2H), 6.76-6.63 (m, 1H), 3.75 (t, J=6.6 Hz, 2H), 3.34-3.31 (m, 2H), 3.25-3.17 (m, 6H), 3.18-3.11 (m, 2H), 2.18-2.11 (m, 2H); LCMS: (m/z) 506/508/510 [M+H]$^+$.

The following intermediates were prepared using an analogous procedure:

2-Amino-N-(2-chloro-5-{4-[(3-chloropropyl)sulfonyl]piperazin-1-yl}phenyl)-1,3-oxazole-4-carboxamide (14)

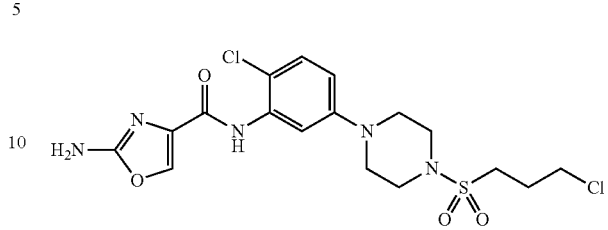

$^1$H NMR (400 MHz, DMSO-$d_6$) δ ppm 9.15 (s, 1H), 8.06 (s, 1H), 8.01 (d, J=3.2 Hz, 1H), 7.36 (d, J=9.2 Hz, 1H), 7.15 (s, 2H), 6.79 (dd, J=9.2, 3.2 Hz, 1H), 3.74 (s, 2H), 3.34-3.30 (m, 4H), 3.26-3.19 (m, 6H), 2.17-2.10 (m, 2H); LCMS: (m/z)=462/464/466 [M+H]$^+$.

2-Amino-N-(2-bromo-5-{4-[(3-chloro-2-methylpropyl)sulfonyl]piperazin-1-yl}phenyl)-1,3-oxazole-4-carboxamide (15)

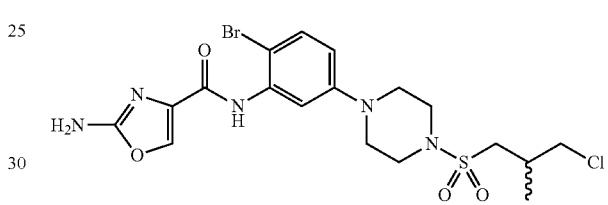

$^1$H NMR (400 MHz, DMSO-$d_6$) δ ppm 9.11 (s, 1H), 8.07 (s, 1H), 7.99 (d, J=3.2 Hz, 1H), 7.49 (d, J=8.9 Hz, 1H), 7.16 (s, 2H), 6.75 (dd, J=8.9, 3.2 Hz, 1H), 3.73 (d, J=5.0 Hz, 2H), 3.33-3.27 (m, 4H), 3.27-3.19 (m, 5H), 3.02 (dd, J=14.2, 7.3 Hz, 1H), 2.45-2.35 (m, 1H), 1.15 (d, J=6.4 Hz, 3H); LCMS (m/z): 520/522 [M+H]$^+$.

Scheme 4- Preparation of intermediate 16

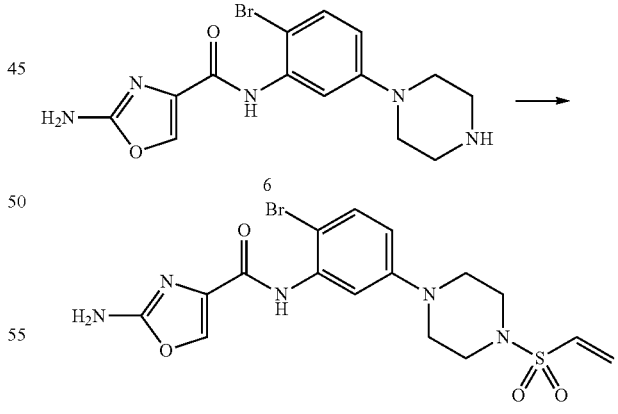

2-Amino-N-{2-bromo-6-[4-(ethenylsulfonyl)piperazin-1-yl]phenyl}-1,3-oxazole-4-carboxamide (16)

2-Amino-N-[2-bromo-5-(piperazin-1-yl)phenyl]-1,3-oxazole-4-carboxamide 6 (1 g, 2.73 mmol) and TEA (1.14 mL, 8.19 mmol) were combined in DMF (10 mL) at 0° C. The reaction was stirred at 0° C. for 5 minutes, then 2-chloroethanesulfonyl chloride (0.28 mL, 2.73 mmol) was added and the reaction mixture was allowed to warm to rt over 5 h. The mixture was then partitioned between EtOAc and saturated LiCl (aq), the organic layer recovered using a phase separation cartridge and concentrated in vacuo. The crude product was purified by column chromatography (eluting with 0-60% EtOAc/pet ether gradient) to give the desired product 16 (0.22 g, 18%); ¹H NMR (400 MHz, DMSO-d₆) δ ppm 9.10 (s, 1H), 8.07 (s, 1H), 7.97 (d, J=3.2 Hz, 1H), 7.49 (d, J=8.7 Hz, 1H), 7.14 (br s, 2H), 6.86 (dd, J=16.5, 10.1 Hz, 1H), 6.74 (dd, J=8.9, 3.0 Hz, 1H), 6.22 (d, J=10.1 Hz, 1H), 6.15 (d, J=16.5 Hz, 1H), 3.28-3.22 (m, 4H), 3.20-3.14 (m, 4H); LCMS: (m/z)=456/458 [M+H]⁺.

The following intermediate was prepared using an analogous procedure:

2-Amino-N-{2-chloro-5-[4-(ethenylsulfonyl)piperazin-1-yl]phenyl}-1,3-oxazole-4-carboxamide (17)

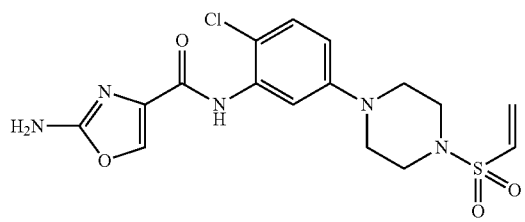 [SMILES: C=CS(=O)(=O)N1CCN(c2ccc(Cl)c(NC(=O)c3coc(N)n3)c2)CC1]

¹H NMR (400 MHz, DMSO-d₆) δ ppm 9.15 (s, 1H), 8.08-8.06 (m, 1H), 7.99 (d, J=2.7 Hz, 1H), 7.35 (d, J=8.9 Hz, 1H), 7.15 (br s, 2H), 6.87 (dd, J=16.5, 10.1 Hz, 1H), 6.79 (dd, J=8.9, 3.0 Hz, 1H), 6.24-6.13 (m, 2H), 3.25 (dd, J=6.2, 3.0 Hz, 4H), 3.21-3.13 (m, 4H); LCMS (m/z): 412/414 [M+H]⁺.

mixture was stirred at rt for 16 h. The reaction mixture was diluted with water (20 mL) and extracted with EtOAc (2×25 mL). The combined organics were washed with brine (10 mL), dried (Na₂SO₄) and concentrated in vacuo. Purification by column chromatography (eluting with 50% EtOAc/pet ether) gave compound 18 (500 mg, 44%) as a brown solid; LCMS (m/z): 535/537 [M+H]⁺. This was re-dissolved in DCM (10 mL), treated with TFA (3 mL) at 0° C., and stirred at rt for 16 h. The reaction mixture was concentrated in vacuo. The obtained residue was basified with saturated NaHCO₃ (aq) solution (10 mL) at 0° C. and extracted with EtOAc (2×50 mL). The combined organics were washed with brine (10 mL), dried (Na₂SO₄) and concentrated in vacuo. DCM (3×5 mL) was added to the residue and the resultant solid was filtered, washed with diethyl ether and dried to obtain 19 (250 mg, 62%) as a brown solid; ¹H NMR (300 MHz, DMSO-d₆) δ ppm 9.14 (s, 1H), 8.06 (s, 1H), 7.99 (m, 1H), 7.34 (d, J=8.7 Hz, 1H), 7.14 (br s, 2H), 6.78 (d, J=6.3 Hz, 1H), 4.11 (d, J=5.7 Hz, 1H), 3.63 (t, J=8.1 Hz, 1H), 3.51 (m, 4H), 3.32 (m, 4H), 3.13 (m, 4H); LCMS (m/z): 435/437 [M+H]⁺.

(1-Methylazetidin-3-yl) methyl 4-(3-(2-aminooxazole-4-carboxamido)-4-chlorophenyl) piperazine-1-carboxylate (20)

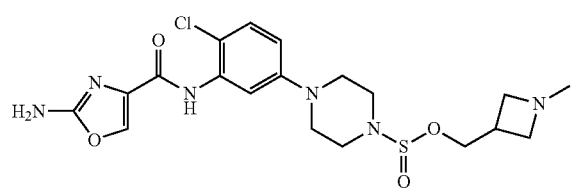 [SMILES: CN1CC(COS(=O)N2CCN(c3ccc(Cl)c(NC(=O)c4coc(N)n4)c3)CC2)C1]

Scheme 5- Preparation of example 20

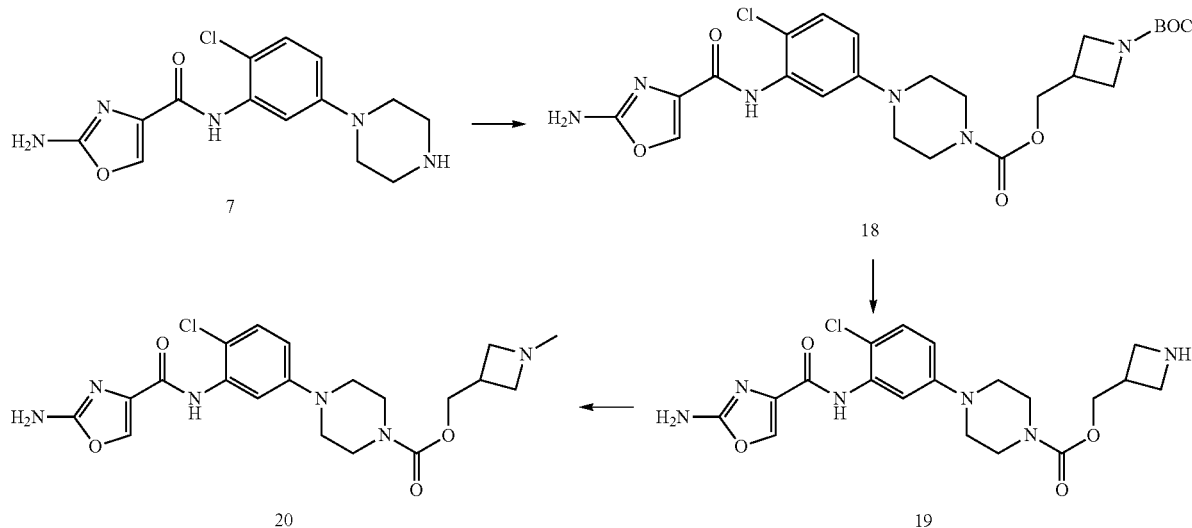

Azetidin-3-ylmethyl 4-(3-(2-aminooxazole-4-carboxamido)-4-chlorophenyl) piperazine-1-carboxylate (19)

To a stirred solution of tert-butyl 3-(hydroxymethyl)azetidine-1-carboxylate (815 mg, 4.35 mmol) in THF (10 mL) was added CDI (1.14 g, 4.35 mmol) at 0° C., and stirred for 30 minutes. 2-Amino-N-[2-chloro-5-(piperazin-1-yl)phenyl]-1,3-oxazole-4-carboxamide 7 (700 mg, 2.18 mmol) and TEA (0.6 mL, 4.35 mmol) were added and the reaction To a stirred solution of azetidin-3-ylmethyl 4-(3-(2-aminooxazole-4-carboxamido)-4-chlorophenyl) piperazine-1-carboxylate 19 (200 mg, 0.46 mmol) in MeOH (5 mL) was added 30% formaldehyde (aq) (20 mg, 0.66 mmol) and zinc chloride (188 mg, 1.38 mmol) at 0° C., and stirred at rt for 2 h. Sodium cyanoborohydride (86 mg, 1.38 mmol) was then added at 0° C., and stirred at rt for 16 h. The reaction mixture was basified with saturated NaHCO₃ (aq) solution (5 mL)

and concentrated in vacuo. The obtained residue was dissolved in MeOH (25 mL) and filtered through Celite and the filtrate was concentrated in vacuo. Purification by preparative HPLC gave 20 (25 mg, 12%) as an off white solid; $^1$H NMR (300 MHz, DMSO-$d_6$) δ ppm 9.14 (s, 1H), 8.06 (s, 1H), 7.99 (d, J=2.8 Hz, 1H), 7.34 (d, J=8.8 Hz, 1H), 7.13 (br s, 2H), 6.78-6.75 (m, 1H), 4.12 (d, J=6.8 Hz, 2H), 3.52 (m, 4H), 3.22 (t, J=7.2 Hz, 2H), 3.13 (m, 4H), 2.87 (t, J=6.4 Hz, 1H), 2.62-2.59 (m, 1H), 2.17 (s, 3H); LCMS (m/z): 449/451 [M+H]$^+$.

The following examples were prepared from intermediates 6, 7 or 12 using analogous procedures:

2-(Cyclopropylamino)ethyl 4-(3-{[(2-amino-1,3-oxazol-4-yl)carbonyl]amino}-4-bromophenyl)piperazine-1-carboxylate (21)

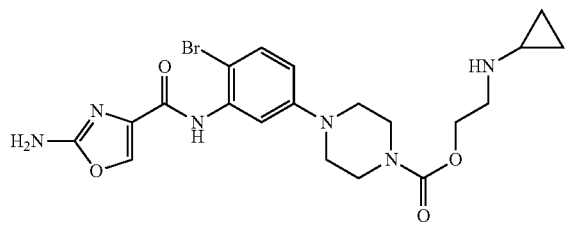 [SMILES: Nc1nc(C(=O)Nc2cc(N3CCN(C(=O)OCCNC4CC4)CC3)ccc2Br)co1]

$^1$H NMR (400 MHz, DMSO-$d_6$) δ ppm 9.10 (s, 1H), 8.06 (s, 1H), 7.98 (d, J=2.9 Hz, 1H), 7.48 (d, J=8.8 Hz, 1H), 7.13 (br s, 2H), 6.73 (dd, J=2.9, 9.3 Hz, 1H), 4.08 (br t, J=5.6 Hz, 2H), 3.52 (br s, 4H), 3.15 (br d, J=4.4 Hz, 4H), 2.85 (br t, J=5.6 Hz, 2H), 2.17 (br s, 1H), 0.40 (br d, J=4.4 Hz, 2H), 0.26 (br s, 2H); LCMS (m/z)=493/495 [M+H]$^+$.

Azetidin-3-yl 4-(3-{[(2-amino-1,3-oxazol-4-yl)carbonyl]amino}-4-chlorophenyl)piperazine-1-carboxylate (22)

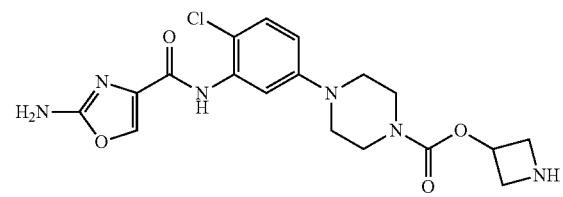 [SMILES: Nc1nc(C(=O)Nc2cc(N3CCN(C(=O)OC4CNC4)CC3)ccc2Cl)co1]

$^1$H NMR (300 MHz, DMSO-$d_6$) δ ppm 9.14 (s, 1H), 8.07 (s, 1H), 8.00 (d, J=2.6 Hz, 1H), 7.35 (d, J=8.8 Hz, 1H), 7.15 (s, 2H), 6.77 (dd, J=2.8, 9.0 Hz, 1H), 5.07 (br s, 1H), 3.65-3.42 (m, 9H), 3.15 (br d, J=4.8 Hz, 4H); LCMS: (m/z)=421/423 [M+H]$^+$.

2-(Dimethylamino)ethyl 4-(3-(2-aminooxazole-4-carboxamido)-4-bromophenyl)piperazine-1-carboxylate (23)

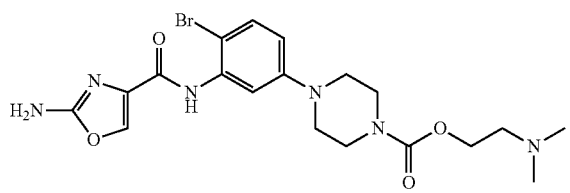 [SMILES: CN(C)CCOC(=O)N1CCN(c2ccc(Br)c(NC(=O)c3coc(N)n3)c2)CC1]

$^1$H NMR (400 MHz, DMSO-$d_6$) δ ppm 9.09 (s, 1H), 8.06 (s, 1H), 7.97 (d, J=2.4 Hz, 1H), 7.46 (d, J=8.8 Hz, 1H), 7.13 (s, 2H), 6.71 (dd, J=8.8, 2.4 Hz, 1H), 4.10 (t, J=5.2 Hz, 2H), 3.50 (br s, 4H), 3.13 (br s, 4H), 2.47 (m, 2H), 2.17 (s, 6H); LCMS: (m/z)=481/483 [M+H]$^+$.

3-(Dimethylamino)propyl 4-(3-(2-aminooxazole-4-carboxamido)-4-bromophenyl)piperazine-1-carboxylate (24)

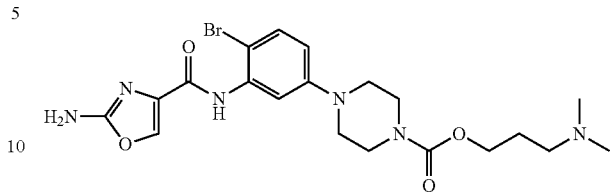

$^1$H NMR (400 MHz, DMSO-$d_6$) δ ppm 9.09 (s, 1H), 8.06 (s, 1H), 7.98 (d, J=3.2 Hz, 1H), 7.47 (d, J=8.8 Hz, 1H), 7.13 (s, 2H), 6.72 (dd, J=2.8, 9.2 Hz, 1H), 4.04 (t, J=6.4 Hz, 2H), 3.51 (br s, 4H), 3.14 (br t, J=4.8 Hz, 4H), 2.26 (t, J=6.8 Hz, 2H), 2.12 (s, 6H), 1.74-1.67 (m, 2H); LCMS: (m/z)=495/497 [M+H]$^+$.

2-(Methylamino)ethyl 4-(3-(2-aminooxazole-4-carboxamido)-4-bromophenyl)piperazine-1-carboxylate (25)

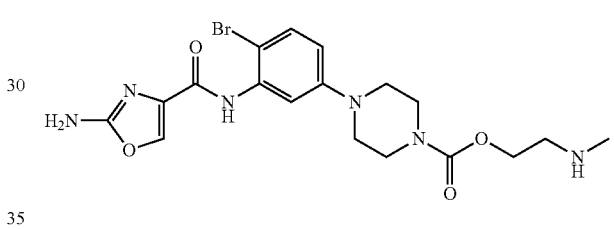

$^1$H NMR (300 MHz, DMSO-$d_6$) δ ppm 9.10 (s, 1H), 8.06 (s, 1H), 7.98 (d, J=2.6 Hz, 1H), 7.47 (d, J=8.8 Hz, 1H), 7.13 (s, 2H), 6.73 (dd, J=9.0, 2.8 Hz, 1H), 4.05 (t, J=5.5 Hz, 2H), 3.52 (br s, 4H), 3.15 (br d, J=4.8 Hz, 4H), 2.69 (t, J=5.7 Hz, 2H), 2.29 (s, 3H); LCMS (m/z)=467/469 [M+H]$^+$.

3-(Dimethylamino)propyl-4-[3-{[(2-amino-1,3-oxazol-4-yl)carbonyl]amino}-4-(methylsulfanyl)phenyl]piperazine-1-carboxylate (26)

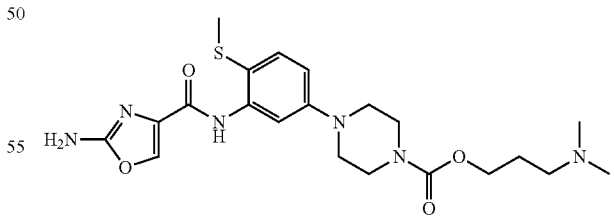

$^1$H NMR (400 MHz, DMSO-$d_6$) δ ppm 9.66 (s, 1H), 8.09 (d, J=2.7 Hz, 1H), 8.04 (s, 1H), 7.43 (d, J=8.7 Hz, 1H), 7.15 (br s, 2H), 6.73 (dd, J=8.7, 2.7 Hz, 1H), 4.04 (t, J=6.6 Hz, 2H), 3.55-3.44 (m, 4H), 3.19-3.12 (m, 4H), 2.43-2.36 (m, 2H), 2.30 (s, 3H), 2.22 (s, 6H), 1.79-1.71 (m, 2H); LCMS (m/z): 463 [M+H]$^+$.

2-(Dimethylamino)ethyl 4-[3-{[(2-amino-1,3-oxazol-4-yl)carbonyl]amino}-4-(methylsulfanyl)phenyl]piperazine-1-carboxylate (27)

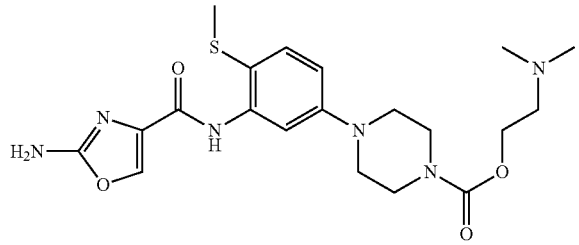 [SMILES: CSc1ccc(N2CCN(C(=O)OCCN(C)C)CC2)cc1NC(=O)c1coc(N)n1]

¹H NMR (400 MHz, DMSO-d₆) δ ppm 9.66 (s, 1H), 8.09 (d, J=2.7 Hz, 1H), 8.04 (s, 1H), 7.43 (d, J=8.7 Hz, 1H), 7.15 (s, 2H), 6.73 (dd, J=8.7, 2.7 Hz, 1H), 4.04 (t, J=6.6 Hz, 2H), 3.55-3.45 (m, 4H), 3.19-3.12 (m, 4H), 2.40 (t, J=7.1 Hz, 2H), 2.30 (s, 3H) 2.22 (s, 6H); LCMS (m/z): 449 [M+H]⁺.

1-Methylazetidin-3-yl 4-(3-{[(2-amino-1,3-oxazol-4-yl)carbonyl]amino}-4-bromophenyl)piperazine-1-carboxylate (28)

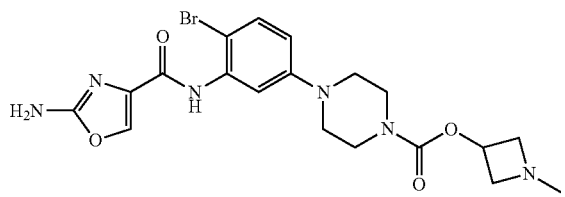 [SMILES: CN1CC(OC(=O)N2CCN(c3ccc(Br)c(NC(=O)c4coc(N)n4)c3)CC2)C1]

¹H NMR (400 MHz, DMSO-d₆) δ ppm 9.10 (s, 1H), 8.06 (s, 1H), 7.97 (d, J=2.9 Hz, 1H), 7.48 (d, J=8.8 Hz, 1H), 7.13 (s, 2H), 6.72 (dd, J=8.8, 2.9 Hz, 1H), 4.83 (quintet, J=5.7 Hz, 1H), 3.58-3.46 (m, 6H), 3.18-3.11 (m, 4H), 2.96-2.90 (m, 2H), 2.24 (s, 3H); LCMS (m/z)=479/481 [M+H]⁺.

3-(Dimethylamino)propyl 4-(3-{[(2-amino-1,3-oxazol-4-yl)carbonyl]amino}-4-chlorophenyl)piperazine-1-carboxylate (29)

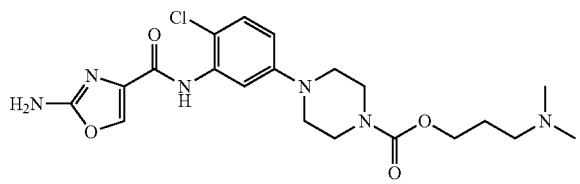 [SMILES: CN(C)CCCOC(=O)N1CCN(c2ccc(Cl)c(NC(=O)c3coc(N)n3)c2)CC1]

¹H NMR (400 MHz, DMSO-d₆) δ ppm 9.14 (s, 1H), 8.07 (s, 1H), 8.00 (d, J=2.9 Hz, 1H), 7.35 (d, J=9.3 Hz, 1H), 7.15 (s, 2H), 6.78 (dd, J=9.0, 2.7 Hz, 1H), 4.05 (t, J=6.6 Hz, 2H), 3.51 (br s, 4H), 3.18-3.10 (m, 4H), 2.34 (br d, J=6.8 Hz, 2H), 2.18 (s, 6H), 1.73 (quintet, J=6.8 Hz, 2H); LCMS: (m/z)= 451/453 [M+H]⁺.

1-Methylpyrrolidin-3-yl 4-(3-{[(2-amino-1,3-oxazol-4-yl)carbonyl]amino}-4-chlorophenyl)piperazine-1-carboxylate (30)

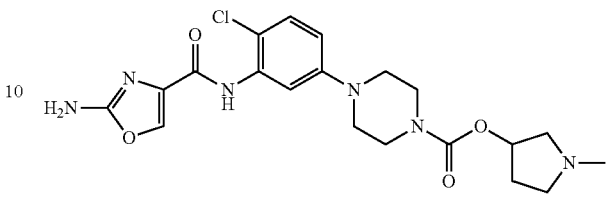

¹H NMR (400 MHz, DMSO-d₆) δ ppm 9.14 (s, 1H), 8.07 (s, 1H), 7.99 (d, J=2.7 Hz, 1H), 7.35 (d, J=9.3 Hz, 1H), 7.14 (br s, 2H), 6.77 (dd, J=8.7, 2.7 Hz, 1H), 5.03-4.99 (m, 1H), 3.51-3.48 (m, 4H), 3.14-3.11 (m, 4H), 2.68-2.48 (m, 3H), 2.28-2.15 (m, 5H), 1.76-1.66 (m, 1H); LCMS (m/z): 449/451 [M+H]⁺.

2-(Methylamino)ethyl 4-(3-{[(2-amino-1,3-oxazol-4-yl)carbonyl]amino}4-chlorophenyl)piperazine-1-carboxylate (31)

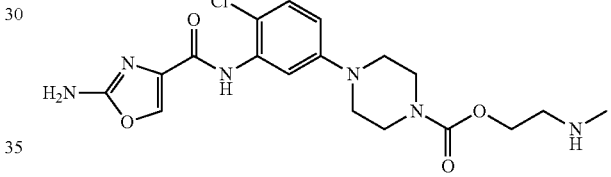

¹H NMR (300 MHz, DMSO-d₆) δ ppm 9.14 (s, 1H), 8.06 (s, 1H), 8.00 (d, J=2.6 Hz, 1H), 7.35 (d, J=9.2 Hz, 1H), 7.14 (s, 2H), 6.77 (dd, J=8.8, 2.9 Hz, 1H), 4.05 (t, J=5.5 Hz, 2H), 3.52 (br s, 4H), 3.17-3.10 (m, 4H), 2.68 (t, J=5.7 Hz, 2H), 2.29 (s, 3H); LCMS (m/z)=423/425 [M+H]⁺.

Pyrrolidin-3-yl 4-(3-{[(2-amino-1,3-oxazol-4-yl)carbonyl]amino}-4-chlorophenyl)piperazine-1-carboxylate (32)

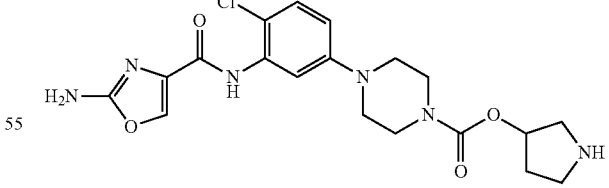

¹H NMR (300 MHz, DMSO-d₆) δ ppm 9.14 (s, 1H), 8.07 (s, 1H), 8.00 (d, J=3.0 Hz, 1H), 7.35 (d, J=9.3 Hz, 1H), 7.15 (s, 2H), 8.77 (dd, J=6.0, 3.0 Hz, 1H), 5.07 (t, J=5.4 Hz, 1H), 3.49 (s, 4H), 3.12 (s, 4H) 2.94-2.80 (m, 2H), 2.75-2.49 (m, 2H), 1.92-1.85 (m, 1H), 1.70-1.66 (m, 1H); LCMS: (m/z)= 435/437 [M+H]⁺.

2-(Dimethylamino)ethyl 4-(3-{[(2-amino-1,3-oxazol-4-yl)carbonyl]amino}-4-chlorophenyl)piperazine-1-carboxylate (33)

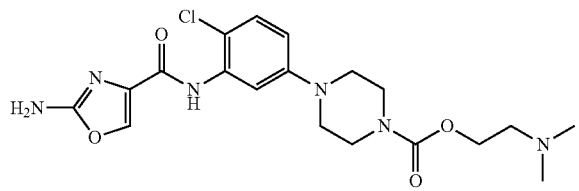 [SMILES: CN(C)CCOC(=O)N1CCN(c2ccc(Cl)c(NC(=O)c3coc(N)n3)c2)CC1]

$^1$H NMR (400 MHz, DMSO-d$_6$) δ ppm 9.14 (s, 1H), 8.07 (s, 1H), 7.99 (d, J=2.9 Hz, 1H), 7.35 (d, J=8.8 Hz, 1H), 7.15 (s, 2H), 6.77 (dd, J=8.8, 2.9 Hz, 1H), 4.10 (t, J=5.9 Hz, 2H), 3.51 (br s, 4H), 3.17-3.09 (m, 4H), 2.47 (br s, 2H), 2.17 (s, 6H); LCMS: (m/z)=437/439 [M+H]$^+$.

1-Methylazetidin-3-yl 4-(3-{[(2-amino-1,3-oxazol-4-yl)carbonyl]amino}-4-chlorophenyl)piperazine-1-carboxylate (34)

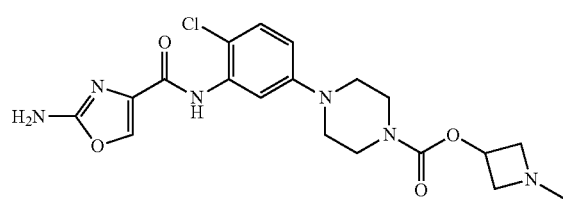

$^1$H NMR (400 MHz, DMSO-d$_6$) δ ppm 9.14 (s, 1H), 8.07 (s, 1H), 7.99 (d, J=2.4 Hz, 1H), 7.35 (d, J=8.8 Hz, 1H), 7.15 (s, 2H), 6.77 (dd, J=8.8, 2.9 Hz, 1H), 4.85-4.82 (m, 1H), 3.56-3.51 (m, 6H), 3.15-3.12 (m, 4H), 2.50-2.49 (m, 2H), 2.24 (s, 3H); LCMS: (m/z)=435/437 [M+H]$^+$.

2-(Cyclopropylamino)ethyl 4-(3-{[(2-amino-1,3-oxazol-4-yl)carbonyl]amino}-4-chlorophenyl)piperazine-1-carboxylate (35)

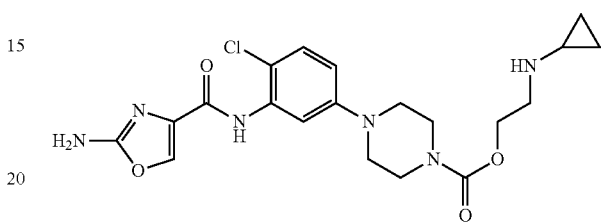

$^1$H NMR (400 MHz, DMSO-d$_6$) δ ppm 9.14 (s, 1H), 8.06 (s, 1H), 8.00 (d, J=2.4 Hz, 1H), 7.35 (d, J=9.3 Hz, 1H), 7.14 (s, 2H), 6.77 (dd, J=9.3, 2.9 Hz, 1H), 4.06 (t, J=5.9 Hz, 2H), 3.52 (br s, 4H), 3.17-3.09 (m, 4H), 2.79 (br t, J=5.6 Hz, 2H), 2.33 (br d, J=1.5 Hz, 1H), 2.10 (tt, J=6.7, 3.5 Hz, 1H), 0.38-0.31 (m, 2H), 0.22-0.15 (m, 2H); LCMS (m/z): 449/451 [M+H]$^+$.

Scheme 6-Preparation of example 44

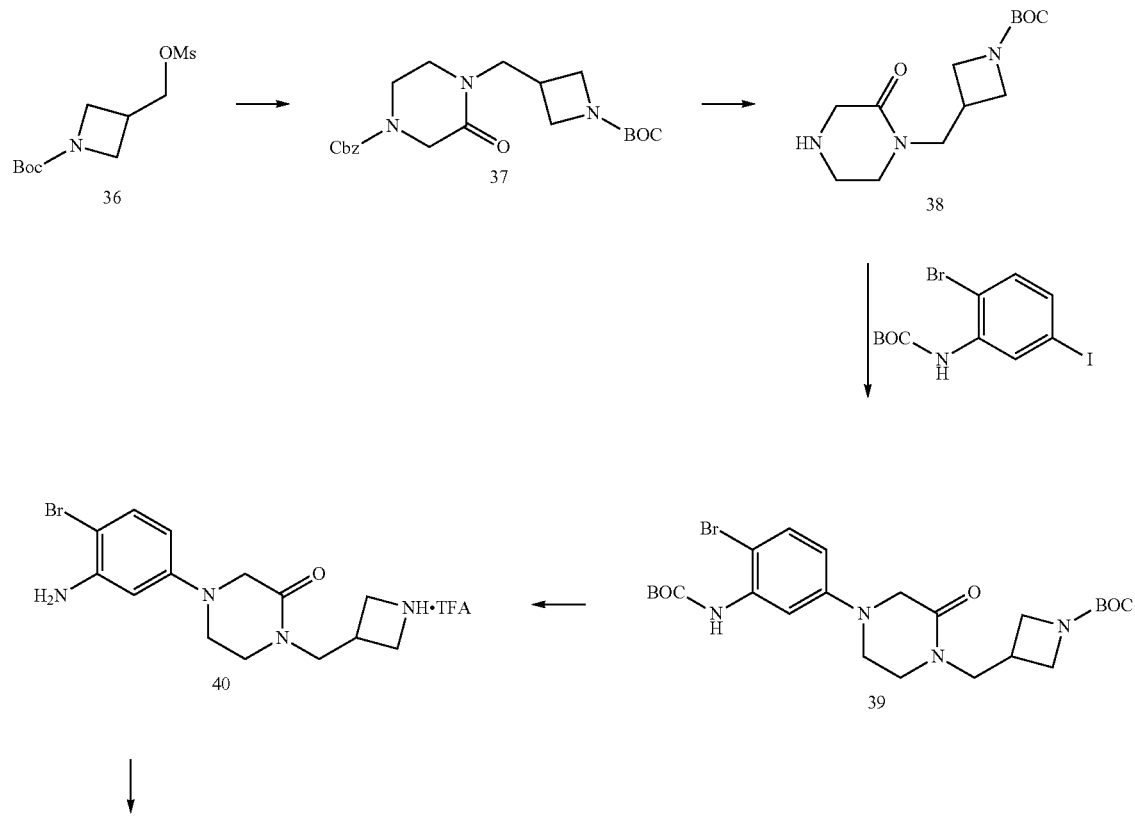

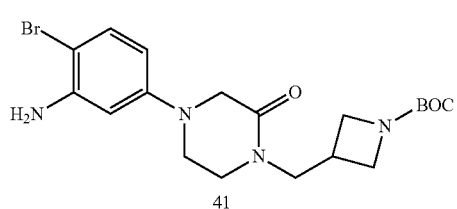

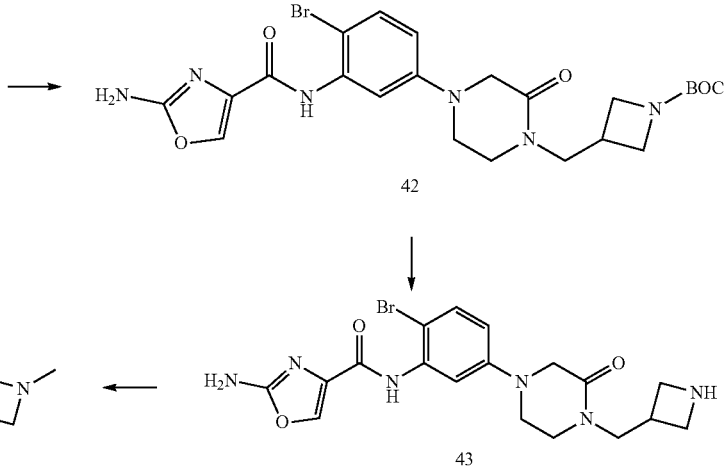

Benzyl 4-((1-(tert-butoxycarbonyl) azetidin-3-yl) methyl)-3-oxopiperazine-1-carboxylate (37)

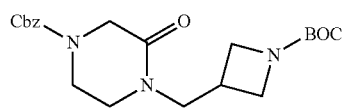 [SMILES: CC(C)(C)OC(=O)N1CC(CN2CCN(C(=O)OCc3ccccc3)CC2=O)C1]

To a solution of benzyl 3-oxopiperazine-1-carboxylate (10 g, 42.7 mmol) in NMP (80 mL) was added 60% sodium hydride (4.25 g, 106 mmol) at 0° C. and stirred for 1 h. Then slowly added a solution of tert-butyl 3-((methylsulfonyloxy) methyl)azetidine-1-carboxylate 36 (16.9 g, 63.8 mmol) in NMP (20 mL) over a period of 15 minutes and stirred 30 minutes at 0° C., then allowed to warm to rt and stirred for 16 h. The reaction mixture was poured into ice water (500 mL) and extracted with EtOAc (2×500 mL). The combined organic layer was washed with brine solution (100 mL), dried (Na$_2$SO$_4$) and concentrated in vacuo. Purification by column chromatography (eluting with 60% EtOAc/pet ether) gave 37 (2.5 g) as a white solid; $^1$H NMR (300 MHz, CDCl$_3$) δ ppm 7.35 (s, 5H), 5.15 (s, 2H), 4.15 (s, 2H), 3.99 (t, J=8.4 Hz, 2H), 3.72-3.64 (m, 6H), 3.35 (m, 2H), 2.90-2.82 (m, 1H), 1.42 (s, 9H); LCMS (m/z): 404 [M+H]$^+$.

tert-Butyl 3-((2-oxopiperazin-1-yl)methyl)azetidine-1-carboxylate (38)

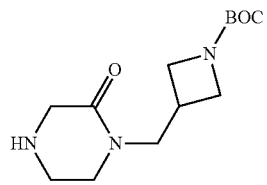 [SMILES: CC(C)(C)OC(=O)N1CC(CN2CCNCC2=O)C1]

To a solution of benzyl 4-((1-(tert-butoxycarbonyl) azetidin-3-yl) methyl)-3-oxopiperazine-1-carboxylate 37 (2.5 g, 6.20 mmol) in MeOH (50 mL) was added 10% Pd/C (500 mg) under N$_2$ atmosphere. The reaction mixture was hydrogenated under a balloon of hydrogen and stirred at rt for 4 h. The reaction mixture was filtered through a Celite pad, washed with MeOH (25 mL) and the filtrate was concentrated in vacuo to obtain compound 38 (1.5 g, 89%) as a black gummy solid; $^1$H NMR (400 MHz, CDCl$_3$) δ ppm 4.00 (t, J=8.4 Hz, 2H), 3.71-3.67 (m, 3H), 3.52 (m, 2H), 3.31 (t, J=5.2 Hz, 2H), 3.07 (t, J=5.2 Hz, 2H), 2.86-2.82 (m, 1H), 1.43 (s, 9H); LCMS (m/z): 270 [M+H]$^+$.

tert-Butyl 3-((4-(4-bromo-3-(tert-butoxycarbonylamino) phenyl)-2-oxopiperazin-1-yl) methyl) azetidine-1-carboxylate (39)

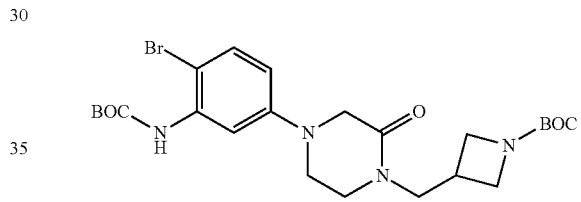

In a sealed tube, to a degassed solution of tert-butyl 2-bromo-5-iodophenylcarbamate (1.0 g, 2.51 mmol) in 1,4-dioxane (15 mL), Cs$_2$CO$_3$ (1.63 g, 5.01 mmol), tort-butyl 3-((2-oxopiperazin-1-yl)methyl)azetidine-1-carboxylate 38 (811 mg, 3.01 mmol) and Xantphos (145 mg, 0.25 mmol) was added Pd$_2$(dba)$_3$ (114 mg, 0.12 mmol) at rt and again degassed for 10 min (argon). The reaction mixture was heated at 100° C. for 16 h. The reaction mixture was cooled to rt, filtered through Celite, washed with EtOAc (50 mL), and the filtrate concentrated in vacuo. Purification by column chromatography (eluting with 60% EtOAc/pet ether gave 39 (800 mg, 59%) as a gummy liquid; $^1$H NMR (400 MHz, CDCl$_3$) δ ppm 7.83 (d, J=2.4 Hz, 1H), 7.35 (d, J=8.8 Hz, 1H), 6.98 (s, 1H), 6.40-6.37 (m, 1H), 4.14 (m, 1H), 4.01 (t, J=8.4 Hz, 2H), 3.99 (s, 2H), 3.72-3.68 (m, 3H), 3.47 (s, 4H), 2.88-2.85 (m, 1H), 1.54 (s, 9H), 1.43 (s, 9H); LCMS (m/z): 539/541 [M+H]$^+$.

tert-Butyl 3-((4-(3-amino-4-bromophenyl)-2-oxopiperazin-1-yl)methyl)azetidine-1-carboxylate (41)

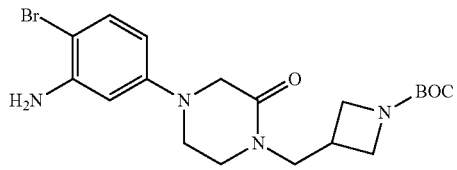 [SMILES: CC(C)(C)OC(=O)N1CC(CN2CCN(c3ccc(Br)c(N)c3)CC2=O)C1]

To a solution of tert-butyl 3-((4-(4-bromo-3-(tert-butoxy-carbonylamino) phenyl)-2-oxopiperazin-1-yl) methyl) azetidine-1-carboxylate 39 (800 mg, 1.48 mmol) in DCM (10 mL) was added TFA (5 mL) at 0° C., and stirred at rt for 16 h. The reaction mixture was concentrated in vacuo to obtain compound 40 as a TFA salt (800 mg, crude) as a gummy liquid.

To a solution of 40 (800 mg, 1.41 mmol) in MeOH (10 mL) was added TEA (0.8 mL 5.65 mmol) and di-tert-butyl dicarbonate (462 mg, 2.12 mmol) at 0° C., and stirred at rt for 16 h. The reaction mixture was concentrated in vacuo, and then purified by column chromatography (eluting with 70% EtOAc/pet ether) to obtain compound 41 (200 mg, 30% over two steps) as a pale yellow solid; $^1$H NMR (400 MHz, DMSO-$d_6$) δ ppm 7.14 (d, J=8.8 Hz, 1H), 6.33 (d, J=4.0 Hz, 1H), 6.14-6.11 (m, 1H), 5.09 (s, 2H), 3.87 (m, 2H), 3.67 (s, 2H), 3.57 (m, 4H), 3.38-3.36 (m, 4H), 2.82-2.72 (m, 1H), 1.37 (s, 9H); LCMS (m/z): 439 [M+H]$^+$.

2-Amino-N-(2-bromo-6-{4-[(1-methylazetidin-3-yl) methyl]-3-oxopiperazin-1-yl}phenyl)-1,3-oxazole-4-carboxamide (44)

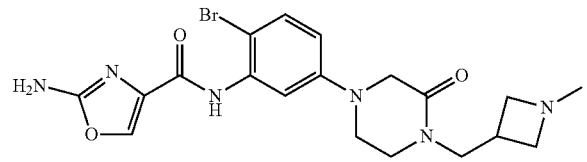 [SMILES: CN1CC(CN2CCN(c3ccc(Br)c(NC(=O)c4coc(N)n4)c3)CC2=O)C1]

tert-Butyl 3-((4-(3-amino-4-bromophenyl)-2-oxopiperazin-1-yl) methyl) azetidine-1-carboxylate 41 (200 mg, 0.45 mmol), 2-aminooxazole-4-carboxylic acid (204 mg, 1.59 mmol), HATU (607 mg, 1.59 mmol) and DIPEA (0.3 mL, 1.59 mmol) were combined in DMF (2 mL) at 0° C. and stirred at rt for 16 h. The reaction mixture was diluted with water (10 mL), the solid filtered, washed with diethyl ether (5 mL) and dried to obtain compound 42 (200 mg, crude) as a brown solid. This was re-dissolved in DCM (3 mL), treated with TFA (1 mL) at 0° C., and stirred at rt for 16 h. The reaction mixture was concentrated in vacuo, the obtained residue was co-distilled with DCM (2×10 mL) and dried to obtain compound 43 (200 mg, crude) as a gummy liquid.

A solution of 43 (200 mg, 0.44 mmol) in MeOH (5 mL) was treated with 30% formaldehyde (aq) (0.08 mL, 0.86 mmol) and sodium acetate (109 mg, 1.32 mmol) at 0° C., and stirred at rt for 1 h. Sodium cyanoborohydride (83 mg, 1.33 mmol) was then added at 0° C., and stirred at rt for 16 h. The reaction mixture was concentrated in vacuo, dissolved in 10% MeOH/DCM (25 mL), filtered and dried. The obtained residue was purified by preparative HPLC to obtain 44 (22 mg, 10% over 3 steps) as a pale yellow solid; $^1$H NMR (300 MHz, DMSO-$d_6$) δ ppm 9.11 (s, 1H), 8.06 (s, 1H), 7.93 (d, J=3.0 Hz, 1H), 7.47 (d, J=8.7 Hz, 1H), 7.14 (s, 2H), 6.69 (dd, J=8.7, 3.0 Hz, 1H), 3.77 (s, 2H), 3.54 (d, J=7.2 Hz, 2H), 3.43 (br s, 4H), 3.22 (t, J=7.2 Hz, 2H), 2.79 (t, J=6.3 Hz, 2H), 2.59-2.54 (m, 1H), 2.15 (s, 3H); LCMS (m/z): 463/465 [M+H]$^+$.

The following examples were prepared using analogous procedures:

2-Amino-N-(2-bromo-6-{4-[2-(dimethylamino)ethyl]-3-oxopiperazin-1-yl}phenyl)-1,3-oxazole-4-carboxamide (45)

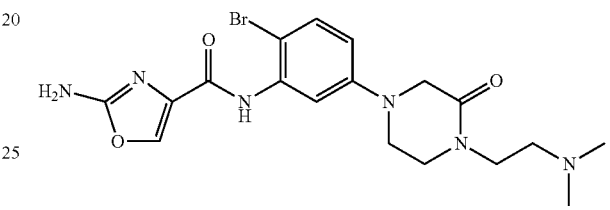

$^1$H NMR (400 MHz, DMSO-$d_6$) δ ppm 9.10 (s, 1H), 8.06 (s, 1H), 7.93 (d, J=2.8 Hz, 1H), 7.47 (d, J=5.2 Hz, 1H), 7.13 (s, 2H), 6.71-6.68 (m, 1H), 3.76 (s, 2H), 3.48-3.44 (m, 6H), 2.39 (t, J=6.4 Hz, 2H), 2.16 (s, 6H); LCMS (m/z): 451/453 [M+H]$^+$.

2-Amino-N-(2-chloro-5-{4-[3-(dimethylamino)propyl]-3-oxopiperazin-1-yl}phenyl)-1,3-oxazole-4-carboxamide (46)

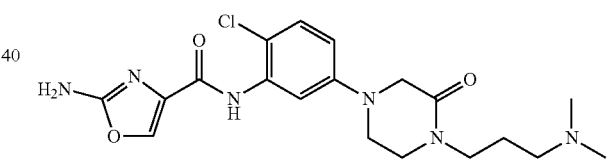

$^1$H NMR (300 MHz, DMSO-$d_6$) δ ppm 9.15 (s, 1H), 8.07 (s, 1H), 7.96 (d, J=3.0 Hz, 1H), 7.35 (d, J=9.3 Hz, 1H), 7.17 (s, 2H), 6.77 (m, 1H), 3.78 (s, 2H), 3.47 (s, 4H), 3.38 (m, 2H), 2.23 (t, J=6.9 Hz, 2H), 2.15 (s, 6H), 1.69-1.62 (m, 2H); LCMS (m/z): 421/423 [M+H]$^+$.

Scheme 7-Preparation of example 53

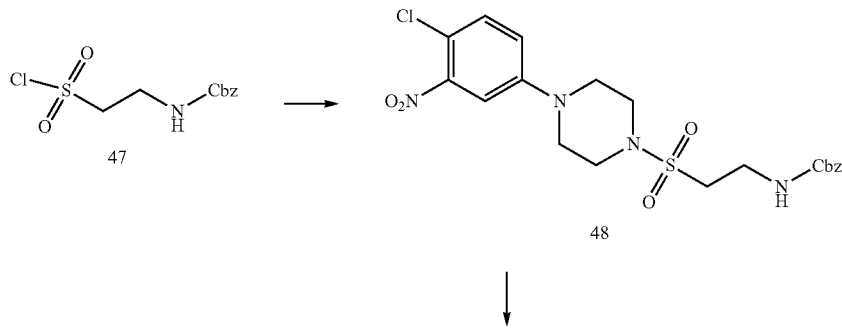

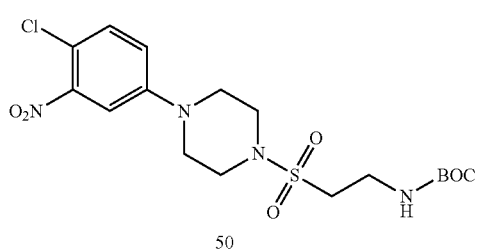

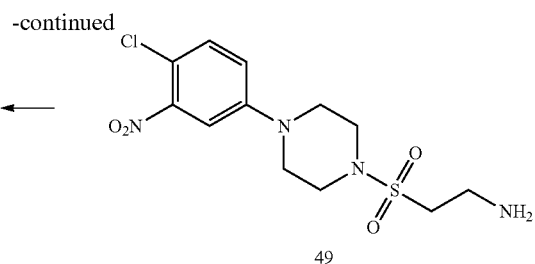

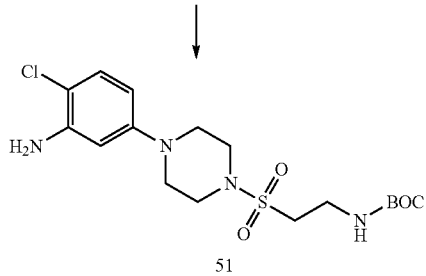

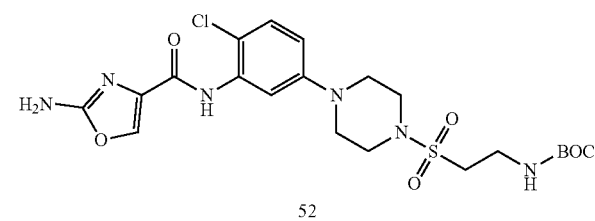

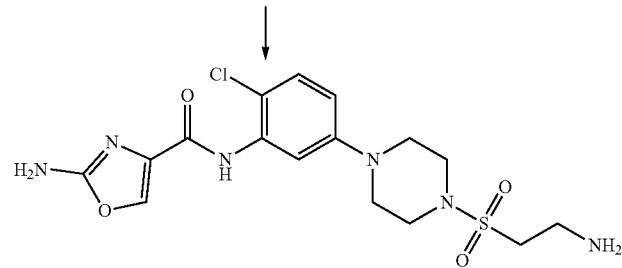

tert-Butyl 2-(4-(4-chloro-3-nitrophenyl)piperazin-1-ylsulfonyl)ethylcarbamate (50)

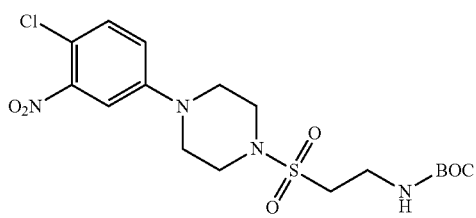

To a solution of 1-(4-chloro-3-nitrophenyl)piperazine (3.0 g, 12.4 mmol) in DCM (20 mL) was added TEA (2.5 g, 24.9 mmol) followed by benzyl 2-(chlorosulfonyl)ethylcarbamate 47 (15 g, crude) at 0° C., and stirred at rt for 16 h. The reaction mixture was diluted with water (100 mL) and extracted with DCM (2×100 mL). The organics were washed with water (2×50 mL), brine (25 mL), dried (Na$_2$SO$_4$) and concentrated in vacuo. Purification by column chromatography (eluting with 30% EtOAc/pet ether) gave compound 48 (2 g) as an impure pale yellow liquid. This was taken to the next step without any purification. A solution of 48 (2 g, 4.14 mmol) in 30% hydrogen bromide in AcOH (6 mL) was stirred at rt for 6 h. The reaction mixture was concentrated in vacuo. The obtained residue was basified with saturated NaHCO$_3$ (aq) (20 mL) and extracted with EtOAc (2×25 mL). The organics were washed with brine (10 mL), dried (Na$_2$SO$_4$) and concentrated in vacuo to obtain the crude product 49 (1 g) as a yellow liquid.

A solution of 49 (1 g, 2.87 mmol) in DCM (20 mL) was treated with TEA (0.8 mL, 5.76 mmol) and di-tert-butyl dicarbonate (689 mg, 3.16 mmol) at 0° C., and stirred at rt for 16 h. The reaction mixture was diluted with water (25 mL) and extracted with DCM (2×50 mL). The organics were washed with brine (25 mL), dried (Na$_2$SO$_4$) and concentrated in vacuo to obtain compound 50 (750 mg, crude) as a yellow liquid; $^1$H NMR (300 MHz, CDCl$_3$) δ ppm 7.40 (d, J=8.8 Hz, 1H), 7.36 (d, J=2.8 Hz, 1H), 7.04-7.01 (m, 1H), 3.61 (t, J=5.6 Hz, 2H), 3.45 (t, J=5.2 Hz, 4H), 3.32 (t, J=5.2 Hz, 4H); 3.16 (t, J=6.0 Hz, 2H), 1.44 (s, 9H); LCMS (m/z): 393[(M−56)+H]$^+$. The crude compound was taken as such for the next step without any purification.

tert-Butyl 2-(4-(3-amino-4-chlorophenyl)piperazin-1-ylsulfonyl)ethylcarbamate (51)

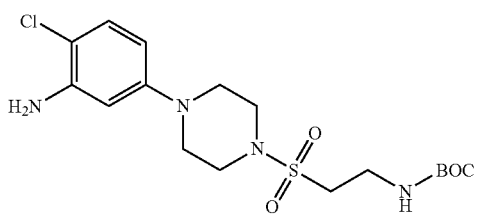 [SMILES: CC(C)(C)OC(=O)NCCS(=O)(=O)N1CCN(c2ccc(Cl)c([N+](=O)[O-])c2)CC1]

tert-Butyl 2-(4-(4-chloro-3-nitrophenyl)piperazin-1-ylsulfonyl)ethylcarbamate 50 (750 mg, 1.67 mmol), NH$_4$Cl (552 mg, 10.0 mmol) and iron (266 mg, 5.01 mmol) were combined in EtOH (15 mL)/H$_2$O (10 mL). The reaction mixture was heated at 80° C. for 6 h, and then allowed to cool, filtered through Celite, washed with MeOH (25 mL), and the filtrate was concentrated in vacuo. The obtained residue was diluted with water (20 mL) and stirred for 10 minutes. Resultant solid was filtered, washed with water and dried in vacuo to obtain compound 51 (300 mg, 43%) as a brown solid; $^1$H NMR (300 MHz, DMSO-$d_6$) δ ppm 7.01-6.95 (m, 2H), 6.38 (d, J=2.4 Hz, 1H), 6.22-6.19 (m, 1H), 5.14 (s, 2H), 3.31-3.25 (m, 6H), 3.20-3.10 (m, 6H), 1.37 (s, 9H); LCMS (m/z): 419/421 [M+H]$^+$.

tert-Butyl2-(4-(3-(2-aminooxazole-4-carboxamido)-4-chlorophenyl)piperazin-1-ylsulfonyl) ethylcarbamate (52)

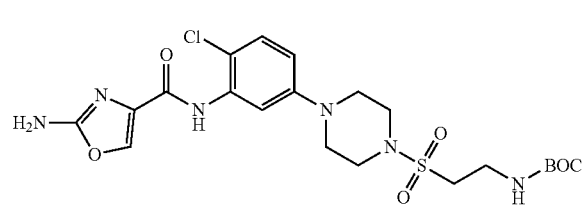 [SMILES: CC(C)(C)OC(=O)NCCS(=O)(=O)N1CCN(c2ccc(Cl)c(NC(=O)c3coc(N)n3)c2)CC1]

To a solution of tert-butyl 2-(4-(3-amino-4-chlorophenyl) piperazin-1-ylsulfonyl)ethylcarbamate 51 (300 mg, 0.717 mmol) in DMF (3 mL) was added 2-aminooxazole-4-carboxylic acid (229 mg, 1.78 mmol), HATU (681 mg, 1.78 mmol) and DIPEA (0.3 mL, 1.79 mmol) at 0° C., and stirred at rt for 16 h. The reaction mixture was diluted with water (10 mL), the solid filtered and dried in vacuo to obtain compound 52 (150 mg, 39%) as a brown solid; $^1$H NMR (300 MHz, DMSO-$d_6$) δ ppm 9.14 (s, 1H), 8.06-8.01 (m, 2H), 7.35 (d, J=9.0 Hz, 1H), 7.14 (s, 2H), 6.96 (m, 1H), 6.81-6.77 (m, 1H), 3.31-3.17 (m, 12H), 1.36 (s, 9H); LCMS (m/z): 529/531 [M+H]$^+$.

2-Amino-N-(5-(4-(2-aminoethylsulfonyl) piperazin-1-yl)-2-chlorophenyl) oxazole-4-carboxamide (53)

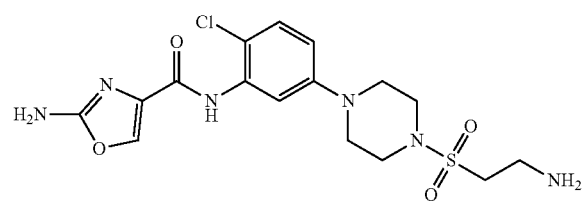 [SMILES: NCCS(=O)(=O)N1CCN(c2ccc(Cl)c(NC(=O)c3coc(N)n3)c2)CC1]

To a solution of tert-butyl 2-(4-(3-(2-aminooxazole-4-carboxamido)-4-chlorophenyl) piperazin-1-ylsulfonyl) ethylcarbamate 52 (150 mg, 0.28 mmol) in DCM (3 mL) was added TFA (1 mL) at 0° C., and then the reaction mixture was stirred at rt for 16 h. The mixture was concentrated in vacuo, basified with saturated NaHCO$_3$ (aq) (5 mL) at 0° C. and stirred for 10 minutes. The resultant solid was filtered, washed with water, MeOH (2 mL), n-pentane (5 mL), and dried in vacuo to obtain 53 (35 mg, 29%) as an off white solid; $^1$H NMR (300 MHz, DMSO-$d_6$) δ ppm 9.15 (s, 1H), 8.06 (s, 1H), 8.01 (d, J=3.0 Hz, 1H) 7.35 (d, J=8.7 Hz, 1H), 7.14 (s, 2H), 6.81-6.77 (m, 1H), 3.31 (m, 4H), 3.23 (d, J=5.4 Hz, 4H), 3.14 (t, J=6.6 Hz, 2H), 2.92 (t, J=6.6 Hz, 2H); LCMS (m/z): 429/431 [M+H]$^+$.

Scheme 8- Preparation of example 54

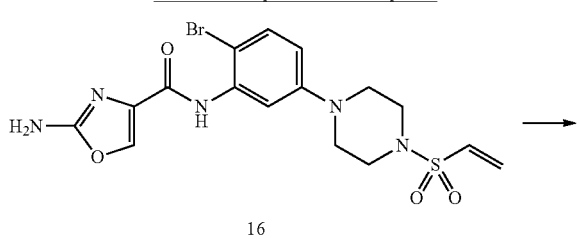

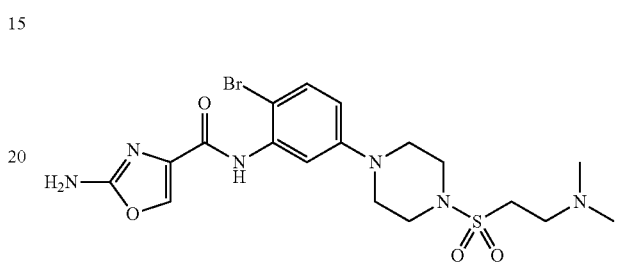

2-Amino-N-[2-bromo-5-(4-{[2-(dimethylamino)ethyl]sulfonyl}piperazin-1-yl)phenyl]-1,3-oxazole-4-carboxamide (54)

2-Amino-N-{2-bromo-5-[4-(ethenylsulfonyl)piperazin-1-yl]phenyl}-1,3-oxazole-4-carboxamide 16 (60 mg, 0.13 mmol) and 2M dimethylamine in THF (1 mL) were combined and irradiated at 100° C. for 30 minutes and then at 120° C. for 30 minutes in a Biotage microwave reactor. Further 2M dimethylamine in THF (0.5 mL) was added and the reaction irradiated at 120° C. for 30 minutes. The reaction mixture was concentrated in vacuo, and then purified by prep. HPLC to obtain compound 54 (5 mg, 8%) as a white solid; $^1$H NMR (400 MHz, DMSO-$d_6$) δ ppm 9.10 (s, 1H), 8.07 (s, 1H), 7.99 (d, J=2.7 Hz, 1H), 7.49 (d, J=8.9 Hz, 1H), 7.15 (s, 2H), 6.75 (dd, J=8.9, 2.7 Hz, 1H), 3.34-3.31 (m, 6H), 3.27-3.20 (m, 4H), 2.65-2.60 (m, 2H), 2.16 (s, 6H); LCMS (m/z): 501/503 [M+H]$^+$.

The following examples were prepared from intermediates 16 or 17 using an analogous procedure:

2-Amino-N-[2-bromo-5-(4-{[2-(methylamino)ethyl]sulfonyl}piperazin-1-yl)phenyl]-1,3-oxazole-4-carboxamide (55)

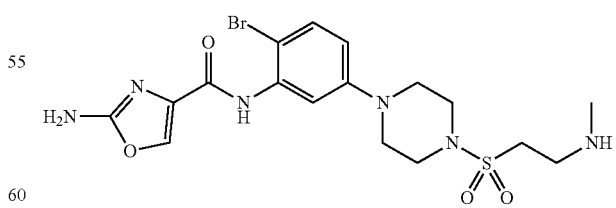

$^1$H NMR (400 MHz, DMSO-$d_6$) δ ppm 9.10 (s, 1H), 8.07 (s, 1H), 7.99 (d, J=3.2 Hz, 1H), 7.49 (d, J=8.9 Hz, 1H), 7.15 (s, 2H), 6.75 (dd, J=8.9, 3.2 Hz, 1H), 3.32-3.29 (m, 5H), 3.27-3.18 (m, 6H), 2.86-2.81 (m, 2H), 2.27 (s, 3H); LCMS: (m/z)=487/489 [M+H]$^+$.

2-Amino-N-[2-chloro-5-(4-{[2-(methylamino)ethyl]sulfonyl}piperazin-1-yl)phenyl]-1,3-oxazole-4-carboxamide (56)

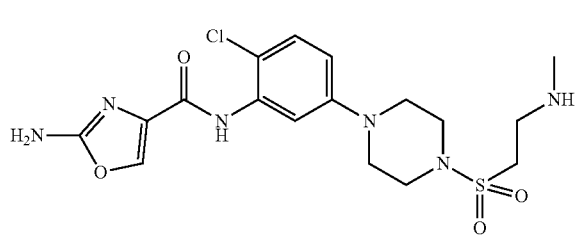 [SMILES: CNCCS(=O)(=O)N1CCN(c2ccc(Cl)c(NC(=O)c3coc(N)n3)c2)CC1]

¹H NMR (400 MHz, DMSO-d₆) δ ppm 9.15 (s, 1H), 8.07 (s, 1H), 8.01 (d, J=2.7 Hz, 1H), 7.36 (d, J=8.7 Hz, 1H), 7.16 (s, 2H), 6.80 (dd, J=8.7, 2.7 Hz, 1H), 3.34-3.30 (m, 5H), 3.26-3.16 (m, 6H), 2.84 (t, J=6.9 Hz, 2H), 2.27 (s, 3H); LCMS (m/z): 443/445 [M+H]⁺.

2-Amino-N-[2-chloro-5-(4-{[2-(dimethylamino)ethyl]sulfonyl}piperazin-1-yl)phenyl]-1,3-oxazole-4-carboxamide (57)

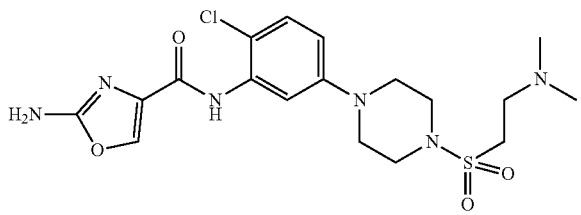 [SMILES: CN(C)CCS(=O)(=O)N1CCN(c2ccc(Cl)c(NC(=O)c3coc(N)n3)c2)CC1]

¹H NMR (400 MHz, DMSO-d₆) δ ppm 9.15 (s, 1H), 8.07 (s, 1H), 8.01 (d, J=2.7 Hz, 1H), 7.35 (d, 0.1=8.9 Hz, 1H), 7.16 (s, 2H), 6.80 (dd, J=8.9, 2.7 Hz, 1H), 3.35-3.29 (m, 6H), 3.28-3.18 (m, 4H), 2.68-2.56 (m, 2H), 2.17 (s, 6H); LCMS (m/z): 457/459 [M+H]⁺.

2-Amino-N-[2-chloro-5-(4-{[2-(cyclopropylamino)ethyl]sulfonyl}piperazin-1-yl)phenyl]-1,3-oxazole-4-carboxamide (58)

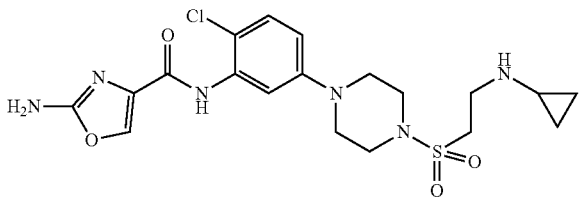 [SMILES: Nc1nc(C(=O)Nc2cc(N3CCN(S(=O)(=O)CCNC4CC4)CC3)ccc2Cl)co1]

¹H NMR (400 MHz, DMSO-d₆) δ ppm 9.15 (s, 1H), 8.07 (s, 1H), 8.01 (d, J=2.7 Hz, 1H), 7.36 (d, J=9.2 Hz, 1H), 7.16 (s, 2H), 6.80 (dd, J=9.2, 2.7 Hz, 1H), 3.36-3.27 (m, 4H), 3.26-3.19 (m, 6H), 3.00-2.90 (m, 2H), 2.39 (br s, 1H), 2.19-2.01 (m, 1H), 0.36 (dd, J=6.9, 4.6 Hz, 2H), 0.21 (dt, J=6.9, 4.6 Hz, 2H); LCMS (m/z): 469/471 [M+H]⁺.

2-Amino-N-[2-chloro-5-(4-{[2-(4-methylpiperazin-1-yl)ethyl]sulfonyl}piperazin-1-yl)phenyl]-1,3-oxazole-4-carboxamide (59)

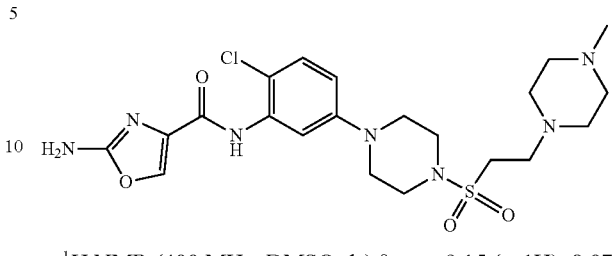

¹H NMR (400 MHz, DMSO-d₆) δ ppm 9.15 (s, 1H), 8.07 (s, 1H), 8.02 (d, J=2.7 Hz, 1H), 7.36 (d, J=8.7 Hz, 1H), 7.16 (s, 2H), 6.79 (dd, J=8.7, 2.7 Hz, 1H), 3.36-3.28 (m, 6H), 3.27-3.24 (m, 4H), 2.65 (t, J=7.1 Hz, 2H), 2.46-2.34 (m, 4H), 2.31-2.18 (m, 4H), 2.09 (s, 3H); LCMS (m/z): 512/514 [M+H]⁺.

2-Amino-N-(2-chloro-5-(4-{[(2-{[2-(dimethylamino)ethyl]amino}ethyl)sulfonyl]piperazin-1-yl}phenyl)-1,3-oxazole-4-carboxamide (60)

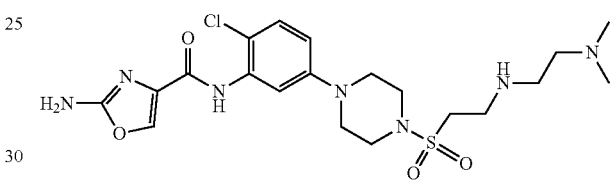

¹H NMR (400 MHz, DMSO-d₆) δ ppm 9.15 (s, 1H), 8.07 (s, 1H), 8.01 (d, J=2.7 Hz, 1H), 7.36 (d, J=8.7 Hz, 1H), 7.16 (s, 2H), 6.79 (dd, J=8.7, 2.7 Hz, 1H), 3.37-3.27 (m, 5H), 3.26-3.19 (m, 6H), 2.92-2.87 (m, 2H), 2.59-2.55 (m, 2H), 2.28-2.24 (m, 2H), 2.11 (s, 6H); LCMS (m/z): 500/502 [M+H]⁺.

2-Amino-N-[2-chloro-5-(4-{[2-(propan-2-ylamino)ethyl]sulfonyl}piperazin-1-yl)phenyl]-1,3-oxazole-4-carboxamide (61)

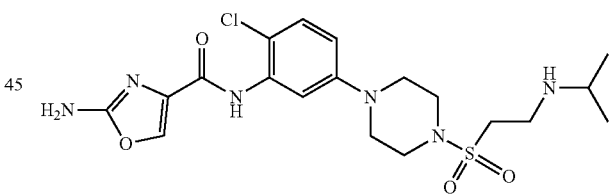

¹H NMR (400 MHz, DMSO-d₆) δ ppm 9.15 (s, 1H), 8.07 (s, 1H), 8.01 (d, J=2.7 Hz, 1H), 7.36 (d, J=8.9 Hz, 1H), 7.16 (s, 2H), 6.79 (dd, J=8.9, 2.7 Hz, 1H), 3.34-3.30 (m, 4H), 3.26-3.16 (m, 6H), 2.90-2.84 (m, 2H), 2.77-2.65 (m, 1H), 1.69 (br s, 1H), 0.95 (d, J=6.4 Hz, 6H); LCMS (m/z): 471/473 [M+H]⁺.

2-Amino-N-{2-chloro-5-[4-({2-[(1-methylpiperidin-4-yl)amino]ethyl}sulfonyl)piperazin-1-yl]phenyl}-1,3-oxazole-4-carboxamide (62)

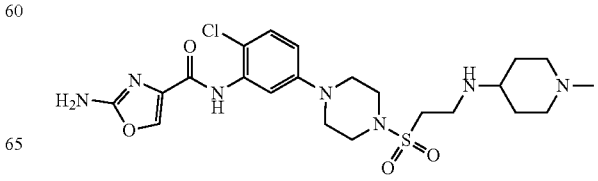

$^1$H NMR (400 MHz, DMSO-d$_6$) δ ppm 9.15 (s, 1H), 8.07 (s, 1H), 8.01 (d, J=2.7 Hz, 1H), 7.36 (d, J=8.9 Hz, 1H), 7.16 (s, 2H), 6.79 (dd, J=8.9, 2.7 Hz, 1H), 3.39-3.28 (m, 4H), 3.28-3.15 (m, 6H), 2.94-2.83 (m, 2H) 2.74-2.60 (m, 2H), 2.41-2.25 (m, 1H), 2.11 (s, 3H), 1.92-1.62 (m, 5H), 1.33-1.00 (m, 2H); LCMS (m/z): 526/528 [M+H]$^+$.

2-Amino-N-[2-bromo-6-(4-{[2-(propan-2-ylamino)ethyl]sulfonyl}piperazin-1-yl)phenyl]-1,3-oxazole-4-carboxamide (63)

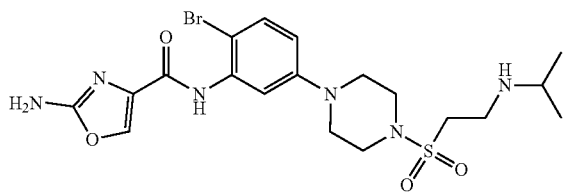

$^1$H NMR (400 MHz, DMSO-d$_6$) δ ppm 9.10 (s, 1H), 8.07 (s, 1H), 7.99 (d, J=3.2 Hz, 1H), 7.49 (d, J=8.9 Hz, 1H), 7.15 (s, 2H), 6.75 (dd, J=8.9, 3.2 Hz, 1H), 3.34-3.30 (m, 4H), 3.26-3.17 (m, 6H), 2.88 (t, J=6.9 Hz, 2H), 2.75-2.67 (m, 1H), 1.80 (br s, 1H), 0.95 (d, J=6.0 Hz, 6H); LCMS (m/z): 515/517 [M+H]$^+$.

2-Amino-N-{2-bromo-5-[4-({2-[(1-methylpiperidin-4-yl)amino]ethyl}sulfonyl)piperazin-1-yl]phenyl}-1,3-oxazole-4-carboxamide (64)

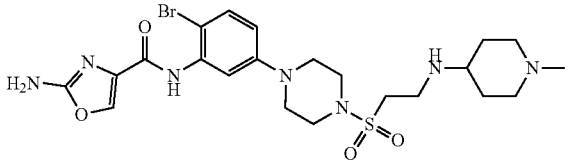

$^1$H NMR (400 MHz, DMSO-d$_6$) δ ppm 9.11 (s, 1H), 7.99 (d, J=2.7 Hz, 1H), 7.48 (d, J=8.9 Hz, 1H), 7.15 (s, 2H), 6.74 (dd, J=8.9, 2.7 Hz, 1H), 3.37-3.27 (m, 4H), 3.27-3.16 (m, 6H), 2.89 (t, J=6.9 Hz, 2H), 2.70-2.61 (m, 2H), 2.38-2.30 (m, 1H), 2.11 (s, 3H), 1.95-1.77 (m, 3H), 1.77-1.66 (m, 2H), 1.24-1.13 (m, 2H); LCMS (m/z): 570/572 [M+H]$^+$.

2-Amino-N-[2-chloro-5-(4-{[2-(ethylamino)ethyl]sulfonyl}piperazin-1-yl)phenyl]-1,3-oxazole-4-carboxamide (65)

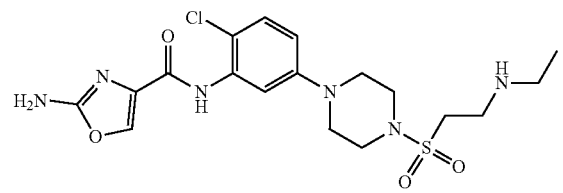

$^1$H NMR (400 MHz, DMSO-d$_6$) δ ppm 9.15 (s, 1H), 8.07 (s, 1H), 8.01 (d, J=2.7 Hz, 1H), 7.36 (d, J=9.2 Hz, 1H), 7.16 (s, 2H), 6.80 (dd, J=9.2, 2.7 Hz, 1H), 3.34-3.31 (m, 4H), 3.26-3.17 (m, 6H), 2.88 (t, J=7.1 Hz, 2H), 2.52 (q, J=7.1 Hz, 2H), 1.82 (br s, 1H), 0.98 (t, J=7.1 Hz, 3H); LCMS (m/z): 457/459 [M+H]$^+$.

2-Amino-N-[2-chloro-5-(4-{[2-(propylamino)ethyl]sulfonyl}piperazin-1-yl)phenyl]-1,3-oxazole-4-carboxamide (66)

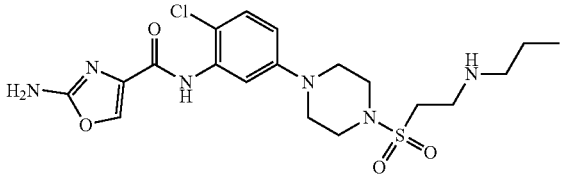

$^1$H NMR (400 MHz, DMSO-d$_6$) δ ppm 9.15 (s, 1H), 8.07 (s, 1H), 8.01 (d, J=2.7 Hz, 1H), 7.36 (d, J=9.2 Hz, 1H), 7.16 (s, 2H), 6.79 (dd, J=9.2, 2.7 Hz, 1H), 3.38-3.29 (m, 4H), 3.27-3.16 (m, 6H), 2.87 (t, J=6.9 Hz, 2H), 2.49-2.42 (m, 3H), 1.45-1.32 (m, 2H), 0.85 (t, J=7.6 Hz, 3H); LCMS (m/z): 471/473 [M+H]$^+$.

Scheme 9 - Preparation of example 67

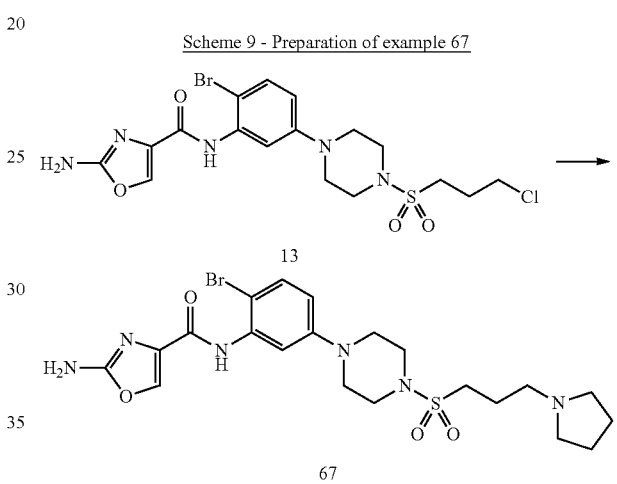

2-Amino-N-[2-bromo-5-(4-{[3-(pyrrolidin-1-yl)propyl]sulfonyl}piperazin-1-yl)phenyl]-1,3-oxazole-4-carboxamide (67)

2-Amino-N-(2-bromo-5-{4-[(3-chloropropyl)sulfonyl]piperazin-1-yl}phenyl)-1,3-oxazole-4-carboxamide 13 (90 mg, 0.18 mmol), sodium iodide (27 mg, 0.18 mmol) and pyrrolidine (44.5 μL, 0.33 mmol) were dissolved in THF (2 mL). The reaction mixture was irradiated at 140° C. for 45 minutes in a Biotage microwave reactor. The mixture was concentrated in vacuo and then purified by preparative HPLC (high pH buffer) to give the product 67 as a white solid (12 mg, 13%); $^1$H NMR (400 MHz, DMSO-d$_6$) δ ppm 9.11 (s, 1H), 8.07 (s, 1H), 7.99 (d, J=3.2 Hz, 1H), 7.49 (d, J=9.2 Hz, 1H), 7.16 (s, 2H), 6.75 (dd, J=9.2, 3.2 Hz, 1H), 3.31 (m, 6H), 3.24 (m, 6H), 3.18-3.11 (m, 4H), 1.95-1.85 (m, 2H), 1.82-1.66 (m, 4H); LCMS: (m/z)=541/543 [M+H]$^+$.

The following examples were prepared from intermediates 13, 14 or 15 using analogous procedures:

2-Amino-N-[2-chloro-5-(4-{[3-(dimethylamino)propyl]sulfonyl}piperazin-1-yl)phenyl]-1,3-oxazole-4-carboxamide (68)

¹H NMR (400 MHz, DMSO-d₆) δ ppm 9.15 (s, 1H), 8.07 (s, 1H), 8.01 (d, J=3.0 Hz, 1H), 7.36 (d, J=9.2 Hz, 1H), 7.17 (s, 2H), 6.80 (dd, J=9.2, 3.0 Hz, 1H), 3.33-3.28 (m, 4H), 3.26-3.20 (m, 2H), 3.12-3.07 (m, 2H), 2.38-2.31 (m, 2H), 2.15 (s, 6H), 1.85-1.78 (m, 2H); LCMS: (m/z)=471/473 [M+H]⁺.

2-Amino-N-(2-bromo-5-(4-(3-(dimethylamino)propylsulfonyl)piperazin-1-yl)phenyl)oxazole-4-carboxamide (69)

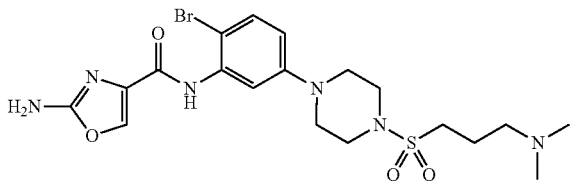 [SMILES: CN(C)CCCS(=O)(=O)N1CCN(c2ccc(Br)c(NC(=O)c3coc(N)n3)c2)CC1]

¹H NMR (400 MHz, DMSO-d₆) δ ppm 9.07 (s, 1H), 8.03 (s, 1H), 7.95 (d, J=2.8 Hz, 1H), 7.45 (d, J=9.2 Hz, 1H), 7.11 (s, 2H), 6.71 (dd, J=8.9, 3.0 Hz, 1H), 3.28-3.23 (m, 7H), 3.23-3.15 (m, 2H), 3.07-3.01 (m, 2H), 2.26 (t, J=6.9 Hz, 2H), 2.10 (s, 6H), 1.80-1.72 (m, 2H); LCMS: (m/z)=515/517 [M+H]⁺.

2-Amino-N-[2-bromo-5-(4-{[3-(ethylamino)propyl]sulfonyl}piperazin-1-yl)phenyl]-1,3-oxazole-4-carboxamide (70)

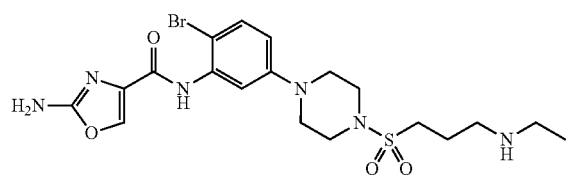 [SMILES: CCNCCCS(=O)(=O)N1CCN(c2ccc(Br)c(NC(=O)c3coc(N)n3)c2)CC1]

¹H NMR (400 MHz, DMSO-d₆) δ ppm 9.11 (br s, 1H), 8.07 (s, 1H), 7.99 (d, J=2.7 Hz, 1H), 7.49 (d, J=9.2 Hz, 1H), 7.16 (s, 2H), 6.75 (dd, J=9.2, 2.7 Hz, 1H), 3.34 (br s, 1H), 3.34-3.27 (m, 4H), 3.26-3.21 (m, 4H), 3.16-3.08 (m, 2H), 2.57 (t, J=6.6 Hz, 2H), 2.54-2.46 (m, 2H), 1.91-1.67 (m, 2H), 0.99 (t, J=7.1 Hz, 3H); LCMS (m/z): 515/517 [M+H]⁺.

2-Amino-N-[2-bromo-5-(4-{[2-methyl-3-(pyrrolidin-1-yl)propyl]sulfonyl}piperazin-1-yl)phenyl]-1,3-oxazole-4-carboxamide (71)

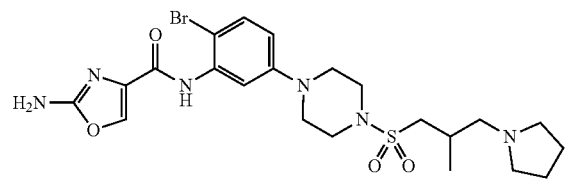 [SMILES: CC(CN1CCCC1)CS(=O)(=O)N1CCN(c2ccc(Br)c(NC(=O)c3coc(N)n3)c2)CC1]

¹H NMR (400 MHz, DMSO-d₆) δ ppm 9.11 (s, 1H), 8.07 (s, 1H), 7.99 (d, J=3.0 Hz, 1H), 7.49 (d, J=9.2 Hz, 1H), 7.16 (s, 2H), 6.75 (dd, J=9.2, 3.0 Hz, 1H), 3.30-3.22 (m, 10H), 2.86 (br s, 2H), 2.47-2.35 (m, 3H), 2.29-2.06 (m, 2H), 1.69 (br s, 4H), 1.13-1.05 (m, 3H); LCMS (m/z): 555/557 [M+H]⁺.

2-Amino-N-[2-chloro-5-(4-{[3-(propan-2-ylamino)propyl]sulfonyl}piperazin-1-yl)phenyl]-1,3-oxazole-4-carboxamide (72)

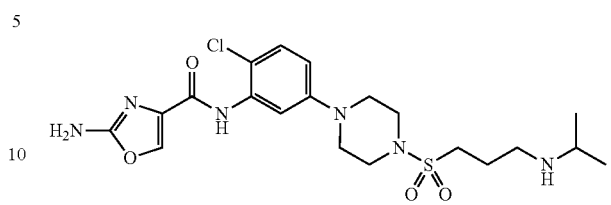

¹H NMR (400 MHz, DMSO-d₆) δ ppm 9.15 (s, 1H), 8.07 (s, 1H), 8.01 (d, J=3.0 Hz, 1H), 7.36 (d, J=8.9 Hz, 1H), 7.16 (s, 2H), 6.80 (dd, J=8.9, 3.0 Hz, 1H), 3.30 (s, 4H), 3.26-3.20 (m, 4H), 3.17-3.09 (m, 2H), 2.67-2.61 (m, 1H), 2.57 (t, J=6.9 Hz, 2H), 1.81-1.74 (m, 2H), 1.56 (br s, 1H), 0.94 (d, J=6.0 Hz, 6H); LCMS (m/z): 485/487 [M+H]⁺.

2-Amino-N-[2-chloro-5-(4-{[3-(methylamino)propyl]sulfonyl}piperazin-1-yl)phenyl]-1,3-oxazole-4-carboxamide (73)

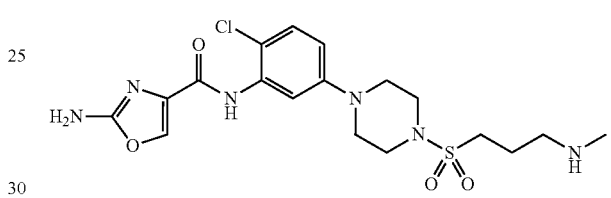

¹H NMR (400 MHz, DMSO-d₆) δ ppm 9.15 (s, 1H), 8.07 (s, 1H), 8.01 (d, J=3.0 Hz, 1H), 7.36 (d, J=8.9 Hz, 1H), 7.16 (s, 2H), 6.80 (dd, J=8.9, 3.0 Hz, 1H), 3.44-3.27 (m, 5H), 3.27-3.20 (m, 4H), 3.19-3.08 (m, 2H), 2.61 (t, J=6.9 Hz, 2H), 2.29 (s, 3H), 1.90-1.79 (m, 2H); LCMS (m/z): 457/459 [M+H]⁺.

2-Amino-N-[2-chloro-6-(4-{[3-(ethylamino)propyl]sulfonyl}piperazin-1-yl)phenyl]-1,3-oxazole-4-carboxamide (74)

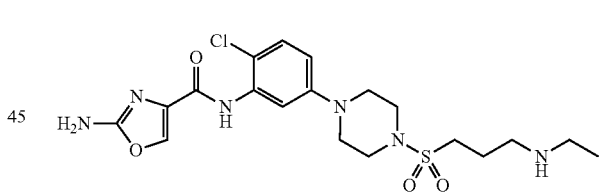

¹H NMR (400 MHz, DMSO-d₆) δ ppm 9.15 (s, 1H), 8.07 (s, 1H), 8.01 (d, J=3.0 Hz, 1H), 7.36 (d, J=8.9 Hz, 1H), 7.16 (s, 2H), 6.80 (dd, J=8.9, 3.0 Hz, 1H), 3.34-3.27 (m, 5H), 3.27-3.20 (m, 4H), 3.16-3.08 (m, 2H), 2.57 (t, J=6.6 Hz, 2H), 2.53-2.46 (m, 2H), 1.88-1.69 (m, 2H), 0.98 (t, J=7.1 Hz, 3H); LCMS (m/z): 471/473 [M+H]⁺.

2-Amino-N-[2-bromo-5-(4-{[3-(methylamino)propyl]sulfonyl}piperazin-1-yl)phenyl]-1,3-oxazole-4-carboxamide (75)

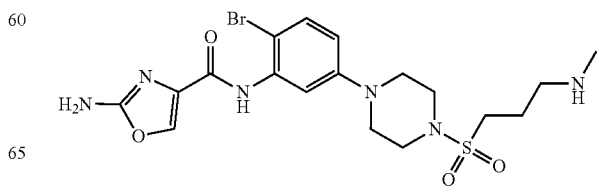

¹H NMR (400 MHz, DMSO-d₆) δ ppm 9.11 (br s, 1H), 8.07 (s, 1H), 7.99 (d, J=2.7 Hz, 1H), 7.49 (d, J=8.7 Hz, 1H), 7.15 (s, 2H), 6.75 (dd, J=8.9, 2.7 Hz, 1H), 3.41-3.26 (m, 5H), 3.23 (d, J=3.7 Hz, 4H), 3.15-3.06 (m, 2H), 2.54 (t, J=6.6 Hz, 2H), 2.24 (s, 3H), 1.83-1.76 (m, 2H); LCMS (m/z): 501/503 [M+H]⁺.

2-Amino-N-[2-bromo-5-(4-{[3-(propan-2-ylamino)propyl]sulfonyl}piperazin-1-yl)phenyl]-1,3-oxazole-4-carboxamide (76)

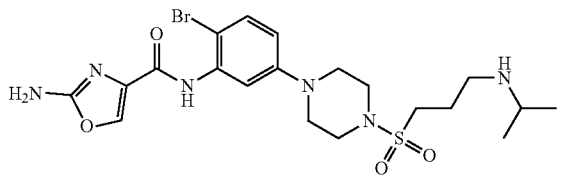

¹H NMR (400 MHz, DMSO-d₆) δ ppm 9.11 (s, 1H), 8.07 (s, 1H), 7.99 (d, J=2.7 Hz, 1H), 7.49 (d, J=8.7 Hz, 1H), 7.15 (s, 2H), 6.75 (dd, J=8.7, 2.7 Hz, 1H), 3.33-3.27 (m, 5H), 3.27-3.21 (m, 4H), 3.15-3.09 (m, 2H), 2.69-2.62 (m, 1H), 2.57 (t, J=6.9 Hz, 2H), 1.81-1.74 (m, 2H), 0.99-0.90 (m, 6H); LCMS (m/z): 5291531 [M+H]⁺.

2-Amino-N-[2-bromo-5-(4-{[3-(diethylamino)propyl]sulfonyl}piperazin-1-yl)phenyl]-1,3-oxazole-4-carboxamide (77)

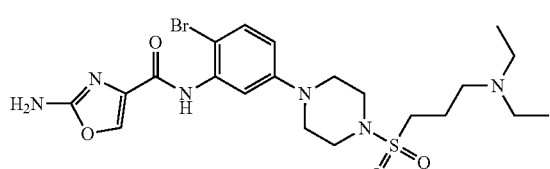

¹H NMR (400 MHz, DMSO-d₆) δ ppm 9.11 (s, 1H), 8.07 (s, 1H), 7.99 (d, J=2.8 Hz, 1H), 7.49 (d, J=8.7 Hz, 1H), 7.16 (br s, 2H), 6.75 (dd, J=9.2, 3.2 Hz, 1H), 3.33-3.29 (m, 4H), 3.25-3.22 (m, 4H), 3.13-3.09 (m, 2H), 2.61-2.38 (m, 6H), 1.80 (br s, 2H), 0.97 (br s, 6H); LCMS (m/z): 543/545 [M+H]⁺.

2-Amino-N-[2-bromo-5-(4-{[2-methyl-3-(methylamino)propyl]sulfonyl}piperazin-1-yl)phenyl]-1,3-oxazole-4-carboxamide (78)

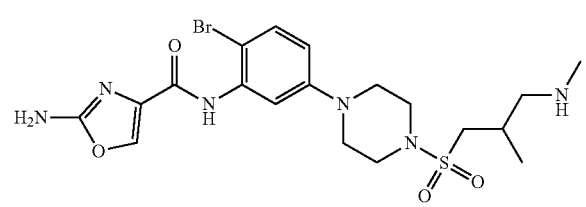 [SMILES: CNCCCS(=O)(=O)N1CCN(c2ccc(Br)c(NC(=O)c3coc(N)n3)c2)CC1]

¹H NMR (400 MHz, DMSO-d₆) δ ppm 9.11 (s, 1H), 8.07 (s, 1H), 7.99 (d, J=3.0 Hz, 1H), 7.49 (d, J=8.9 Hz, 1H), 7.16 (s, 2H), 6.75 (dd, J=8.9, 3.0 Hz, 1H), 3.43-3.19 (m, 10H), 2.85-2.74 (m, 1H), 2.46-2.39 (m, 2H), 2.26 (s, 3H), 2.20-2.07 (m, 1H), 1.05 (d, J=6.9 Hz, 3H); LCMS (m/z): 515/517 [M+H]⁺.

2-Amino-N-[2-bromo-5-(4-{[3-(ethylamino)-2-methylpropyl]sulfonyl}piperazin-1-yl)phenyl]-1,3-oxazole-4-carboxamide (79)

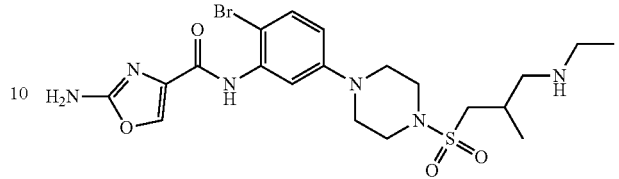

¹H NMR (400 MHz, DMSO-d₆) δ ppm 9.10 (s, 1H), 8.07 (s, 1H), 7.98 (d, J=2.7 Hz, 1H), 7.48 (d, J=8.8 Hz, 1H), 7.15 (s, 2H), 6.74 (dd, J=8.8, 2.7 Hz, 1H), 3.37-3.20 (m, 12H), 2.79 (dd, J=13.7, 8.7 Hz, 1H), 2.56-2.42 (m, 2H), 2.14-2.03 (m, 1H), 1.04 (d, J=6.9 Hz, 3H), 0.99 (t, J=7.1 Hz, 3H); LCMS (m/z): 529/531 [M+H]⁺.

2-Amino-N-[2-bromo-5-(4-{[2-methyl-3-(propan-2-ylamino)propyl]sulfonyl}piperazin-1-yl)phenyl]-1,3-oxazole-4-carboxamide (80)

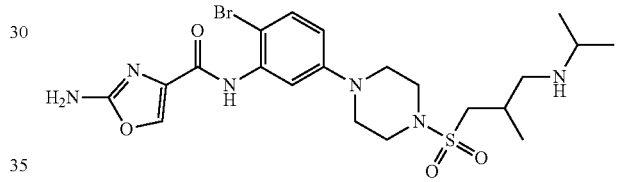

¹H NMR (400 MHz, DMSO-d₆) δ ppm 9.11 (s, 1H), 8.07 (s, 1H), 7.99 (d, J=3.2 Hz, 1H), 7.49 (d, J=8.7 Hz, 1H), 7.16 (s, 2H), 6.75 (dd, J=8.7, 3.2 Hz, 1H), 3.32-3.22 (m, 10H), 2.80 (dd, J=14.2, 8.7 Hz, 1H), 2.71-2.59 (m, 1H), 2.49-2.38 (m, 2H), 2.10-1.99 (m, 1H), 1.05 (d, J=6.9 Hz, 3H), 0.98-0.93 (m, 6H); LCMS (m/z): 543/545 [M+H]⁺.

2-Amino-N-[2-bromo-5-(4-{[3-(diethylamino)-2-methylpropyl]sulfonyl}piperazin-1-yl)phenyl]-1,3-oxazole-4-carboxamide (81)

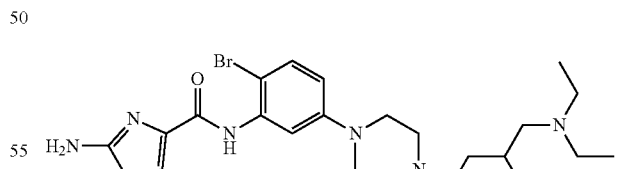

¹H NMR (400 MHz, DMSO-d₆) δ ppm 9.11 (s, 1H), 8.07 (s, 1H), 7.99 (d, J=3.2 Hz, 1H), 7.49 (d, J=9.2 Hz, 1H), 7.16 (s, 2H), 6.75 (dd, J=9.2, 3.2 Hz, 1H), 3.32-3.21 (m, 11H), 2.80 (dd, J=14.0, 8.9 Hz, 1H), 2.49-2.36 (m, 2H), 2.28-2.17 (m, 2H), 2.12-2.04 (m, 1H), 1.04 (d, J=6.4 Hz, 3H), 0.93 (t, J=7.1 Hz, 6H); LCMS (m/z): 557/559 [M+H]⁺.

2-Amino-N-[2-bromo-5-(4-{[3-(dimethylamino)-2-methyl-propyl]sulfonyl}piperazin-1-yl)phenyl]-1,3-oxazole-4-carboxamide (82)

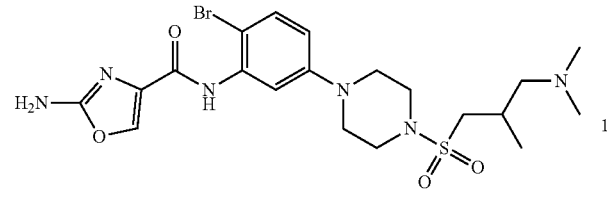

¹H NMR (400 MHz, DMSO-d₆) δ ppm 9.11 (s, 1H), 8.07 (s, 1H), 7.99 (d, J=2.7 Hz, 1H), 7.49 (d, J=8.7 Hz, 1H), 7.16 (s, 2H), 6.75 (dd, J=8.7, 2.7 Hz, 1H), 3.30-3.20 (m, 10H), 2.89-2.73 (m, 1H), 2.29-1.92 (m, 8H), 1.05 (d, J=6.0 Hz, 3H); LCMS (m/z): 529/531 [M+H]⁺.

3.42-3.36 (m, 4H), 3.22-3.16 (m, 4H), 2.84-2.68 (m, 2H), 2.00-1.94 (m, 2H), 1.49-1.40 (m, 2H), 1.37 (8, 9H); LCMS (m/z): 613/615 [M+H]⁺.

2-Amino-N-{2-bromo-6-[4-(piperidin-4-ylsulfonyl)piper-azin-1-yl]phenyl}-1,3-oxazole-4-carboxamide (84)

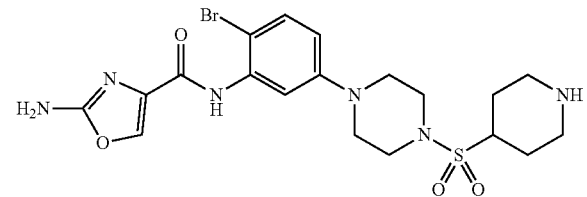

To a solution of tert-butyl 4-{[4-(3-{[(2-amino-1,3-oxazol-4-yl)carbonyl]amino}-4-bromophenyl)piperazin-1-yl]sulfonyl}piperidine-1-carboxylate 83 (0.58 g, 0.95 mmol) in Scheme 10- Preparation of example 85

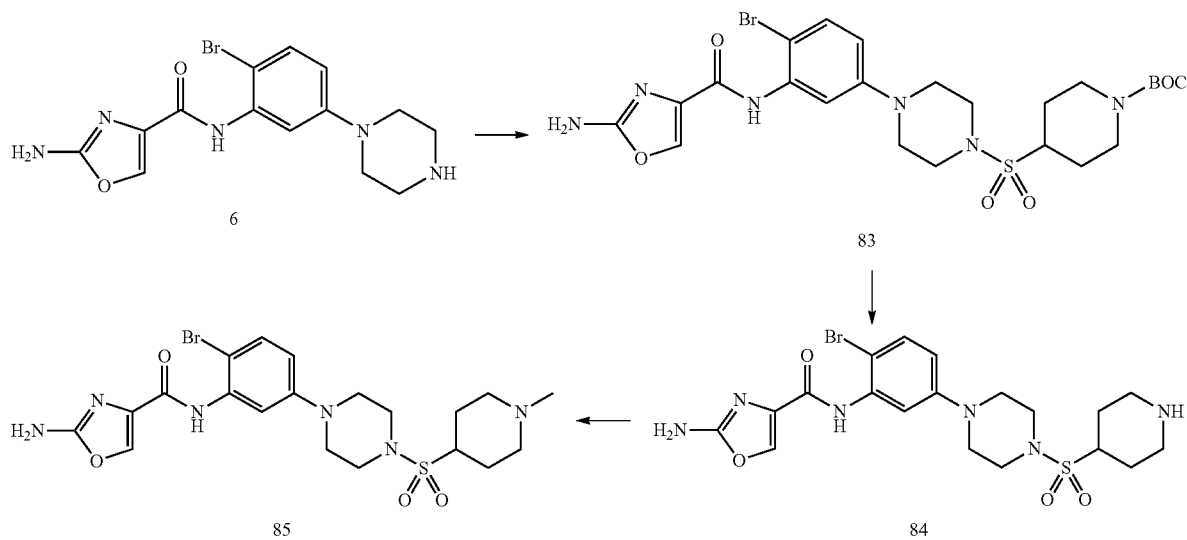

tert-Butyl-4-{[4-(3-{[(2-amino-1,3-oxazol-4-yl)carbonyl]amino}-4-bromophenyl)piperazin-1-yl]sulfonyl}piperidine-1-carboxylate (83)

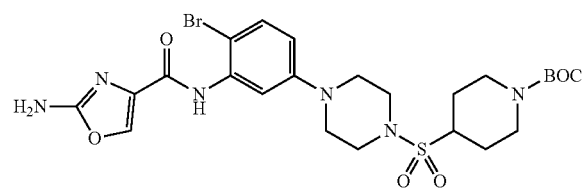 [SMILES: CC(C)(C)OC(=O)N1CCC(S(=O)(=O)N2CCN(c3ccc(Br)c(NC(=O)c4coc(N)n4)c3)CC2)CC1]

To a solution of intermediate 6 (500 mg, 0.55 mmol) in DMF (10 mL) at 0° C. was added TEA (0.57 mL, 1.64 mmol) and tert-butyl 4-(chlorosulfonyl)piperidine-1-carboxylate (359 mg, 0.55 mmol) and the reaction allowed to warm to rt and stirred for 2 h. It was then quenched with water, diluted with EtOAc and LiCl solution added. The organic layer was separated and evaporated in vacuo to give 83 (588 mg, 70%) as a yellow powder; ¹H NMR (400 MHz, DMSO-d₆) δ ppm 9.10 (s, 1H), 8.07 (s, 1H), 7.99 (d, J=2.7 Hz, 1H), 7.49 (d, J=9.2 Hz, 1H), 7.15 (s, 2H), 6.74 (dd, J=9.2, 2.7 Hz, 1H), 4.05-3.97 (m, 2H), 3.49-3.42 (m, 1H), DCM (5 mL) was added TFA (5 mL) at rt and the reaction stirred for 2 h. The reaction mixture was concentrated in vacuo, and then saturated NaHCO₃ (aq) solution was added to the residue. The resulting precipitate was filtered to obtain compound 84 (0.37 g, 76%) as a solid; ¹H NMR (400 MHz, DMSO-d₆) δ ppm 9.10 (s, 1H), 8.06 (s, 1H), 7.98 (d, J=2.7 Hz, 1H), 7.49 (d, J=9.2 Hz, 1H), 7.15 (s, 2H), 6.74 (dd, J=9.2, 2.7 Hz, 1H), 3.58-3.25 (m, 6H), 3.29-3.10 (m, 6H), 2.73-2.63 (m, 2H), 2.03-1.94 (m, 2H), 1.68-1.56 (m, 2H); LCMS (m/z): 513/515 [M+H]⁺.

2-Amino-N-(2-bromo-5-{4-[(1-methylpiperidin-4-yl)sulfo-nyl]piperazin-1-yl}phenyl)-1,3-oxazole-4-carboxamide (85)

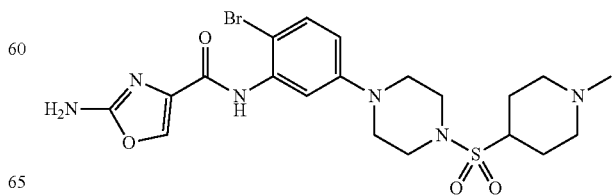

AcOH (17 µL, 0.29 mmol), formaldehyde (10 µL, 0.13 mmol) and sodium triacetoxyborohydride (61 mg, 0.29 mmol) were added to 84 (75 mg, 0.15 mmol) in DMF (1 mL) and stirred at rt for 18 h. The reaction was quenched with saturated NaHCO$_3$ (aq) solution and extracted with DCM. The organics were dried, and then purified by preparative HPLC to obtain 85 (12 mg, 16%) as a white solid; $^1$H NMR (400 MHz, DMSO-d$_6$) δ ppm 9.10 (s, 1H), 8.07 (s, 1H), 7.98 (d, J=3.0 Hz, 1H), 7.49 (d, J=8.9 Hz, 1H), 7.15 (s, 2H), 6.74 (dd, J=8.9, 3.0 Hz, 1H), 3.43-3.35 (m, 4H), 3.21-3.17 (m, 4H), 3.16-3.09 (m, 1H), 2.90-2.75 (m, 2H), 2.14 (s, 3H), 1.98-1.78 (m, 4H), 1.69-1.52 (m, 2H); LCMS (m/z): 527/529 [M+H]$^+$.

The following examples were prepared using analogous procedures:

2-Amino-N-{2-chloro-5-[4-(piperidin-4-ylsulfonyl)piperazin-1-yl]phenyl}-1,3-oxazole-4-carboxamide (86)

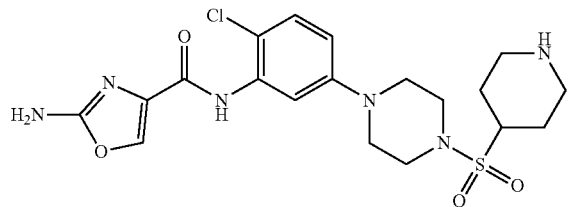 [SMILES: Nc1nc(C(=O)Nc2cc(N3CCN(S(=O)(=O)C4CCNCC4)CC3)ccc2Cl)co1]

$^1$H NMR (400 MHz, DMSO-d$_6$) δ ppm 9.15 (s, 1H), 8.07 (s, 1H), 8.00 (d, J=3.0 Hz, 1H), 7.36 (d, J=8.7 Hz, 1H), 7.16 (s, 2H), 6.79 (dd, J=8.7, 3.0 Hz, 1H), 3.43-3.36 (m, 5H), 3.31-3.21 (m, 1H), 3.20-3.15 (m, 4H), 3.00-2.95 (m, 2H), 2.48-2.39 (m, 2H), 1.88-1.83 (m, 2H), 1.51-1.44 (m, 2H); LCMS (m/z): 469/471 [M+H]$^+$.

2-Amino-N-{2-chloro-8-(4-[(1-methylpiperidin-4-yl)sulfonyl]piperazin-1-yl}phenyl)-1,3-oxazole-4-carboxamide (87)

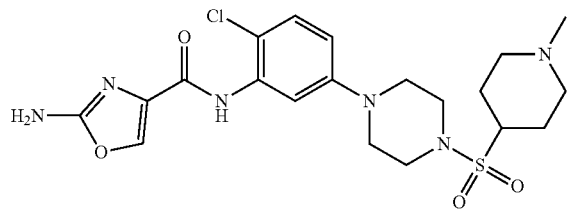 [SMILES: CN1CCC(S(=O)(=O)N2CCN(c3ccc(Cl)c(NC(=O)c4coc(N)n4)c3)CC2)CC1]

$^1$H NMR (400 MHz, DMSO-d$_6$) δ ppm 9.15 (s, 1H), 8.07 (s, 1H), 8.00 (d, J=3.2 Hz, 1H), 7.36 (d, J=9.2 Hz, 1H), 7.16 (s, 2H), 6.79 (dd, J=9.2, 3.2 Hz, 1H), 3.42-3.36 (m, 4H), 3.27-3.11 (m, 5H), 3.02-2.82 (m, 2H), 2.20 (br s, 3H), 2.09-1.86 (m, 4H), 1.70-1.58 (m, 2H); LCMS (m/z): 483/485 [M+H]$^+$.

2-Amino-N-{2-bromo-5-[4-(pyrrolidin-3-ylsulfonyl)piperazin-1-yl]phenyl}-1,3-oxazole-4-carboxamide (88)

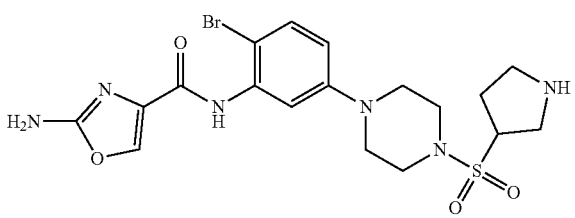 [SMILES: Nc1nc(C(=O)Nc2cc(N3CCN(S(=O)(=O)C4CCNC4)CC3)ccc2Br)co1]

$^1$H NMR (400 MHz, DMSO-d$_6$) δ ppm 9.09 (s, 1H), 8.06 (s, 1H), 7.99 (d, J=2.7 Hz, 1H), 7.49 (d, J=9.2 Hz, 1H), 7.16 (s, 2H), 6.74 (dd, J=9.2, 2.7 Hz, 1H), 3.78-3.67 (m, 1H), 3.40-3.28 (m, 4H), 3.25-3.15 (m, 5H), 3.10 (dd, J=11.9, 8.2 Hz, 1H), 2.96 (dd, J=11.9, 6.4 Hz, 1H), 2.85-2.69 (m, 2H), 2.07-1.97 (m, 1H), 1.93-1.84 (m, 1H); LCMS (m/z): 499/501 [M+H]$^+$.

2-Amino-N-(2-bromo-5-{4-[(1-methylpyrrolidin-3-yl)sulfonyl]piperazin-1-yl}phenyl)-1,3-oxazole-4-carboxamide (89)

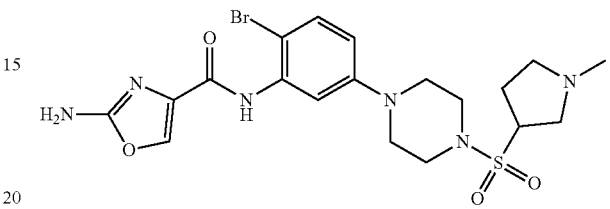

$^1$H NMR (400 MHz, DMSO-d$_6$) δ ppm 9.10 (s, 1H), 8.07 (s, 1H), 7.98 (d, J=3.0 Hz, 1H), 7.48 (d, J=8.9 Hz, 1H), 7.16 (s, 2H), 6.74 (dd, J=8.9, 3.0 Hz, 1H), 3.96-3.88 (m, 1H), 3.36-3.33 (m, 4H), 3.21-3.16 (m, 4H), 2.85-2.80 (m, 1H), 2.63 (dd, J=10.1, 6.4 Hz, 1H), 2.53-2.46 (m, 2H), 2.24 (s, 3H), 2.16-2.08 (m, 1H), 2.06-1.98 (m, 1H); LCMS (m/z): 513/515 [M+H]$^+$.

PAICS 2D Cell Proliferation Assay

Cell Culture

Frozen cryovial stocks of LM2 and MDA-MB-231 breast cancer cell lines were thawed and cultured in 4.5 g/L glucose DMEM (31966-047, Invitrogen) supplemented with 10% Fetal Bovine Serum (10500-064, Invitrogen) until confluent in a T175 flask. Cells were incubated at 37° C. with 5% CO$_2$ in a humidified incubator.

Day 1—Cell Plating

Cells were collected from T175 flasks by washing with PBS (10010-056, Invitrogen) and dissociated using Accutase (A6964, Sigma Aldrich). This was followed by centrifuging (1200 rpm, 5 min) and resuspending the cells in 10 ml of media containing 1% penicillin/streptomycin (15140-122, Invitrogen). Cells were counted by trypan blue exclusion method using an automated cell counter (Cellometer) and diluted to a concentration of 40,000/ml. 1000 cells were then seeded into 384-well white-walled plates (Corning, 3707) in a volume of 25 µl. Plates were Incubated overnight at 37° C. with 5% CO$_2$.

Day 2—Compound Addition

After 24 hours, PAICS compounds were added onto the assay plates using an HP D300 Digital Dispenser (Hewlett Packard). 10 mM stocks were used and dispensed as a 10 point concentration response curve (CRC) ½ log dilution series with a final top concentration of 100 µM. Controls were added onto each plate: positive controls included Staurosporine CRC (100 µM stock dispensed as a 10 point CRC ½ log dilution series with a final top concentration of 1 µM) and PAICS compound MRT00211919 (10 mM stock dispensed as a 10 point CRC ½ log dilution series with a final top concentration of 100 µM); a high control of Staurosporine (0.1 µM (LM2), 0.316 µM (MDA-MB-231) FAC) and a low control of media containing 1% DMSO. A final concentration of 1% DMSO was then added across the plates for normalisation. Following compound addition, assay plates were incubated for 72 hours at 37° C. with 5% CO$_2$.

Day 5—Cytotoxicity and Cell Viability Assays

After 72 h incubation, dead and viable cells were measured in each assay plate. Cytotoxicity was assessed through fluorescent DNA staining using the CellTox™ Green Cytotoxicity Assay kit (G8743, Promega) following the manufacturer's multiplexing protocol. Impaired cell membrane integrity results in the access of dye to stain DNA allowing quantification of dead cells. Cell viability was determined following ATP quantification using the CellTiter-Glo® Luminescent Cell Viability Assay kit (G7572, Promega) following the manufacturer's protocol. ATP released from lysed cells allowed for the generation of a signal proportional to the number of cells present in the well. All endpoint reads were performed using the PheraSTAR Plus (BMG Labtech). Data is expressed as % viable cells and % dead cells against controls (mean±SEM of duplicate curves).

Biochemical Assay to Measure PAICS Activity

Figure 3:
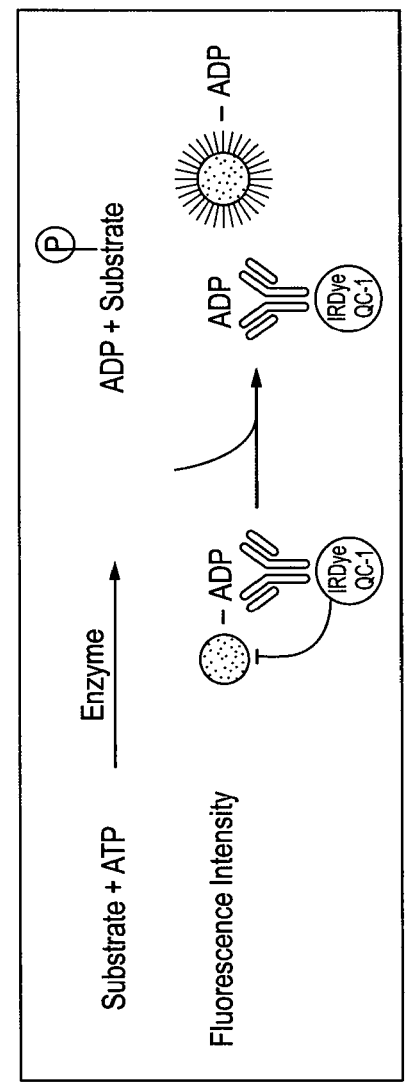
FIG. 3 shows the Transcreener FI assay principle.

Assay Principle:

The biochemical assay was used to measure PAICS SAICAR synthetase-mediated conversion of CAIR, aspartic acid and ATP to SAICAR, ADP and inorganic phosphate ($P_i$), post-AIR/CAIR equilibration (see FIG. 3). This was achieved by detecting the ADP generated during the reaction, using Bellbrook Lab's Transcreener $ADP^2$ FI assay. An increase in the fluorescence intensity is directly proportional to the amount of PAICS activity.

The Transcreener $ADP^2$ FI assay is a homogeneous competitive displacement fluorescence intensity assay which uses direct immunodetection of ADP. Displacement of the tracer by ADP causes an increase in the fluorescence at excitation 590 nm and emission 617 nm (FIG. 3).

Method:

5 µl WT full length PAICS (final assay concentration, fac, 2.5 nM) in basic buffer, added to black, non-binding, 384-well plates (Corning #3575), columns 1 to 22. 5 µl basic buffer was added to columns 23+24 (negative control). PAICS stock at 31.9 µM from the PI's lab (Steve Firestine). Basic buffer contained 50 mM Tris-HCl pH8 and 0.5 mM EDTA, fac.

1 µl compound in 100% DMSO added per well, or 1 µl 100% DMSO to positive controls (columns 1+2) and negative controls (columns 23+24). Final assay top concentration of compound either 1 mM or 30-µM, serially diluted with half-log dilutions across the plate in duplicate (one 10-point concentration response curve across wells 3 to 12, another across 13 to 22). Compounds pre-incubated with PAICS enzyme for 30 mins at RT. 2 µl CAIR added (fac 10 µM) in basic buffer plus 25 mM $MgCl_2$ and 50 mM $KHCO_3$ fac to all wells. CAIR stock 50 mM from Steve Firestine's lab. 1 hr RT incubation for AIR-CAIR equilibration. NB: ~50% CAIR is decarboxylated during equilibration therefore 5 µM remains for the synthetase reaction.

2 µl ATP/aspartic acid added (fac 30 µM/180 µM) in reaction buffer to all wells. 30 mins RT incubation for appropriate level of ATP turnover. Reaction buffer contained basic buffer plus 10 mM DTT, 0.01% BSA and 0.01% Brij 35, fac.

10 µl ADP detection reagent added to all wells (as per instructions, Transcreener $ADP^2$ FI kit, BellBrook Labs #3013-10K). Incubation for 1 h at RT to allow antibody equilibration. Fluorescence intensity determined using a Tecan Safire2 (excitation at 590 nm, emission at 617 nm).

The results of the above assays for selected compounds of the invention are shown in Table 1.

PAICS Biochemical Activity $IC_{50}$
A=<10 nM; B=10-25 nM; C=25-100 nM; D=>100 nM; nt: not tested PAICS 2D Cell Proliferation Activity $EC_{50}$
A=<100 nM; B=100-250 nM; C=250-500 nM; D=500-1000 nM

TABLE 1

| Example number | PAICS Biochemical $IC_{50}$ | PAICS 2D Cell Proliferation $EC_{50}$ |
|---|---|---|
| 19 | D | D |
| 20 | B | D |
| 21 | B | B |
| 22 | D | B |
| 23 | B | B |
| 24 | B | B |
| 25 | B | B |
| 26 | nt | D |
| 27 | nt | D |
| 28 | B | C |
| 29 | C | D |
| 30 | D | D |
| 31 | C | D |
| 32 | C | D |
| 33 | C | D |
| 34 | C | D |
| 35 | C | D |
| 44 | B | D |
| 45 | B | C |
| 46 | D | D |
| 53 | C | D |
| 54 | A | B |
| 55 | A | A |
| 56 | B | C |
| 57 | B | D |
| 58 | C | D |
| 59 | B | C |
| 60 | B | C |
| 61 | B | B |
| 62 | B | C |
| 63 | A | A |
| 64 | A | B |
| 65 | B | B |
| 66 | B | B |
| 67 | A | A |
| 68 | B | C |
| 69 | A | A |
| 70 | A | A |
| 71 | nt | A |
| 72 | A | B |
| 73 | B | C |
| 74 | A | C |
| 75 | A | B |
| 76 | A | A |
| 77 | A | A |
| 78 | nt | A |
| 79 | nt | A |
| 80 | nt | A |
| 81 | nt | B |
| 82 | nt | B |
| 84 | A | B |
| 85 | A | B |
| 86 | B | C |
| 87 | B | C |
| 88 | nt | B |
| 89 | nt | B |

CRISPR Editing

Cas9 nuclease-mediated gene editing (Sander and Joung, 2014) was performed using a CRISPR RNA guide sequence (TACGAATTGTTAGACAGTCC, PAM: AGG) targeting exon 3 in the human PAICS gene (accession number: NM_006452).

Stable cell clones were isolated and gene disruption confirmed by DNA sequencing and the absence of PAICS cellular protein expression confirmed by Western blotting.

A small set of compounds were tested against wild type LM2 and CRISPR edited LM2 in the 2D cell proliferation assay to establish to what extent the cellular potency was driven by PAICS mediated effects. The data is shown in Table 2: compounds tested had no effect on CRISPR edited cells, confirming the on-targets effect as being PAICS mediated.

TABLE 2

| Example number | Potency shift: CRISPR Cell $EC_{50}$/WT Cell $EC_{50}$ |
|---|---|
| 23 | >500 |
| 24 | >500 |
| 55 | >500 |
| 69 | >500 |

Evaluation of Compound 69 in MDA-MB-231-Dlux Xenograft Model

Figure 4:
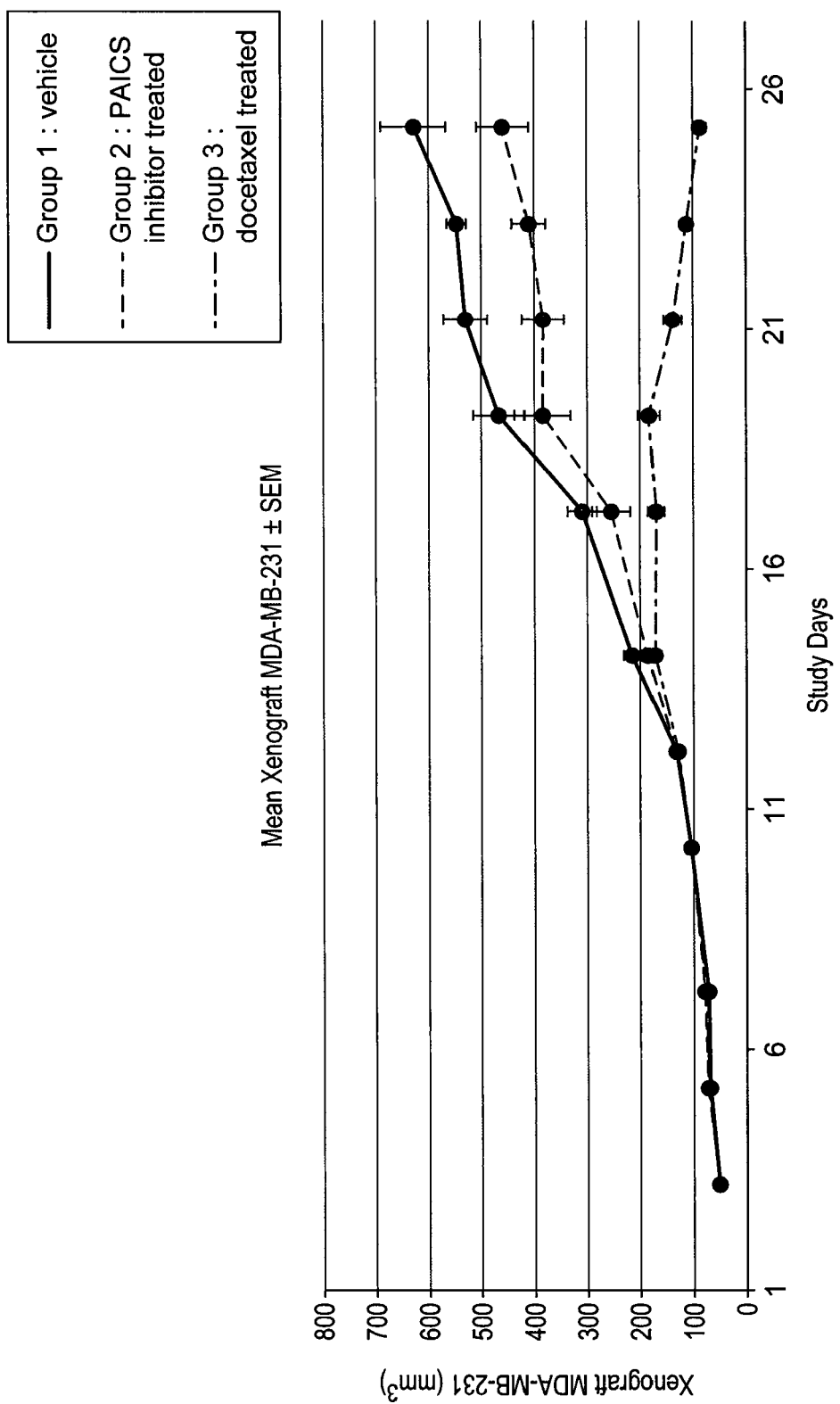
FIG. 4 shows the effect of Compound 69 in a xenograft model (MDA-MB-231-Dlux Xenograft Model), showing tumour volume against study days.

Protocol:

Mice were implanted with MDA-MB-231 Dlux cells in the mammary fat pad. Mice were treated with test agent, (Compound 69), standard of care control agent, docetaxel, or vehicle control, once tumours reached a mean volume of ~100-200 mm³. Tumours were measured every 2-3 days using electronic calipers and tumour volume estimated using the formula 0.5 (L×W²). Treatment continued for 2 weeks. Mice were observed and body weight measured daily Mice:
MF-1 (HsdOla:MF1-Foxn1$^{nu}$)
Female 5-8 weeks
n=12 per group
Cells:
MDA-MB-231 Dlux (Bioluminescent MDA-MD-231 variant)
Implantation Site: Mammary fat pad (1:1 matrgel/PBS)
Groups:
Vehicle (10% DMSO)
Compound 69 (Oral 25 mg/kg twice daily)
Docetaxel (IV 5 mg/kg twice weekly)
Results Mice treated with PAICS inhibitor (25 mg/kg bid) showed a statistically significant reduction in growth of primary tumour. The results are shown in FIG. 4.

Evaluation of the Growth of PAICS CRISPR KD MDA231 Cells in Chorioallantoic Membrane (CAM) Model Protocol:

Fertilised white leghorn eggs were incubated at 37.5° C. with relative humidity for 9 days. At E9 the chiorioallantoic membrane (CAM) was dropped by drilling a small hole through the eggshell into the air sac and a cm² window was cut in the eggshell above the CAM. 2×10⁶ MDA231 cells were added onto the CAM of the egg (groups included: wild type MDA231 cells; CRISPR KD control cells; PAICS CRISPR KD clone 3 cells; and PAICS CRISPR KD clone 14 cells). At E18 the upper portion of the CAM, with the tumour, was removed, transferred in PFA 4%. After 48 hour in PFA, tumour was washed three times in PBS and the tumour was carefully cut away from normal CAM tissue. Tumour was then weighted and a one-way ANOVA analysis done on data for the 4 groups Tun and PAICS CRISPR KD (KD clones 3 & 14), as well as wild type MDA231 cells and control CRISPR cells. Table 3 shows the groups for the study.

TABLE 3

| Group description | | Name group in the report | Amount of cells/egg | Nb of eggs grafted/group |
|---|---|---|---|---|
| Group 1 | Wild type MDA231 cells | WT | 2.10⁶ | 21 |
| Group 2 | Modified MDA231 cells-Control | Ctrl 1 | 2.10⁶ | 21 |
| Group 3 | Modified MDA231 cells-KD 3 modification | KD 3 | 2.10⁶ | 21 |
| Group 4 | Modified MDA231 cells-KD 14 modification | KD 14 | 2.10⁶ | 21 |

Results

Figure 5:
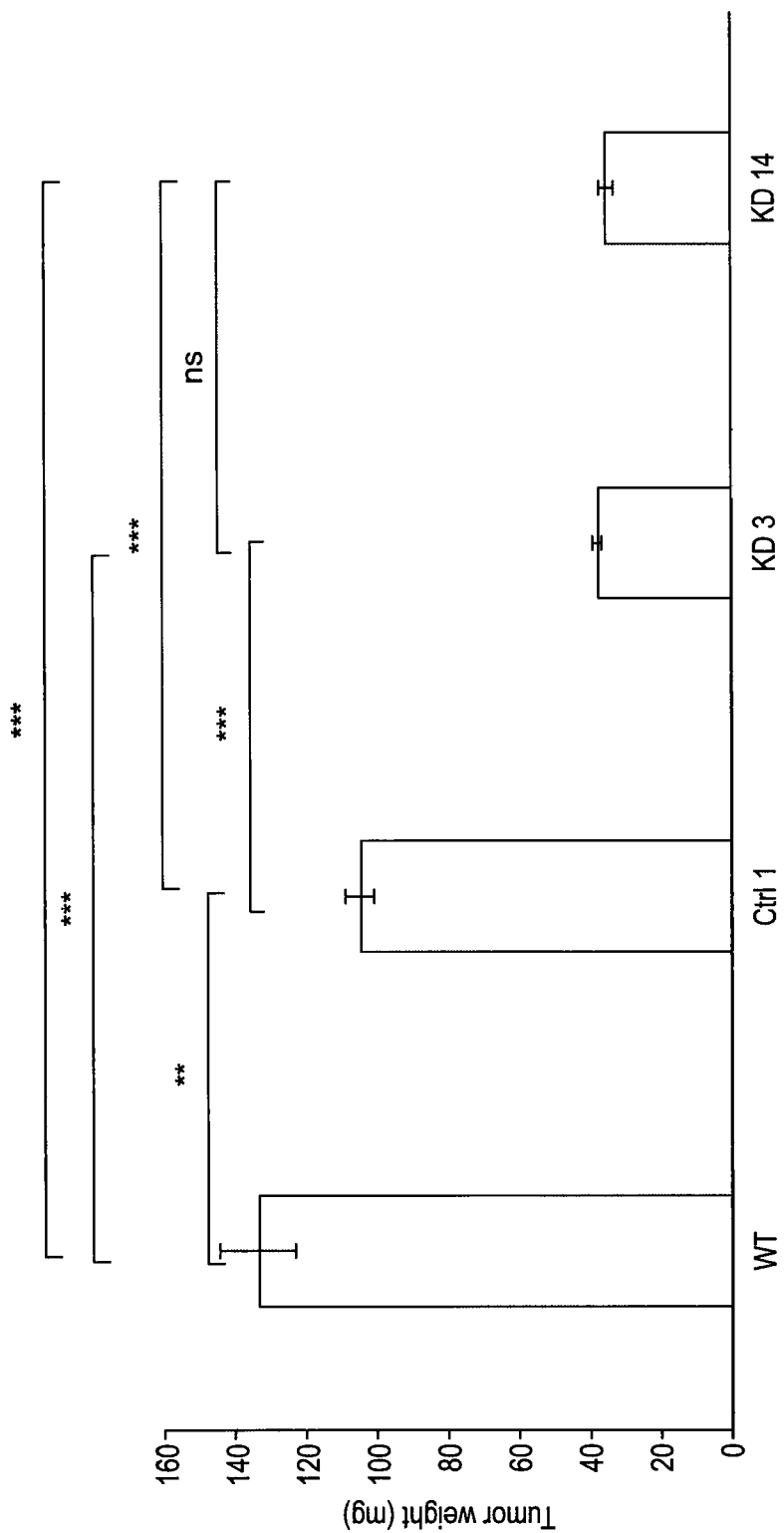
FIG. 5 shows the mean tumour weight (mg) measured in the different experimental groups (WT, Ctrl 1, KD 3 and KD 14).

Table 4 presents the mean value, SD, SEM and p-value of tumour weight (mg) for each experimental group at E18 (n is the number of eggs alive at the end of the study). The mean tumour weight (mg) measured in the different experimental groups is shown in FIG. 5.

TABLE 4

| | n | Tumor weight (mg) | SD | SEM | p value vs WT | p value vs. Ctrl 1 | p value vs. KD3 |
|---|---|---|---|---|---|---|---|
| WT | 13 | 133,492 | 38,420 | 10,656 | / | / | / |
| Ctrl 1 | 19 | 104,433 | 17,383 | 3,988 | 0.0068 | / | / |
| KD 3 | 17 | 37,435 | 6,246 | 1,515 | <0.00001 | <0.00001 | / |
| KD 14 | 15 | 35,195 | 8,181 | 2,112 | <0.00001 | <0.00001 | 0.3878 |

Figure 6:
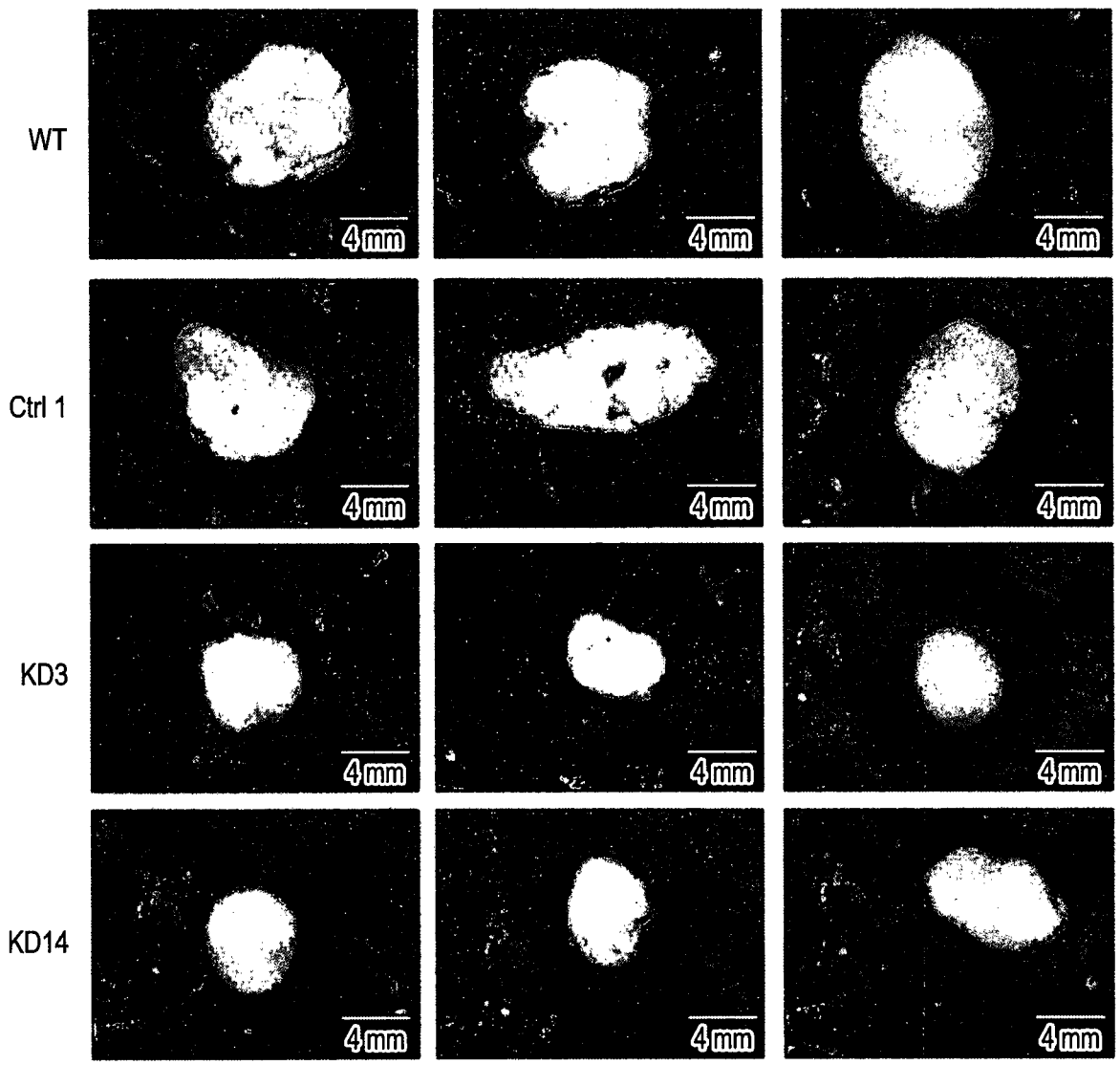
FIG. 6 shows representative images of tumours for each group (3 tumours per group) in the evaluation of the growth of PAICS CRISPR KD MDA231 cells in a Chorioallantoic Membrane (CAM) model. PAICS CRISPR KD clones (KD3 and KD14) of MDA231 modified cells showed a significant reduction in tumour development compared to wild type and control modified MDA231 cells.

PAICS CRISPR KD clones (KD3 and KD14) of MDA231 modified cells showed a significant reduction in tumour development compared to wild type and control modified MDA231 cells. See FIG. 6.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A compound of formula (I), or a pharmaceutically acceptable salt or ester thereof,

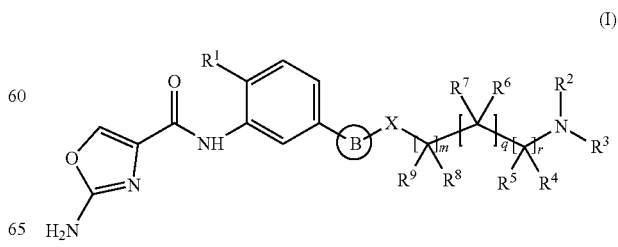

wherein:

B is a saturated or partially unsaturated monocyclic or bicyclic, heterocyclic group optionally substituted by one or more $R^{10}$ groups and optionally containing one or more CO groups;

X is selected from $SO_2$, $CO_2$, CO, $CONR^{11}$, $NR^{11}CO$ and $(CR^{12}R^{13})_p$;

$R^1$ is independently selected from halogen, $OR^{14}$, $SR^{14}$ and $R^{14}$;

$R^2$ is selected from H and alkyl;

$R^3$ is selected from H, alkyl, cycloalkyl and heterocycloalkyl, each of which is optionally substituted by one or more substituents selected from $NR^{24}R^{25}$ and $R^{26}$, or $R^3$ is linked to one of $R^4$, $R^5$, $R^6$, $R^7$, $R^8$ or $R^9$ to form a saturated heterocyclic group; or $R^2$ and $R^3$ are linked together with the nitrogen to which they are attached to form a saturated heterocyclic group optionally containing one or more additional heteroatoms selected from O, N and S, and optionally substituted by one or more $R^{27}$ groups;

each $R^4$ and $R^5$ is independently selected from H, alkyl, $(CH_2)_sOR^{15}$ and $(CH_2)_tNR^{16}R^{17}$; or one of $R^4$ and $R^5$ is H or alkyl and the other is linked to $R^3$ to form a saturated heterocyclic group, or one of $R^4$ and $R^5$ is linked to one of $R^8$ or $R^9$ to form a cyclic group;

each $R^6$ and $R^7$ is independently selected from H, alkyl, $(CH_2)_uOR^{18}$ and $(CH_2)_vNR^{19}R^{20}$; or one of $R^6$ and $R^7$ is H or alkyl and the other is linked to $R^3$ to form a saturated heterocyclic group;

each $R^8$ and $R^9$ is independently selected from H, alkyl, $(CH_2)_wOR^{21}$ and $(CH_2)_xNR^{22}R^{23}$; or one of $R^8$ and $R^9$ is H or alkyl and the other is linked to $R^3$ to form a saturated heterocyclic group; or one of $R^8$ and $R^9$ is linked to one of $R^4$ and $R^5$ to form a cyclic group;

$R^{10}$ is selected from alkyl, OH, halogen, alkoxy, $CO_2$-alkyl, COOH, CO-alkyl and CN;

$R^{11}$, $R^{12}$, $R^{13}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ are each independently H or alkyl;

$R^{14}$, $R^{26}$ and $R^{27}$ are each independently alkyl;

m, q and r are each independently 0, 1 or 2, such that the sum of m+q+r is 2, 3 or 4;

p is an integer selected from 0, 1 and 2; and s, t, u, v, w and x are each independently 0, 1, 2, 3 or 4.

2. A compound according to claim 1 wherein B is a monocyclic 5- or 6-membered saturated or partially unsaturated heterocyclic group optionally substituted by one or more $R^{10}$ groups.

3. A compound according to claim 1 wherein:

each $R^4$ and $R^5$ is independently selected from H and alkyl; or one of $R^4$ and $R^5$ is H or alkyl and the other is linked to $R^3$ to form a saturated heterocyclic group;

each $R^6$ and $R^7$ is independently selected from H and alkyl; or one of $R^6$ and $R^7$ is H or alkyl and the other is linked to $R^3$ to form a saturated heterocyclic group; and each $R^8$ and $R^9$ is independently selected from H and alkyl; or one of $R^8$ and $R^9$ is H or alkyl and the other is linked to $R^3$ to form a saturated heterocyclic group.

4. A compound according to claim 1 which is of formula (Ib), or a pharmaceutically acceptable salt or ester thereof,

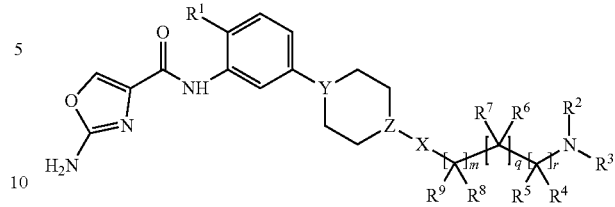

wherein Y and Z are both N, or one of Y and Z is N, and the other is CH; and $R^{1-9}$, X, m, q and r are as defined in claim 1.

5. A compound according to claim 4 wherein Y and Z are both N.

6. A compound according to claim 1 wherein $R^1$ is selected from Br, I, Cl, OMe, SMe and Me.

7. A compound according to claim 1 wherein X is $CO_2$ or $SO_2$.

8. A compound according to claim 1 wherein:

$R^2$ is selected from H, methyl, ethyl and isopropyl; and $R^3$ is selected from methyl, ethyl, isopropyl and cyclopropyl.

9. A compound according to claim 1 wherein $R^2$ and $R^3$ are linked together with the nitrogen to which they are attached to form a 5- or 6-membered saturated heterocyclic group.

10. A compound according to claim 1 wherein:

m is 1 or 2;

q is 1 or 2;

r is 0;

$R^8$ and $R^9$ are each independently H or alkyl; and $R^6$ and $R^7$ are each independently H or alkyl.

11. A compound according to claim 1 wherein:

m is 1;

q is 1 or 2;

r is 0;

one of $R^8$ and $R^9$ is H or alkyl and the other is linked to $R^3$ to form a saturated heterocyclic group; and each $R^6$ and $R^7$ is independently H or alkyl.

12. A compound according to claim 1 wherein:

m is 1;

q is 1;

r is 1 or 2;

$R^8$ and $R^9$ are each independently H or alkyl;

one of $R^6$ and $R^7$ is H or alkyl and the other is linked to $R^3$ to form a saturated heterocyclic group; and $R^4$ and $R^5$ are each independently H or alkyl.

13. A compound according to claim 1 which is selected from the following,

19

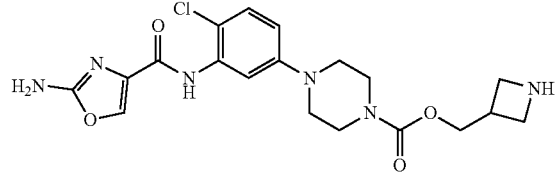

-continued

34
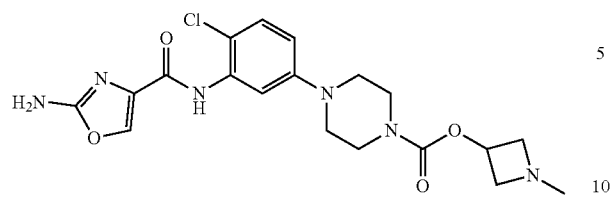
35
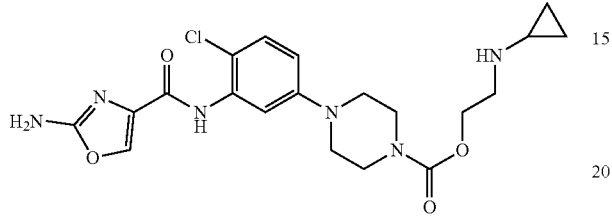
44
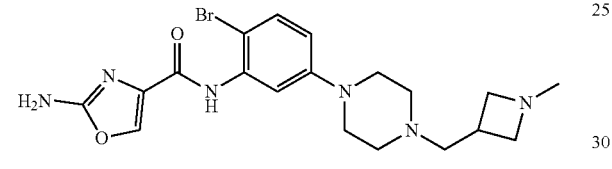
46
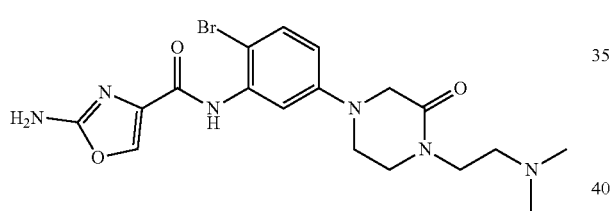
53
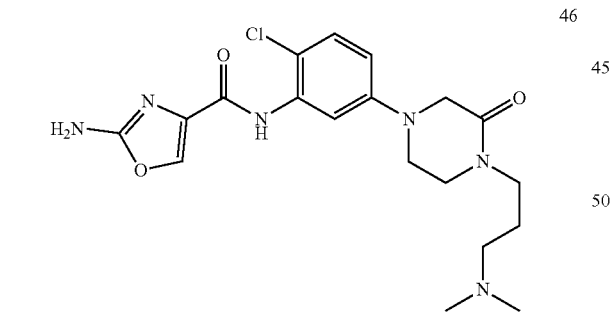
54
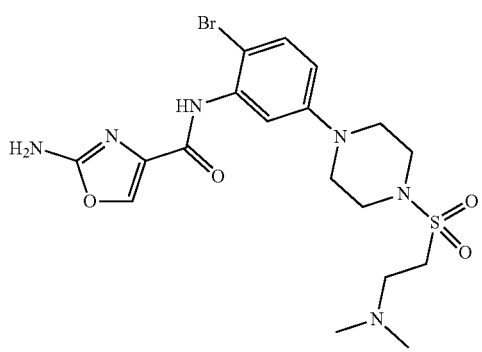
55
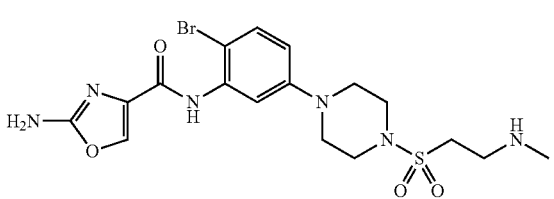
56
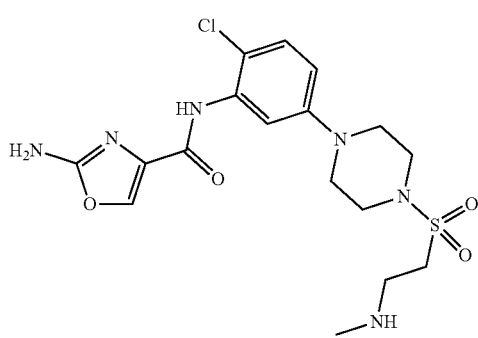
57
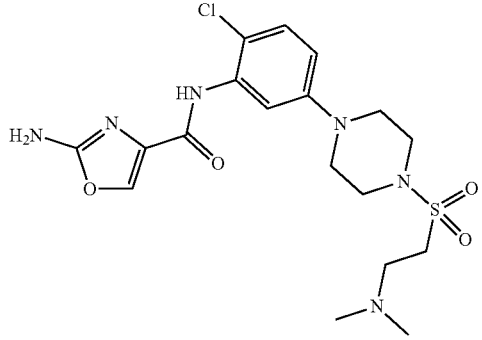
58
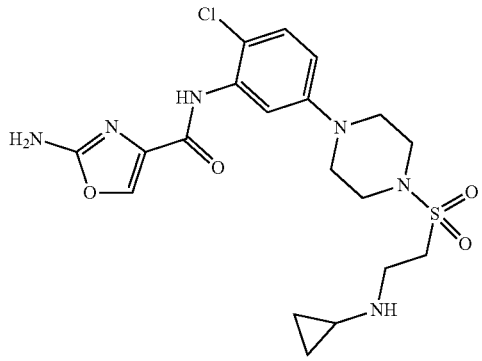

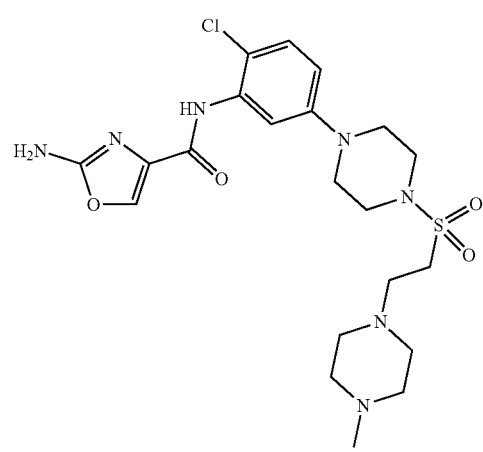
59
60
61
62
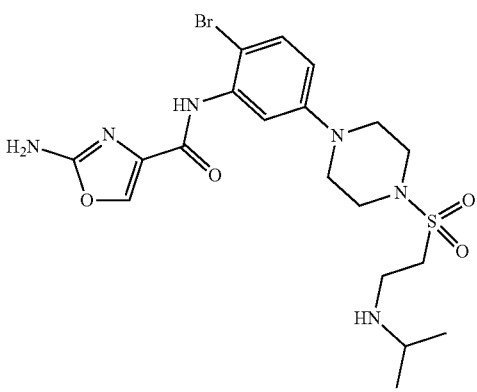
63
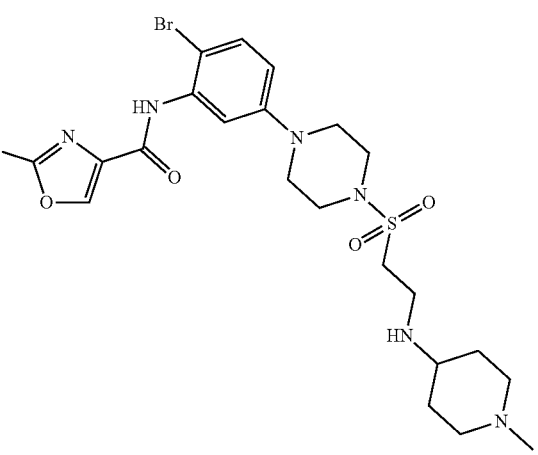
64
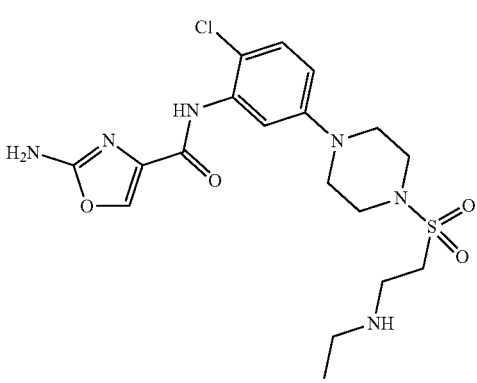
65
66

67
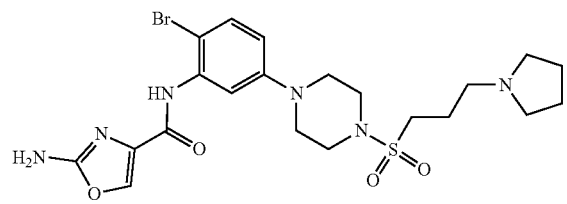
68
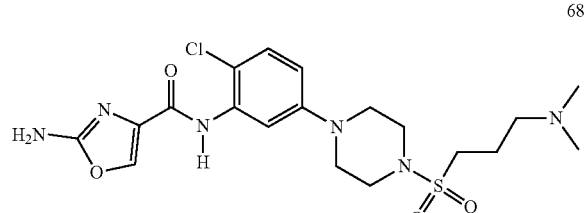
69
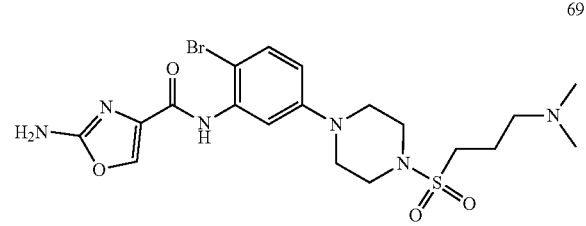
70
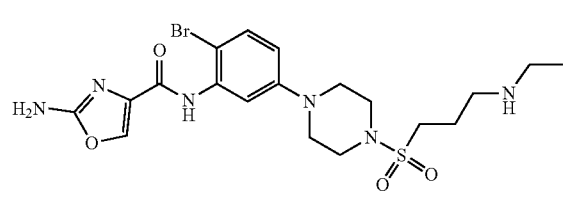
71
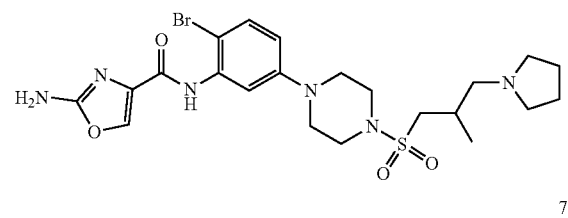
72
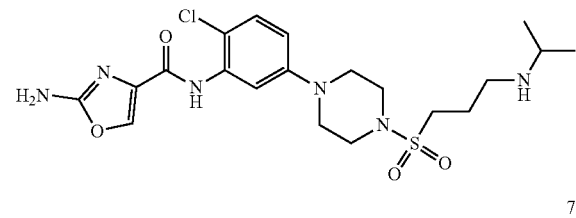
73
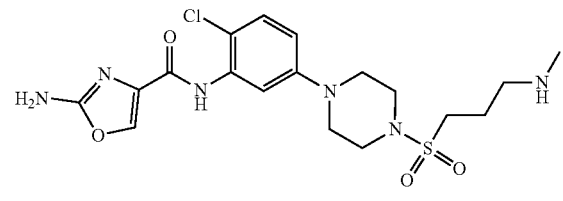
74
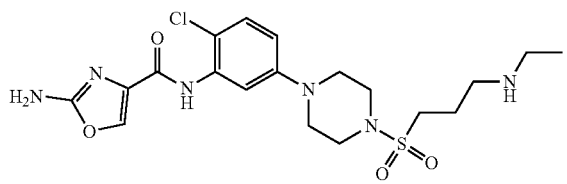
75
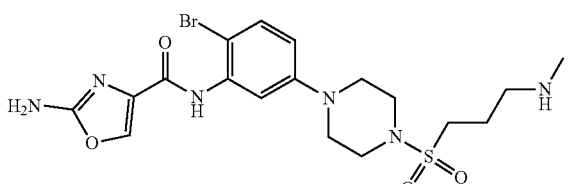
76
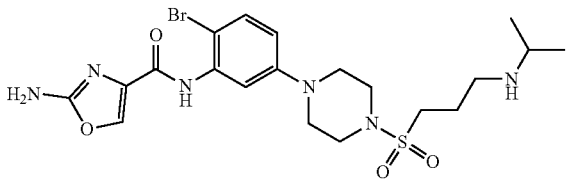
77
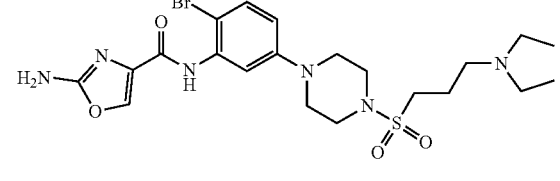
78
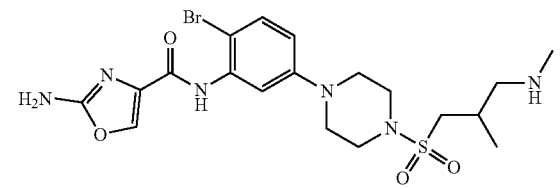
79
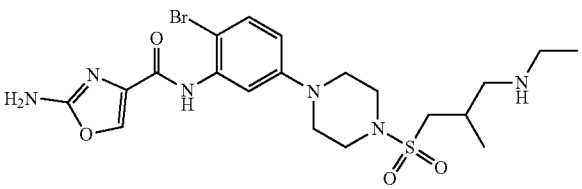
80
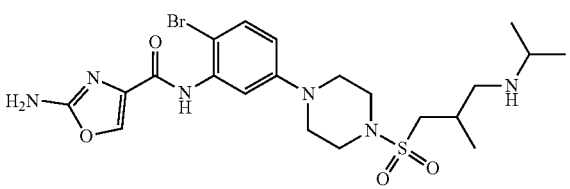

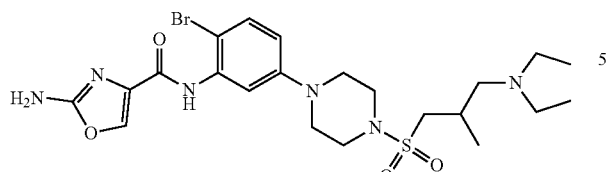

81

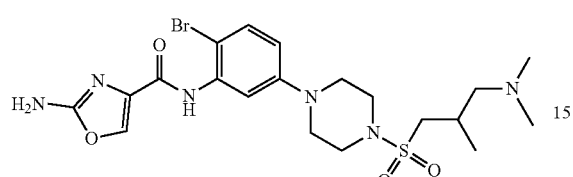

82

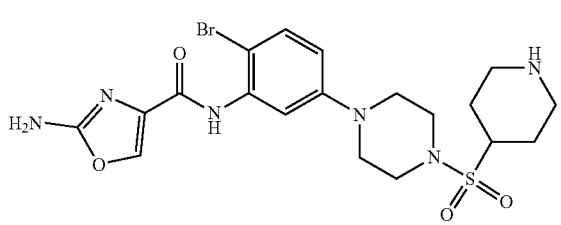

84

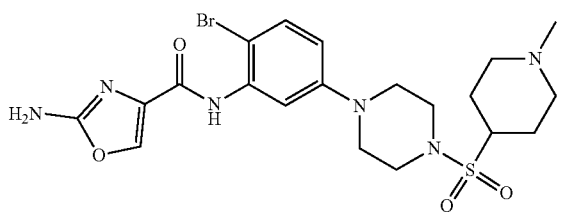

85

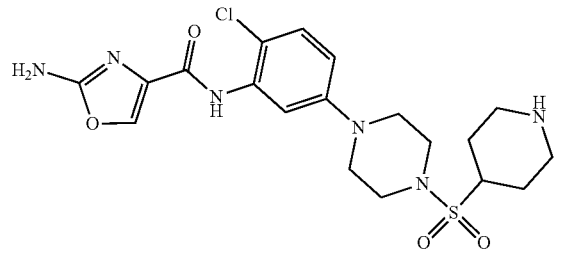

86

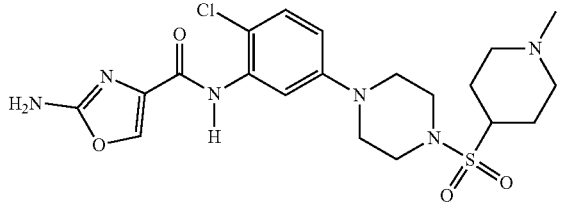

87

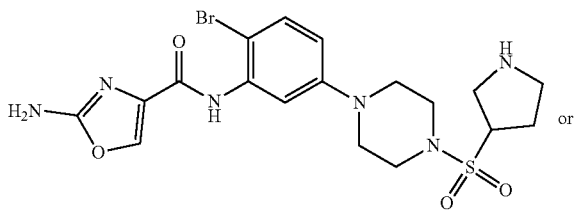

88

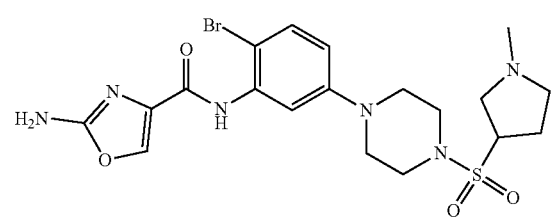

or

89

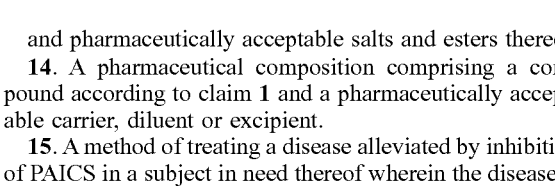

and pharmaceutically acceptable salts and esters thereof.

14. A pharmaceutical composition comprising a compound according to claim 1 and a pharmaceutically acceptable carrier, diluent or excipient.

15. A method of treating a disease alleviated by inhibition of PAICS in a subject in need thereof wherein the disease is a proliferative disorder, said method comprising administering to the subject a therapeutically effective amount of a compound according to claim 1.

16. A method of treating a disease alleviated by inhibition of PAICS in a subject in need thereof wherein the disease is metastatic cancer, said method comprising administering to the subject a therapeutically effective amount of a compound according to claim 1.

17. A method of treating a disease alleviated by inhibition of PAICS in a subject in need thereof wherein the disease is cancer or leukemia, wherein the method comprises administering to the subject a therapeutically effective amount of a compound according to claim 1.

18. A method of treating a disease alleviated by inhibition of PAICS in a subject in need thereof wherein the disease is selected from breast cancer, colon cancer, prostate melanoma, bladder, pancreatic, head and neck and ovarian cancer, with or without metastasis, haematological cancer, acute myeloid leukemia (AML), chronic lymphocytic leukemia (CLL), acute lymphocytic leukemia (ALL), multiple myeloma (MM) and non-Hodgkins lymphoma, wherein the method comprises administering to the subject a therapeutically effective amount of a compound according to claim 1.

19. A method of treating a disease alleviated by inhibition of PAICS in a subject in need thereof wherein the disease is breast cancer, wherein the method comprises administering to the subject a therapeutically effective amount of a compound according to claim 1.

\* \* \* \* \*